US012698539B2

(12) United States Patent
Charne et al.

(10) Patent No.: US 12,698,539 B2
(45) Date of Patent: Aug. 4, 2026

(54) **COMPOSITIONS AND METHODS FOR THE DETECTION OF A CHROMOSOMAL TRANSLOCATION IN *BRASSICA NAPUS***

(71) Applicant: Pioneer Hi-Bred International, Inc., Johnston, IA (US)

(72) Inventors: David George Charne, Guelph (CA); Kevin A Fengler, Clive, IA (US); Siva S. Ammiraju Jetty, Johnston, IA (US); Scott Charles Jobgen, West Des Moines, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 1023 days.

(21) Appl. No.: 17/762,805

(22) PCT Filed: Sep. 24, 2020

(86) PCT No.: PCT/US2020/052443
§ 371 (c)(1),
(2) Date: Mar. 23, 2022

(87) PCT Pub. No.: WO2021/061948
PCT Pub. Date: Apr. 1, 2021

(65) Prior Publication Data
US 2022/0411883 A1 Dec. 29, 2022

Related U.S. Application Data

(60) Provisional application No. 62/906,352, filed on Sep. 26, 2019.

(51) Int. Cl.
| | |
|---|---|
| *C07H 21/04* | (2006.01) |
| *C12Q 1/68* | (2018.01) |
| *C12Q 1/6895* | (2018.01) |

(52) U.S. Cl.
CPC ....... *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,981,183 | B2 | 3/2015 | Preuss et al. |
| 10,407,687 | B2 | 9/2019 | Butler et al. |
| 10,415,049 | B2 | 9/2019 | Butler et al. |
| 2018/0094273 | A1 | 4/2018 | Kumar et al. |
| 2019/0100764 | A1 | 4/2019 | Kumar et al. |

FOREIGN PATENT DOCUMENTS

WO 2019099189 A1 5/2019

OTHER PUBLICATIONS

Osborn et al. Genetics, vol. 165, pp. 1569-1577, Nov. 2003 (Year: 2003).*
Udall et al. Genetics, vol. 169, pp. 967-979, Feb. 2005 (Year: 2005).*
Nicolas, S. et al. "Homeologous recombination plays a major role in chromosome rearrangements that occur during meiosis of *Brassica napus* haploids." Genetics 175.2 (2007): 487-503.
Osborn, T., et al. "Detection and effects of a homeologous reciprocal transposition in *Brassica napus*." Genetics 165.3 (2003): 1569-1577.
William W. *Brasssica oleracea* HDEM genome scaffold: C6, GenGank LR031880.1 [online]. Nov. 16, 2018; Retrieved from the internet [Mar. 1, 2021].
William W. *Brassica rapa* genome: A07 Genbank: LR031574.1 [online]. Nov. 16, 2018: Retreived from the internet [Mar. 1, 2021].
International Search Report for PCT/US2020/052443 dated Mar. 22, 2021.
International Preliminary Report on Patentability for PCT/US2020/052443 dated Mar. 15, 2022.

* cited by examiner

*Primary Examiner* — Jeanine A Goldberg

(57) ABSTRACT

Provided are compositions and methods for the detection of a chromosomal location in *Brassica napus*. This disclosure is generally related to the field of plant molecular biology, and in particular embodiments, to the field of detecting a chromosomal translocation within plants. In certain embodiments, the chromosomal translocation occurs between the N7 and N16 chromosomes of *Brassica napus*. In other embodiments, the chromosomal translocation is a homoeologous chromosomal reciprocal translocation. Accordingly, this disclosure provides compositions and methods for the identification, detection and utilization of such a chromosomal translocation.

8 Claims, No Drawings

Specification includes a Sequence Listing.

COMPOSITIONS AND METHODS FOR THE DETECTION OF A CHROMOSOMAL TRANSLOCATION IN *BRASSICA NAPUS*

CROSS-REFERENCE TO RELATED APPLICATION

This application claims the benefit of PCT/US20/52443, filed Sep. 24, 2020 which claims the benefit of U.S. Provisional Patent Application Ser. No. 62/906,352, filed on Sep. 26, 2019, the disclosure of which is hereby incorporated in its entirety by this reference.

REFERENCE TO A SEQUENCE LISTING

The official copy of the sequence listing is submitted electronically via EFS-Web as an ASCII formatted sequence listing with a file named "Bnapus Chromosomal Translocation 2_ST25", created on Sep. 22, 2020, and having a size of 191 kilobytes and is filed concurrently with the specification. The sequence listing contained in this ASCII formatted document is part of the specification and is herein incorporated by reference in its entirety.

FIELD OF THE INVENTION

This disclosure is generally related to the field of plant molecular biology, and in particular embodiments, to the field of detecting a chromosomal translocation within plants. In certain aspects, the chromosomal translocation occurs between the N7 and N16 chromosomes of *Brassica napus*. In other aspects, the chromosomal translocation is a homoeologous chromosomal reciprocal translocation. Accordingly, this disclosure provides compositions and methods for the identification, detection and utilization of such a chromosomal translocation.

BACKGROUND

*Brassica napus* (canola) is one of the major economic crops grown worldwide as a primary source of vegetable oil. Growing demand for diets with healthy oil has increased *B. napus* importance as a food. *B. napus* is one of the lowest-cost sources of vegetable oil. *B. napus* oil accounts for a large proportion of edible oil consumed worldwide. It is used as a liquid oil, in baking, frying, salad dressing, margarine, and a multitude of processed foods. *B. napus* is agronomically well-adapted to many parts of the world and production continues to expand from year to year. The low cost and ready availability of *B. napus* oil provides an excellent opportunity to upgrade this commodity oil into higher value specialty oils that add value to the farmer. The development of new and improved lines of *B. napus* remains a continual challenge for breeders.

*B. napus* is a recently formed allo-tetraploid species that contains two closely related homoeologous sub-genome types, named A and C. Although a tetraploid, canola behaves genetically as a diploid, due to strict control on the meiotic chromosome pairing that prevent recombination between highly similar homoeologous chromosomes. However, "de novo" recombination can occur between A and C genomes at low frequency in 'natural' polyploids of canola (unlike re-synthesized canola, where these events occur at a higher frequency), leading to a variety of large homoeologous chromosomal structural rearrangements (HCR). Few historical HCR are artificially selected and fixed in the canola germplasm inadvertently due to their linkage with traits of commercial importance. One class of HCR is reciprocal translocation (homoeologous chromosomal reciprocal translocation), where homoeologous recombination result in reciprocal swapping of parts of the A and C chromosomes without loss of any genetic material. Progenies derived from crosses between *B. napus* plants differing for the presence or absence of an homoeologous chromosomal reciprocal translocation can be classified into two groups. Those with 'parental type' chromosomal constitution with no apparent loss or gain of genetic material, and those with 'non-parental recombinant type' chromosomal constitution that result in duplication or deletion of genetic material. The second, will result in complex non-mendelian segregation patterns. Few 'fixed' homoeologous chromosomal reciprocal translocations have been identified and reported in the literature for *B. napus*.

Molecular breeding assays that can be utilized for breeding new lines of *B. napus* are desirable. For example, assays that can be used to detect and monitor homoeologous chromosomal reciprocal translocations within *B. napus* are of particular importance.

Therefore, there is an important need in the art to continue to identify novel methods and compositions for molecular breeding assays that can be readily applied for breeding in *B. napus*.

SUMMARY

Disclosed herein are sequences, constructs, and methods for the detection of an a N7/N16 homoeologous chromosomal reciprocal translocation in a canola plant, tissue, or cell. In some aspects the disclosure relates to the detection of at least one PCR amplicon of the N7/N16 homoeologous chromosomal reciprocal translocation, wherein the one or more PCR amplicons localize within either SEQ ID NO:2 or SEQ ID NO:4. In additional aspect, the disclosure relates to screening the first canola plant, tissue, or cell for the N7/N16 homoeologous chromosomal reciprocal translocation. In other aspects, the disclosure relates to selecting the first canola plant, tissue, or cell or selecting a progeny of the first canola plant, tissue, or cell whereby the resulting plant, tissue, or cell displays the N7/N16 homoeologous chromosomal reciprocal translocation. In further aspects, the amplicon of SEQ ID NO:2 comprises a primer associated with any one of SEQ ID NO:5493-8026, SEQ ID NO:9, SEQ ID NO: 10, SEQ ID NO:14, SEQ ID NO: 16 or a complement thereof. Accordingly, the amplicon of SEQ ID NO:2 comprises a forward or 5' primer associated with any one of SEQ ID NO:5493-8026, SEQ ID NO:9, SEQ ID NO: 10, SEQ ID NO: 14, SEQ ID NO:16 or a complement thereof. Likewise, the amplicon of SEQ ID NO:2 comprises a reverse or 3' primer associated with any one of SEQ ID NO:5493-8026, SEQ ID NO: 9, SEQ ID NO: 10, SEQ ID NO: 14, SEQ ID NO: 16 or a complement thereof. In some aspects, the amplicon of SEQ ID NO:2 comprises a probe associated with any one of SEQ ID NO: 372-488 or a complement thereof. In additional aspects, the amplicon of SEQ ID NO:4 comprises a primer associated with any one of SEQ ID NO: 8027-10560, SEQ ID NO: 11, SEQ ID NO: 12, SEQ ID NO:18, SEQ ID NO:20 or a complement thereof. Accordingly, the amplicon of SEQ ID NO:4 comprises a forward or 5' primer associated with any one of SEQ ID NO: 8027-10560, SEQ ID NO:11, SEQ ID NO:12, SEQ ID NO:18, SEQ ID NO:20 or a complement thereof. Likewise, the amplicon of SEQ ID NO:4 comprises a reverse or 3' primer associated with any one of SEQ ID NO: 8027-10560, SEQ ID NO:11, SEQ ID NO: 12, SEQ ID NO: 18, SEQ ID NO:20 or a complement thereof. In other aspects, the amplicon of SEQ ID NO:4 comprises a probe associated with any one of SEQ ID NO:255-371 or a complement thereof. In further aspects, the amplicon of SEQ ID NO:2 comprises a polynucleotide that shares at least 98% sequence identity with a primer associated with any one of SEQ ID NO:5493-8026, SEQ ID NO: 9, SEQ ID NO: 10, SEQ ID NO: 14, SEQ ID NO: 16 or a complement thereof. In other aspects, the amplicon of SEQ ID NO:2 comprises a polynucleotide that shares at least 95%, 96%, 97%, 98%, or 99% sequence identity with a primer associated with any one of SEQ ID NO: 5493-8026, SEQ ID NO:9, SEQ ID NO: 10, SEQ ID NO: 14, SEQ ID NO: 16 or a complement thereof. In an aspect, the amplicon of SEQ ID NO:2 comprises a probe that shares at least 95%, 96%, 97%, 98%, or 99% sequence identity with a probe associated with any one of SEQ ID NO:372-488 or a complement thereof. In some aspects, the amplicon of SEQ ID NO:4 comprises a polynucleotide that shares at least 98% sequence identity with a primer associated with any one of SEQ ID NO: 8027-10560, SEQ ID NO:11, SEQ ID NO: 12, SEQ ID NO: 18, SEQ ID NO:20 or a complement thereof. In further aspects, the amplicon of SEQ ID NO:4 comprises a polynucleotide that shares at least 95%, 96%, 97%, 98%, or 99% sequence identity with a primer associated with any one SEQ ID NO: 8027-10560, SEQ ID NO:11, SEQ ID NO: 12, SEQ ID NO:18, SEQ ID NO:20 or a complement thereof. In a further aspect, the amplicon of SEQ ID NO:4 comprises a probe that shares at least 95%, 96%, 97%, 98%, or 99% sequence identity with a probe associated with any one of SEQ ID NO:255-371 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

Disclosed herein are sequences, constructs, and methods for the detection of an a N7/N16 homoeologous chromosomal reciprocal translocation in a canola plant, tissue, or cell. In some aspects the disclosure relates to the detection of at least one PCR amplicon associated with the N7/N16 homoeologous chromosomal reciprocal translocation, wherein the one or more PCR amplicons localize within either SEQ ID NO: 1 or SEQ ID NO:3. In additional aspect, the disclosure relates to screening the first canola plant, tissue, or cell for the N7/N16 homoeologous chromosomal reciprocal translocation. In other aspects, the disclosure relates to selecting the first canola plant, tissue, or cell or selecting a progeny of the first canola plant, tissue, or cell whereby the resulting plant, tissue, or cell displays the N7/N16 homoeologous chromosomal reciprocal translocation. In further aspects, the amplicon of SEQ ID NO: 1 comprises a primer associated with any one of SEQ ID NO: 489-2990, SEQ ID NO:5 SEQ ID NO:6, SEQ ID NO: 13, SEQ ID NO: 15 or a complement thereof. Accordingly, the amplicon of SEQ ID NO: 1 comprises a forward or 5' primer associated with any one of SEQ ID NO: 489-2990, SEQ ID NO: 5 SEQ ID NO:6, SEQ ID NO: 13, SEQ ID NO: 15 or a complement thereof. Likewise, the amplicon of SEQ ID NO: 1 comprises a reverse or 3' primer associated with any one of SEQ ID NO: 489-2990, SEQ ID NO:5 SEQ ID NO:6, SEQ ID NO: 13, SEQ ID NO: 15 or a complement thereof. In some aspects, the amplicon of SEQ ID NO: 1 comprises a probe associated with any one of SEQ ID NO: 138-254 or a complement thereof. In additional aspects, the amplicon of SEQ ID NO:3 comprises a primer associated with any one of SEQ ID NO: 2991-5492, SEQ ID NO: 7, SEQ ID NO:8, SEQ ID NO:17, SEQ ID NO: 19 or a complement thereof. Accordingly, the amplicon of SEQ ID NO:3 comprises a forward or 5' primer associated with any one of SEQ ID NO: 2991-5492, SEQ ID NO:7, SEQ ID NO:8, SEQ ID NO: 17, SEQ ID NO: 19 or a complement thereof. Likewise, the amplicon of SEQ ID NO:3 comprises a reverse or 3' primer associated with any one of SEQ ID NO: 2991-5492, SEQ ID NO:7, SEQ ID NO:8, SEQ ID NO: 17, SEQ ID NO:19 or a complement thereof. In other aspects, the amplicon of SEQ ID NO: 3 comprises a probe associated with any one of SEQ ID NO: 21-137 or a complement thereof. In further aspects, the amplicon of SEQ ID NO: 1 comprises a polynucleotide that shares at least 98% sequence identity with a primer associated with any one of SEQ ID NO: 489-2990, SEQ ID NO:5 SEQ ID NO:6, SEQ ID NO: 13, SEQ ID NO: 15 or a complement thereof. In other aspects, the amplicon of SEQ ID NO: 1 comprises a polynucleotide that shares at least 95%, 96%, 97%, 98%, or 99% sequence identity with a primer associated with any one of SEQ ID NO: 489-2990, SEQ ID NO:5 SEQ ID NO:6, SEQ ID NO:13, SEQ ID NO:15 or a complement thereof. In an aspect, the amplicon of SEQ ID NO: 1 comprises a probe that shares at least 95%, 96%, 97%, 98%, or 99% sequence identity with a probe associated with any one of SEQ ID NO:138-254 or a complement thereof. In some aspects, the amplicon of SEQ ID NO:3 comprises a polynucleotide that shares at least 98% sequence identity with a primer associated with any one of SEQ ID NO: 2991-5492, SEQ ID NO:7, SEQ ID NO:8, SEQ ID NO: 17, SEQ ID NO: 19 or a complement thereof. In further aspects, the amplicon of SEQ ID NO:3 comprises a polynucleotide that shares at least 95%, 96%, 97%, 98%, or 99% sequence identity with a primer associated with any one SEQ ID NO: 2991-5492, SEQ ID NO:7, SEQ ID NO:8, SEQ ID NO: 17, SEQ ID NO:19 or a complement thereof. In a further aspect, the amplicon of SEQ ID NO:3 comprises a probe that shares at least 95%, 96%, 97%, 98%, or 99% sequence identity with a probe associated with any one of SEQ ID NO: 21-137 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In other aspects, the disclosure relates to a canola plant selected using the methods and compositions of the subject disclosure. In an aspect, the canola plant can be a progeny canola plant obtained from the canola plant selected using the methods and compositions of the subject disclosure. In further aspects, the canola plant comprises a canola seed. Exemplary structures of the canola seed include the outer hull and the embryo. In other aspects, the canola plant comprises a canola plant part. Exemplary canola plant parts include plant cells, plant protoplasts, plant cell tissue cultures from which plants can be regenerated, plant DNA, plant calli, plant clumps, and plant cells that are intact in plants or parts of plants, such as embryos, pollen, ovules, flowers, seeds, leaves, roots, root tips, anthers, and the like. In such embodiments, the canola plant is assayed for the presence or absence of the N7/N16 homoeologous chromosomal reciprocal translocation using the compositions and methods of the subject disclosure.

In an aspect, the disclosure relates to introgressing the N7/N16 homoeologous chromosomal reciprocal translocation into a progeny canola plant. In a further aspect, the disclosure relates to crossing a parent canola plant with another parent canola plant, wherein at least one parent canola plant comprises the N7/N16 homoeologous chromosomal reciprocal translocation. In another aspect, the disclosure relates to harvesting a progeny seed from the crossing as described previously, wherein the progeny seed comprises the N7/N16 homoeologous chromosomal reciprocal translocation. In an additional aspect, the disclosure relates to planting the progeny seed. In a further aspect, the disclosure relates to growing the progeny seed, wherein the progeny seed produce a progeny canola plant, wherein the progeny canola plant comprises the N7/N16 homoeologous chromosomal reciprocal translocation.

In some aspects the disclosure relates to introgressing the N7/N16 homoeologous chromosomal reciprocal translocation into a progeny canola plant, wherein introgression occurs within either SEQ ID NO:2 or SEQ ID NO:4. In further aspects, the introgression of the N7/N16 homoeologous chromosomal reciprocal translocation into a progeny canola plant is detected by producing an amplicon of SEQ ID NO:2, wherein the amplicon comprises a primer associated with any one of SEQ ID NO:5493-8026, SEQ ID NO:9, SEQ ID NO: 10, SEQ ID NO: 14, SEQ ID NO: 16 or a complement thereof. Accordingly, the amplicon of SEQ ID NO:2 comprises a forward or 5' primer associated with any one of SEQ ID NO:5493-8026, SEQ ID NO:9, SEQ ID NO: 10, SEQ ID NO:14, SEQ ID NO: 16 or a complement thereof. Likewise, the amplicon of SEQ ID NO:2 comprises a reverse or 3' primer associated with any one of SEQ ID NO:5493-8026, SEQ ID NO:9, SEQ ID NO: 10, SEQ ID NO: 14, SEQ ID NO: 16 or a complement thereof. In some aspects, the amplicon of SEQ ID NO:2 comprises a probe associated with any one of SEQ ID NO:372-488 or a complement thereof. In other aspects, the introgression of the N7/N16 homoeologous chromosomal reciprocal translocation into a progeny canola plant is detected by producing an amplicon of SEQ ID NO:4, wherein the amplicon comprises a primer associated with any one of SEQ ID NO: 8027-10560, SEQ ID NO:11, SEQ ID NO: 12, SEQ ID NO:18, SEQ ID NO:20 or a complement thereof. Accordingly, the amplicon of SEQ ID NO:4 comprises a forward or 5' primer associated with any one of SEQ ID NO: 8027-10560, SEQ ID NO:11, SEQ ID NO:12, SEQ ID NO:18, SEQ ID NO:20 or a complement thereof. Likewise, the amplicon of SEQ ID NO:4 comprises a reverse or 3' primer associated with any one of SEQ ID NO: 8027-10560, SEQ ID NO:11, SEQ ID NO: 12, SEQ ID NO: 18, SEQ ID NO:20 or a complement thereof. In other aspects, the amplicon of SEQ ID NO:4 comprises a probe associated with any one of SEQ ID NO:255-371 or a complement thereof. In further aspects, the amplicon of SEQ ID NO:2 comprises a polynucleotide that shares at least 98% sequence identity with a primer associated with any one of SEQ ID NO:5493-8026, SEQ ID NO:9, SEQ ID NO: 10, SEQ ID NO:14, SEQ ID NO: 16 or a complement thereof. In other aspects, the amplicon of SEQ ID NO:2 comprises a polynucleotide that shares at least 95%, 96%, 97%, 98%, or 99% sequence identity with a primer associated with any one of SEQ ID NO:5493-8026, SEQ ID NO: 9, SEQ ID NO: 10, SEQ ID NO: 14, SEQ ID NO: 16 or a complement thereof. In an aspect, the amplicon of SEQ ID NO:2 comprises a probe that shares at least 95%, 96%, 97%, 98%, or 99% sequence identity with a probe associated with any one of SEQ ID NO:372-488 or a complement thereof. In some aspects, the amplicon of SEQ ID NO:4 comprises a polynucleotide that shares at least 98% sequence identity with a primer associated with any one of SEQ ID NO: 8027-10560, SEQ ID NO:11, SEQ ID NO:12, SEQ ID NO: 18, SEQ ID NO:20 or a complement thereof. In further aspects, the amplicon of SEQ ID NO:4 comprises a polynucleotide that shares at least 95%, 96%, 97%, 98%, or 99% sequence identity with a primer associated with any one SEQ ID NO: 8027-10560, SEQ ID NO: 11, SEQ ID NO: 12, SEQ ID NO:18, SEQ ID NO:20 or a complement thereof. In a further aspect, the amplicon of SEQ ID NO:4 comprises a probe that shares at least 95%, 96%, 97%, 98%, or 99% sequence identity with a probe associated with any one of SEQ ID NO:255-371 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In some aspects the disclosure relates to introgressing the N7/N16 homoeologous chromosomal reciprocal translocation into a progeny canola plant, wherein introgression occurs within either SEQ ID NO:1 or SEQ ID NO:3. In further aspects, the introgression of the N7/N16 homoeologous chromosomal reciprocal translocation into a progeny canola plant is detected by producing an amplicon of SEQ ID NO:1, wherein the amplicon comprises a primer associated with any one of SEQ ID NO: 489-2990, SEQ ID NO:5 SEQ ID NO:6, SEQ ID NO: 13, SEQ ID NO: 15 or a complement thereof. Accordingly, the amplicon of SEQ ID NO: 1 comprises a forward or 5' primer associated with any one of SEQ ID NO: 489-2990, SEQ ID NO:5 SEQ ID NO: 6, SEQ ID NO:13, SEQ ID NO: 15 or a complement thereof. Likewise, the amplicon of SEQ ID NO: 1 comprises a reverse or 3' primer associated with any one of SEQ ID NO: 489-2990, SEQ ID NO:5 SEQ ID NO:6, SEQ ID NO: 13, SEQ ID NO: 15 or a complement thereof. In some aspects, the amplicon of SEQ ID NO: 1 comprises a probe associated with any one of SEQ ID NO: 138-254 or a complement thereof. In further aspects, the introgression of the N7/N16 homoeologous chromosomal reciprocal translocation into a progeny canola plant is detected by producing an amplicon of SEQ ID NO:3, wherein the amplicon comprises a primer associated with any one of SEQ ID NO: 2991-5492, SEQ ID NO: 7, SEQ ID NO:8, SEQ ID NO: 17, SEQ ID NO: 19 or a complement thereof. Accordingly, the amplicon of SEQ ID NO:3 comprises a forward or 5' primer associated with any one of SEQ ID NO: 2991-5492, SEQ ID NO:7, SEQ ID NO: 8, SEQ ID NO: 17, SEQ ID NO: 19 or a complement thereof. Likewise, the amplicon of SEQ ID NO:3 comprises a reverse or 3' primer associated with any one of SEQ ID NO: 2991-5492, SEQ ID NO:7, SEQ ID NO:8, SEQ ID NO: 17, SEQ ID NO: 19 or a complement thereof. In other aspects, the amplicon of SEQ ID NO:3 comprises a probe associated with any one of SEQ ID NO: 21-137 or a complement thereof. In further aspects, the amplicon of SEQ ID NO:1 comprises a polynucleotide that shares at least 98% sequence identity with a primer associated with any one of SEQ ID NO: 489-2990, SEQ ID NO:5 SEQ ID NO:6, SEQ ID NO: 13, SEQ ID NO: 15 or a complement thereof. In other aspects, the amplicon of SEQ ID NO: 1 comprises a polynucleotide that shares at least 95%, 96%, 97%, 98%, or 99% sequence identity with a primer associated with any one of SEQ ID NO: 489-2990, SEQ ID NO:5 SEQ ID NO:6, SEQ ID NO: 13, SEQ ID NO: 15 or a complement thereof. In an aspect, the amplicon of SEQ ID NO: 1 comprises a probe that shares at least 95%, 96%, 97%, 98%, or 99% sequence identity with a probe associated with any one of SEQ ID NO: 138-254 or a complement thereof. In some aspects, the amplicon of SEQ ID NO:3 comprises a polynucleotide that shares at least 98% sequence identity with a primer associated with any one of SEQ ID NO: 2991-5492, SEQ ID NO: 7, SEQ ID NO:8, SEQ ID NO:17, SEQ ID NO: 19 or a complement thereof. In further aspects, the amplicon of SEQ ID NO:3 comprises a polynucleotide that shares at least 95%, 96%, 97%, 98%, or 99% sequence identity with a primer associated with any one SEQ ID NO: 2991-5492, SEQ ID NO:7, SEQ ID NO:8, SEQ ID NO: 17, SEQ ID NO: 19 or a complement thereof. In a further aspect, the amplicon of SEQ ID NO:3 comprises a probe that shares at least 95%, 96%, 97%, 98%, or 99% sequence identity with a probe associated with any one of SEQ ID NO: 21-137 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In another aspect, the disclosure relates to a PCR assay method for determining zygosity of a N7/N16 homoeologous chromosomal reciprocal translocation in a canola plant, tissue, or cell. In some aspects, the disclosure relates to performing a first PCR assay using a first probe, a first forward primer, and a first reverse primer on a polynucleotide from a canola plant sample. In other aspects, the disclosure relates to performing a second PCR assay using a second probe, a second forward primer, and a second reverse primer on the polynucleotide sample. In further aspects, the disclosure relates to quantifying the first probe and the second probe. In additional aspect, the disclosure relates to comparing the quantified first probe and the quantified second probe of the first PCR assay and the second PCR assay to determine the zygosity, wherein the zygosity of the N7/N16 homoeologous chromosomal reciprocal translocation is selected from the group consisting of homozygous, heterozygous, hemizygous, and nullizygous. In an aspect, the first and the second PCR assays are a multiplex PCR-format. In another aspect, the first and second PCR assays are performed in a single PCR assay tube or well. In an additional aspect, the first and the second PCR assays are a real-time PCR. In other aspects, the first probe and the second probe are quantified by measuring excitation/emission spectra emitted from the fluorescent dyes, during the amplification. In further aspects, the zygosity is determined by comparing the quantified first probe and the second probe using a ΔΔCt formula.

In some aspects the disclosure relates to a PCR assay method for determining zygosity of a N7/N16 homoeologous chromosomal reciprocal translocation in a canola plant, tissue, or cell, wherein PCR assay occurs within either SEQ ID NO:2 or SEQ ID NO:4. In further aspects, the PCR assay to determine zygosity of the N7/N16 homoeologous chromosomal reciprocal translocation into a progeny canola plant is detected by producing an amplicon of SEQ ID NO:2, wherein the amplicon comprises a primer associated with any one of SEQ ID NO:5493-8026, SEQ ID NO:9, SEQ ID NO:10, SEQ ID NO:14, SEQ ID NO:16 or a complement thereof. Accordingly, the amplicon of SEQ ID NO:2 comprises a forward or 5' primer associated with any one of SEQ ID NO:5493-8026, SEQ ID NO:9, SEQ ID NO: 10, SEQ ID NO: 14, SEQ ID NO: 16 or a complement thereof. Likewise, the amplicon of SEQ ID NO:2 comprises a reverse or 3' primer associated with any one of SEQ ID NO:5493-8026, SEQ ID NO:9, SEQ ID NO:10, SEQ ID NO: 14, SEQ ID NO: 16 or a complement thereof. In some aspects, the amplicon of SEQ ID NO: 2 comprises a probe associated with any one of SEQ ID NO:372-488 or a complement thereof. In other aspects, the PCR assay method for determining zygosity of a N7/N16 homoeologous chromosomal reciprocal translocation in a canola plant is detected by producing an amplicon of SEQ ID NO:4, wherein the amplicon comprises a primer associated with any one of SEQ ID NO: 8027-10560, SEQ ID NO: 11, SEQ ID NO: 12, SEQ ID NO: 18, SEQ ID NO:20 or a complement thereof. Accordingly, the amplicon of SEQ ID NO:4 comprises a forward or 5' primer associated with any one of SEQ ID NO: 8027-10560, SEQ ID NO: 11, SEQ ID NO: 12, SEQ ID NO:18, SEQ ID NO:20 or a complement thereof. Likewise, the amplicon of SEQ ID NO: 4 comprises a reverse or 3' primer associated with any one of SEQ ID NO: 8027-10560, SEQ ID NO:11, SEQ ID NO: 12, SEQ ID NO: 18, SEQ ID NO:20 or a complement thereof. In other aspects, the amplicon of SEQ ID NO:4 comprises a probe associated with any one of SEQ ID NO: 255-371 or a complement thereof. In further aspects, the amplicon of SEQ ID NO:2 comprises a polynucleotide that shares at least 98% sequence identity with a primer associated with any one of SEQ ID NO:5493-8026, SEQ ID NO:9, SEQ ID NO: 10, SEQ ID NO: 14, SEQ ID NO: 16 or a complement thereof. In other aspects, the amplicon of SEQ ID NO:2 comprises a polynucleotide that shares at least 95%, 96%, 97%, 98%, or 99% sequence identity with a primer associated with any one of SEQ ID NO:5493-8026, SEQ ID NO:9, SEQ ID NO: 10, SEQ ID NO: 14, SEQ ID NO:16 or a complement thereof. In an aspect, the amplicon of SEQ ID NO:2 comprises a probe that shares at least 95%, 96%, 97%, 98%, or 99% sequence identity with a probe associated with any one of SEQ ID NO:372-488 or a complement thereof. In some aspects, the amplicon of SEQ ID NO:4 comprises a polynucleotide that shares at least 98% sequence identity with a primer associated with any one of SEQ ID NO: 8027-10560, SEQ ID NO: 11, SEQ ID NO:12, SEQ ID NO:18, SEQ ID NO:20 or a complement thereof. In further aspects, the amplicon of SEQ ID NO:4 comprises a polynucleotide that shares at least 95%, 96%, 97%, 98%, or 99% sequence identity with a primer associated with any one SEQ ID NO: 8027-10560, SEQ ID NO:11, SEQ ID NO: 12, SEQ ID NO:18, SEQ ID NO:20 or a complement thereof. In a further aspect, the amplicon of SEQ ID NO:4 comprises a probe that shares at least 95%, 96%, 97%, 98%, or 99% sequence identity with a probe associated with any one of SEQ ID NO: 255-371 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In some aspects the disclosure relates to a PCR assay method for determining zygosity of a N7/N16 homoeologous chromosomal reciprocal translocation in a canola plant, tissue, or cell, wherein PCR assay occurs within either SEQ ID NO:1 or SEQ ID NO:3. In further aspects, the PCR assay to determine zygosity of the N7/N16 homoeologous chromosomal reciprocal translocation into a progeny canola plant is detected by producing an amplicon of SEQ ID NO:1, wherein the amplicon comprises a primer associated with any one of SEQ ID NO: 489-2990, SEQ ID NO:5 SEQ ID NO:6, SEQ ID NO: 13, SEQ ID NO: 15 or a complement thereof. Accordingly, the amplicon of SEQ ID NO: 1 comprises a forward or 5' primer associated with any one of SEQ ID NO: 489-2990, SEQ ID NO:5 SEQ ID NO:6, SEQ ID NO: 13, SEQ ID NO: 15 or a complement thereof. Likewise, the amplicon of SEQ ID NO: 1 comprises a reverse or 3' primer associated with any one of SEQ ID NO: 489-2990, SEQ ID NO:5 SEQ ID NO:6, SEQ ID NO:13, SEQ ID NO: 15 or a complement thereof. In some aspects, the amplicon of SEQ ID NO: 1 comprises a probe associated with any one of SEQ ID NO:138-254 or a complement thereof. In further aspects, the PCR assay to determine zygosity of the N7/N16 homoeologous chromosomal reciprocal translocation into a progeny canola plant is detected by producing an amplicon of SEQ ID NO:3, wherein the amplicon comprises a primer associated with any one of SEQ ID NO: 2991-5492, SEQ ID NO: 7, SEQ ID NO:8, SEQ ID NO: 17, SEQ ID NO: 19 or a complement thereof. Accordingly, the amplicon of SEQ ID NO:3 comprises a forward or 5' primer associated with any one of SEQ ID NO: 2991-5492, SEQ ID NO:7, SEQ ID NO:8, SEQ ID NO: 17, SEQ ID NO: 19 or a complement thereof. Likewise, the amplicon of SEQ ID NO:3 comprises a reverse or 3' primer associated with any one of SEQ ID NO: 2991-5492, SEQ ID NO: 7, SEQ ID NO:8, SEQ ID NO: 17, SEQ ID NO: 19 or a complement thereof. In other aspects, the amplicon of SEQ ID NO:3 comprises a probe associated with any one of SEQ ID NO: 21-137 or a complement thereof. In further aspects, the amplicon of SEQ ID NO:1 comprises a polynucleotide that shares at least 98% sequence identity with a primer associated with any one of SEQ ID NO: 489-2990, SEQ ID NO:5 SEQ ID NO:6, SEQ ID NO: 13, SEQ ID NO: 15 or a complement thereof. In other aspects, the amplicon of SEQ ID NO: 1 comprises a polynucleotide that shares at least 95%, 96%, 97%, 98%, or 99% sequence identity with a primer associated with any one of SEQ ID NO: 489-2990, SEQ ID NO:5 SEQ ID NO:6, SEQ ID NO: 13, SEQ ID NO:15 or a complement thereof. In an aspect, the amplicon of SEQ ID NO: 1 comprises a probe that shares at least 95%, 96%, 97%, 98%, or 99% sequence identity with a probe associated with any one of SEQ ID NO: 138-254 or a complement thereof. In some aspects, the amplicon of SEQ ID NO:3 comprises a polynucleotide that shares at least 98% sequence identity with a primer associated with any one of SEQ ID NO: 2991-5492, SEQ ID NO: 7, SEQ ID NO:8, SEQ ID NO: 17, SEQ ID NO: 19 or a complement thereof. In further aspects, the amplicon of SEQ ID NO:3 comprises a polynucleotide that shares at least 95%, 96%, 97%, 98%, or 99% sequence identity with a primer associated with any one SEQ ID NO: 2991-5492, SEQ ID NO:7, SEQ ID NO:8, SEQ ID NO: 17, SEQ ID NO: 19 or a complement thereof. In a further aspect, the amplicon of SEQ ID NO:3 comprises a probe that shares at least 95%, 96%, 97%, 98%, or 99% sequence identity with a probe associated with any one of SEQ ID NO: 21-137 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In an aspect, the subject disclosure relates to introgressing a N7/N16 homoeologous chromosomal reciprocal translocation into canola germplasm. In a further aspect, the disclosures relates to detecting in a first canola plant at least one at least one PCR amplicon associated with the N7/N16 homoeologous chromosomal reciprocal translocation, wherein the one or more PCR amplicons localize within either SEQ ID NO:1, SEQ ID NO:2, SEQ ID NO:3, or SEQ ID NO:4. In another aspect, the disclosure relates to introgressing the N7/N16 homoeologous chromosomal reciprocal translocation into canola germplasm. In an aspect, disclosure relates to introgressing a trait within 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilobase pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs of SEQ ID NO:2 or SEQ ID NO: 4. In a further aspect, disclosure relates to introgressing a trait within 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilobase pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs of SEQ ID NO:1 or SEQ ID NO:3. In other aspects, the trait is selected from the group consisting of an insecticidal resistance trait, a herbicide tolerance trait, a nitrogen use efficiency trait, a water use efficiency trait, a nutritional quality trait, a DNA binding trait, a selectable marker trait, a blackleg resistance trait, a *Fusarium* wilt trait, a White Rust tolerance trait, a lodging resistance trait, a plant height trait, an earliness of maturity trait, an oil trait, a protein trait, and a glucosinolate trait.

In some aspects the disclosure relates to a PCR assay method for detecting the trait that is introgressed within 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilobase pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs of a N7/N16 homoeologous chromosomal reciprocal translocation in a canola plant, tissue, or cell, wherein PCR assay occurs within either SEQ ID NO:2 or SEQ ID NO:4. In further aspects, the PCR assay of the N7/N16 homoeologous chromosomal reciprocal translocation into a progeny canola plant is detected by producing an amplicon of SEQ ID NO:2, wherein the amplicon comprises a primer associated with any one of SEQ ID NO:5493-8026, SEQ ID NO:9, SEQ ID NO: 10, SEQ ID NO: 14, SEQ ID NO: 16 or a complement thereof. Accordingly, the amplicon of SEQ ID NO:2 comprises a forward or 5' primer associated with any one of SEQ ID NO:5493-8026, SEQ ID NO:9, SEQ ID NO: 10, SEQ ID NO:14, SEQ ID NO: 16 or a complement thereof. Likewise, the amplicon of SEQ ID NO:2 comprises a reverse or 3' primer associated with any one of SEQ ID NO:5493-8026, SEQ ID NO:9, SEQ ID NO: 10, SEQ ID NO:14, SEQ ID NO: 16 or a complement thereof. In some aspects, the amplicon of SEQ ID NO:2 comprises a probe associated with any one of SEQ ID NO:372-488 or a complement thereof. In other aspects, the PCR assay of the N7/N16 homoeologous chromosomal reciprocal translocation in a canola plant is detected by producing an amplicon of SEQ ID NO:4, wherein the amplicon comprises a primer associated with any one of SEQ ID NO: 8027-10560, SEQ ID NO:11, SEQ ID NO: 12, SEQ ID NO: 18, SEQ ID NO:20 or a complement thereof. Accordingly, the amplicon of SEQ ID NO:4 comprises a forward or 5' primer associated with any one of SEQ ID NO: 8027-10560, SEQ ID NO:11, SEQ ID NO:12, SEQ ID NO: 18, SEQ ID NO:20 or a complement thereof. Likewise, the amplicon of SEQ ID NO: 4 comprises a reverse or 3' primer associated with any one of SEQ ID NO: 8027-10560, SEQ ID NO:11, SEQ ID NO:12, SEQ ID NO:18, SEQ ID NO:20 or a complement thereof. In other aspects, the amplicon of SEQ ID NO:4 comprises a probe associated with any one of SEQ ID NO: 255-371 or a complement thereof. In further aspects, the amplicon of SEQ ID NO:2 comprises a polynucleotide that shares at least 98% sequence identity with a primer associated with any one of SEQ ID NO:5493-8026, SEQ ID NO:9, SEQ ID NO: 10, SEQ ID NO: 14, SEQ ID NO: 16 or a complement thereof. In other aspects, the amplicon of SEQ ID NO:2 comprises a polynucleotide that shares at least 95%, 96%, 97%, 98%, or 99% sequence identity with a primer associated with any one of SEQ ID NO:5493-8026, SEQ ID NO:9, SEQ ID NO: 10, SEQ ID NO: 14, SEQ ID NO:16 or a complement thereof. In an aspect, the amplicon of SEQ ID NO:2 comprises a probe that shares at least 95%, 96%, 97%, 98%, or 99% sequence identity with a probe associated with any one of SEQ ID NO:372-488 or a complement thereof. In some aspects, the amplicon of SEQ ID NO:4 comprises a polynucleotide that shares at least 98% sequence identity with a primer associated with any one of SEQ ID NO: 8027-10560, SEQ ID NO: 11, SEQ ID NO:12, SEQ ID NO:18, SEQ ID NO:20 or a complement thereof. In further aspects, the amplicon of SEQ ID NO:4 comprises a polynucleotide that shares at least 95%, 96%, 97%, 98%, or 99% sequence identity with a primer associated with any one SEQ ID NO: 8027-10560, SEQ ID NO:11, SEQ ID NO: 12, SEQ ID NO: 18, SEQ ID NO:20 or a complement thereof. In a further aspect, the amplicon of SEQ ID NO:4 comprises a probe that shares at least 95%, 96%, 97%, 98%, or 99% sequence identity with a probe associated with any one of SEQ ID NO: 255-371 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In some aspects the disclosure relates to a PCR assay method for detecting the trait that is introgressed within 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilobase pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs of a N7/N16 homoeologous chromosomal reciprocal translocation in a canola plant, tissue, or cell, wherein PCR assay occurs within either SEQ ID NO: 1 or SEQ ID NO:3. In further aspects, the PCR assay of the N7/N16 homoeologous chromosomal reciprocal translocation into a progeny canola plant is detected by producing an amplicon of SEQ ID NO:1, wherein the amplicon comprises a primer associated with any one of SEQ ID NO: 489-2990, SEQ ID NO:5 SEQ ID NO:6, SEQ ID NO: 13, SEQ ID NO: 15 or a complement thereof. Accordingly, the amplicon of SEQ ID NO: 1 comprises a forward or 5' primer associated with any one of SEQ ID NO: 489-2990, SEQ ID NO:5 SEQ ID NO: 6, SEQ ID NO: 13, SEQ ID NO: 15 or a complement thereof. Likewise, the amplicon of SEQ ID NO: 1 comprises a reverse or 3' primer associated with any one of SEQ ID NO: 489-2990, SEQ ID NO:5 SEQ ID NO:6, SEQ ID NO: 13, SEQ ID NO: 15 or a complement thereof. In some aspects, the amplicon of SEQ ID NO: 1 comprises a probe associated with any one of SEQ ID NO: 138-254 or a complement thereof. In further aspects, the PCR assay is detected by producing an amplicon of SEQ ID NO:3, wherein the amplicon comprises a primer associated with any one of SEQ ID NO: 2991-5492, SEQ ID NO:7, SEQ ID NO:8, SEQ ID NO: 17, SEQ ID NO: 19 or a complement thereof. Accordingly, the amplicon of SEQ ID NO:3 comprises a forward or 5' primer associated with any one of SEQ ID NO: 2991-5492, SEQ ID NO:7, SEQ ID NO: 8, SEQ ID NO: 17, SEQ ID NO: 19 or a complement thereof. Likewise, the amplicon of SEQ ID NO:3 comprises a reverse or 3' primer associated with any one of SEQ ID NO: 2991-5492, SEQ ID NO:7, SEQ ID NO:8, SEQ ID NO: 17, SEQ ID NO: 19 or a complement thereof. In other aspects, the amplicon of SEQ ID NO:3 comprises a probe associated with any one of SEQ ID NO: 21-137 or a complement thereof. In further aspects, the amplicon of SEQ ID NO: 1 comprises a polynucleotide that shares at least 98% sequence identity with a primer associated with any one of SEQ ID NO: 489-2990, SEQ ID NO:5 SEQ ID NO:6, SEQ ID NO: 13, SEQ ID NO: 15 or a complement thereof. In other aspects, the amplicon of SEQ ID NO: 1 comprises a polynucleotide that shares at least 95%, 96%, 97%, 98%, or 99% sequence identity with a primer associated with any one of SEQ ID NO: 489-2990, SEQ ID NO:5 SEQ ID NO:6, SEQ ID NO: 13, SEQ ID NO:15 or a complement thereof. In an aspect, the amplicon of SEQ ID NO: 1 comprises a probe that shares at least 95%, 96%, 97%, 98%, or 99% sequence identity with a probe associated with any one of SEQ ID NO: 138-254 or a complement thereof. In some aspects, the amplicon of SEQ ID NO:3 comprises a polynucleotide that shares at least 98% sequence identity with a primer associated with any one of SEQ ID NO: 2991-5492, SEQ ID NO: 7, SEQ ID NO:8, SEQ ID NO: 17, SEQ ID NO: 19 or a complement thereof. In further aspects, the amplicon of SEQ ID NO:3 comprises a polynucleotide that shares at least 95%, 96%, 97%, 98%, or 99% sequence identity with a primer associated with any one SEQ ID NO: 2991-5492, SEQ ID NO:7, SEQ ID NO:8, SEQ ID NO: 17, SEQ ID NO: 19 or a complement thereof. In a further aspect, the amplicon of SEQ ID NO:3 comprises a probe that shares at least 95%, 96%, 97%, 98%, or 99% sequence identity with a probe associated with any one of SEQ ID NO: 21-137 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In another aspect, the disclosure relates to selecting a canola plant comprising an N7/N16 homoeologous chromosomal reciprocal translocation. In an aspect, the disclosure relates to genotyping at least one canola plant with respect to the N7/N16 homoeologous chromosomal reciprocal translocation, wherein the at least one canola plant comprises SEQ ID NO:255-488 or a complement thereof. In a further aspect, the disclosure relates to selecting a canola plant that includes the N7/N16 homoeologous chromosomal reciprocal translocation associated with SEQ ID NO: 255-488 or a complement thereof. In a further aspect, the disclosure relates to a PCR amplicon comprising SEQ ID NO:255-488. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In another aspect, the disclosure relates to selecting a canola plant comprising an N7/N16 homoeologous chromosomal reciprocal translocation. In an aspect, the disclosure relates to genotyping at least one canola plant with respect to the N7/N16 homoeologous chromosomal reciprocal translocation, wherein the at least one canola plant comprises SEQ ID NO:21-254 or a complement thereof. In a further aspect, the disclosure relates to selecting a canola plant that includes the N7/N16 homoeologous chromosomal reciprocal translocation associated with SEQ ID NO: 21-254 or a complement thereof. In a further aspect, the disclosure relates to a PCR amplicon comprising SEQ ID NO:21-254. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In another aspect, the disclosure relates to a PCR assay method for determining the recombinant genetic frequencies in canola plants comprising the N7/N16 homoeologous chromosomal reciprocal translocation. In some aspects, the recombinant genetic frequency of the N7/N16 homoeologous chromosomal reciprocal translocation is determined in a canola plant, tissue, or cell. In some aspects, the disclosure relates to performing a first PCR assay using a first probe, a first forward primer, and a first reverse primer on a polynucleotide from a canola plant sample. In other aspects, the disclosure relates to performing a second PCR assay using a second probe, a second forward primer, and a second reverse primer on the polynucleotide sample. In further aspects, the disclosure relates to quantifying the first probe and the second probe. In additional aspect, the disclosure relates to comparing the quantified first probe and the quantified second probe of the first PCR assay and the second PCR assay to determine the recombinant genetic frequencies, wherein the recombinant genetic frequency of the N7/N16 homoeologous chromosomal reciprocal translocation is selected from the group consisting of linked, tightly linked, or extremely tightly linked. In an aspect, the first and the second PCR assays are a multiplex PCR-format. In another aspect, the first and second PCR assays are performed in a single PCR assay tube or well. In an additional aspect, the first and the second PCR assays are a real-time PCR. In other aspects, the first probe and the second probe are quantified by measuring excitation/emission spectra emitted from the fluorescent dyes, during the amplification. In further aspects, the zygosity is determined by comparing the quantified first probe and the second probe using a $\Delta\Delta Ct$ formula.

In some aspects the disclosure relates to a PCR assay method for determining the recombinant genetic frequency of a N7/N16 homoeologous chromosomal reciprocal translocation in a canola plant, tissue, or cell, wherein PCR assay occurs within either SEQ ID NO: 2 or SEQ ID NO:4. In further aspects, the PCR assay of the N7/N16 homoeologous chromosomal reciprocal translocation into a progeny canola plant is detected by producing an amplicon of SEQ ID NO:2, wherein the amplicon comprises a primer associated with any one of SEQ ID NO:5493-8026, SEQ ID NO:9, SEQ ID NO: 10, SEQ ID NO: 14, SEQ ID NO: 16 or a complement thereof. Accordingly, the amplicon of SEQ ID NO:2 comprises a forward or 5' primer associated with any one of SEQ ID NO:5493-8026, SEQ ID NO:9, SEQ ID NO: 10, SEQ ID NO: 14, SEQ ID NO:16 or a complement thereof. Likewise, the amplicon of SEQ ID NO:2 comprises a reverse or 3' primer associated with any one of SEQ ID NO:5493-8026, SEQ ID NO: 9, SEQ ID NO: 10, SEQ ID NO: 14, SEQ ID NO: 16 or a complement thereof. In some aspects, the amplicon of SEQ ID NO:2 comprises a probe associated with any one of SEQ ID NO: 372-488 or a complement thereof. In other aspects, the PCR assay method of a N7/N16 homoeologous chromosomal reciprocal translocation in a canola plant is detected by producing an amplicon of SEQ ID NO:4, wherein the amplicon comprises a primer associated with any one of SEQ ID NO: 8027-10560, SEQ ID NO: 11, SEQ ID NO: 12, SEQ ID NO: 18, SEQ ID NO:20 or a complement thereof. Accordingly, the amplicon of SEQ ID NO:4 comprises a forward or 5' primer associated with any one of SEQ ID NO: 8027-10560, SEQ ID NO:11, SEQ ID NO:12, SEQ ID NO: 18, SEQ ID NO:20 or a complement thereof. Likewise, the amplicon of SEQ ID NO: 4 comprises a reverse or 3' primer associated with any one of SEQ ID NO: 8027-10560, SEQ ID NO:11, SEQ ID NO:12, SEQ ID NO:18, SEQ ID NO:20 or a complement thereof. In other aspects, the amplicon of SEQ ID NO:4 comprises a probe associated with any one of SEQ ID NO: 255-371 or a complement thereof. In further aspects, the amplicon of SEQ ID NO:2 comprises a polynucleotide that shares at least 98% sequence identity with a primer associated with any one of SEQ ID NO: 5493-8026, SEQ ID NO:9, SEQ ID NO: 10, SEQ ID NO: 14, SEQ ID NO: 16 or a complement thereof. In other aspects, the amplicon of SEQ ID NO:2 comprises a polynucleotide that shares at least 95%, 96%, 97%, 98%, or 99% sequence identity with a primer associated with any one of SEQ ID NO:5493-8026, SEQ ID NO:9, SEQ ID NO: 10, SEQ ID NO: 14, SEQ ID NO: 16 or a complement thereof. In an aspect, the amplicon of SEQ ID NO:2 comprises a probe that shares at least 95%, 96%, 97%, 98%, or 99% sequence identity with a probe associated with any one of SEQ ID NO:372-488 or a complement thereof. In some aspects, the amplicon of SEQ ID NO:4 comprises a polynucleotide that shares at least 98% sequence identity with a primer associated with any one of SEQ ID NO: 8027-10560, SEQ ID NO: 11, SEQ ID NO: 12, SEQ ID NO: 18, SEQ ID NO:20 or a complement thereof. In further aspects, the amplicon of SEQ ID NO:4 comprises a polynucleotide that shares at least 95%, 96%, 97%, 98%, or 99% sequence identity with a primer associated with any one SEQ ID NO: 8027-10560, SEQ ID NO:11, SEQ ID NO: 12, SEQ ID NO: 18, SEQ ID NO:20 or a complement thereof. In a further aspect, the amplicon of SEQ ID NO:4 comprises a probe that shares at least 95%, 96%, 97%, 98%, or 99% sequence identity with a probe associated with any one of SEQ ID NO: 255-371 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translocation by determining the size of said nucleic acid. In an aspect, determining the size comprises HPLC or electrophoresis.

In some aspects the disclosure relates to a PCR assay method for determining the recombinant genetic frequency of a N7/N16 homoeologous chromosomal reciprocal translocation in a canola plant, tissue, or cell, wherein the PCR assay occurs within either SEQ ID NO: 1 or SEQ ID NO:3. In further aspects, the PCR assay of the N7/N16 homoeologous chromosomal reciprocal translocation into a progeny canola plant is detected by producing an amplicon of SEQ ID NO: 1, wherein the amplicon comprises a primer associated with any one of SEQ ID NO: 489-2990, SEQ ID NO:5 SEQ ID NO:6, SEQ ID NO: 13, SEQ ID NO: 15 or a complement thereof. Accordingly, the amplicon of SEQ ID NO: 1 comprises a forward or 5' primer associated with any one of SEQ ID NO: 489-2990, SEQ ID NO:5 SEQ ID NO:6, SEQ ID NO: 13, SEQ ID NO:15 or a complement thereof. Likewise, the amplicon of SEQ ID NO: 1 comprises a reverse or 3' primer associated with any one of SEQ ID NO: 489-2990, SEQ ID NO: 5 SEQ ID NO:6, SEQ ID NO: 13, SEQ ID NO: 15 or a complement thereof. In some aspects, the amplicon of SEQ ID NO: 1 comprises a probe associated with any one of SEQ ID NO:138-254 or a complement thereof. In further aspects, the PCR assay of the N7/N16 homoeologous chromosomal reciprocal translocation into a progeny canola plant is detected by producing an amplicon of SEQ ID NO:3, wherein the amplicon comprises a primer associated with any one of SEQ ID NO: 2991-5492, SEQ ID NO:7, SEQ ID NO:8, SEQ ID NO: 17, SEQ ID NO: 19 or a complement thereof. Accordingly, the amplicon of SEQ ID NO:3 comprises a forward or 5' primer associated with any one of SEQ ID NO: 2991-5492, SEQ ID NO:7, SEQ ID NO:8, SEQ ID NO: 17, SEQ ID NO:19 or a complement thereof. Likewise, the amplicon of SEQ ID NO:3 comprises a reverse or 3' primer associated with any one of SEQ ID NO: 2991-5492, SEQ ID NO: 7, SEQ ID NO:8, SEQ ID NO: 17, SEQ ID NO: 19 or a complement thereof. In other aspects, the amplicon of SEQ ID NO:3 comprises a probe associated with any one of SEQ ID NO: 21-137 or a complement thereof. In further aspects, the amplicon of SEQ ID NO: 1 comprises a polynucleotide that shares at least 98% sequence identity with a primer associated with any one of SEQ ID NO: 489-2990, SEQ ID NO:5 SEQ ID NO:6, SEQ ID NO: 13, SEQ ID NO: 15 or a complement thereof. In other aspects, the amplicon of SEQ ID NO: 1 comprises a polynucleotide that shares at least 95%, 96%, 97%, 98%, or 99% sequence identity with a primer associated with any one of SEQ ID NO: 489-2990, SEQ ID NO:5 SEQ ID NO:6, SEQ ID NO: 13, SEQ ID NO:15 or a complement thereof. In an aspect, the amplicon of SEQ ID NO:1 comprises a probe that shares at least 95%, 96%, 97%, 98%, or 99% sequence identity with a probe associated with any one of SEQ ID NO: 138-254 or a complement thereof. In some aspects, the amplicon of SEQ ID NO:3 comprises a polynucleotide that shares at least 98% sequence identity with a primer associated with any one of SEQ ID NO: 2991-5492, SEQ ID NO: 7, SEQ ID NO:8, SEQ ID NO: 17, SEQ ID NO: 19 or a complement thereof. In further aspects, the amplicon of SEQ ID NO:3 comprises a polynucleotide that shares at least 95%, 96%, 97%, 98%, or 99% sequence identity with a primer associated with any one SEQ ID NO: 2991-5492, SEQ ID NO:7, SEQ ID NO:8, SEQ ID NO:17, SEQ ID NO: 19 or a complement thereof. In a further aspect, the amplicon of SEQ ID NO:3 comprises a probe that shares at least 95%, 96%, 97%, 98%, or 99% sequence identity with a probe associated with any one of SEQ ID NO: 21-137 or a complement thereof. In an additional aspect, the disclosure relates to quantitating the amplicon produced by an amplification reaction. In some aspects, quantitating the results of the amplification reaction comprises producing a signature profile. As such, the signature profile is selected from the group consisting of a melting temperature curve signature profile and a fluorescence signature profile. Further, the signature profile is produced from an intercalating DNA dye, a cyanine dye, or a fluorescent dye. Likewise, the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In yet a further aspect, the disclosure relates to determining the presence or absence of the N7/N16 homoeologous chromosomal reciprocal translocation by determining the nucleotide sequence of said nucleic acid. In another aspect, the disclosure relates to determining the presence or absence of the N7/N16 homoeologous chromosomal reciprocal translation by determining the size of said nucleic acid. In an aspect, determining the size comprises HPLC or electrophoresis.

The foregoing and other features will become more apparent from the following embodiments as provided in the Claims and Detailed Description, which proceeds with reference to the accompanying Figures and Sequence Listing.

SEQUENCE LISTING

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand and reverse complementary strand are understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). In the accompanying sequence listing:

The chromosomal interval of base pairs 17578019 to 17583020 of chromosome 7 from the DH12075 v1.1 genome is provided as SEQ ID NO: 1.

The chromosomal interval of base pairs 20106368 to 20111369 of chromosome 7 from the NS1822BC genome is provided as SEQ ID NO:2.

The chromosomal interval of base pairs 13651438 to 13656439 of chromosome 16 from the DH12075 v1.1 genome is provided as SEQ ID NO:3.

The chromosomal interval of base pairs 8089982 to 8094983 of chromosome 16 from the NS1822BC genome is provided as SEQ ID NO:4.

The DHN16 probe sequences are provided as SEQ ID NO: 21-137.

The DHN7 probe sequences are provided as SEQ ID NO: 138-254.

The NSN16 probe sequences are provided as SEQ ID NO: 255-371.

The NSN7 probe sequences are provided as SEQ ID NO: 372-488.

The DHN7 primer sequences are provided as SEQ ID NO: 489-2990, SEQ ID NO:5 SEQ ID NO: 6, SEQ ID NO: 13 and SEQ ID NO:15.

The DHN16 primer sequences are provided as SEQ ID NO: 2991-5492, SEQ ID NO:7, SEQ ID NO:8, SEQ ID NO:17 and SEQ ID NO: 19.

The NSN7 primer sequences are provided as SEQ ID NO: 5493-8026, SEQ ID NO:9, SEQ ID NO: 10, SEQ ID NO:14 and SEQ ID NO:16.

The NSN16 primer sequences are provided as SEQ ID NO: 8027-10560, SEQ ID NO:11, SEQ ID NO: 12, SEQ ID NO:18 and SEQ ID NO:20.

DETAILED DESCRIPTION

Development of novel methods and compositions for molecular breeding assays that can be readily applied for breeding in B. napus are of importance for B. napus breeders. Commercially viable assays that are time efficient and can provide cost saving are of particular interest. Of further importance is the ability to complete the assay in a variety of different scales. From a single Eppendorf™ tube to larger multi-well formats, the application of the assay should be readily utilized in any applied format. Methods and compositions for molecular breeding assays that can detect a N7/N16 homoeologous chromosomal reciprocal translocation in B. napus are disclosed herein. A detailed genomic characterization of the break point, the genetic/physical extent of this homoeologous chromosomal reciprocal translocation, frequency in the global elite germplasm & distribution in various heterotic pools, and linkage with traits of commercial value are provided for the first time in this disclosure.

The methods and compositions for molecular breeding assays that can detect a N7/N16 homoeologous chromosomal reciprocal translocation in B. napus of the subject disclosure provide markable improvements over the low throughput, low resolution and expensive methods (e.g., Fluorescent In Situ Hybridization (FISH), and use of low-density molecular marker systems such as RFLP and SSR, and other known methods) that are generally available for routing breeding. The presence of the N7/N16 homoeologous chromosomal reciprocal translocation in B. napus in breeding progenies results in non-parental recombinant types, characterized by segmental deletion and duplication in homoeologous regions. The methods and compositions for molecular breeding assays that can detect a N7/N16 homoeologous chromosomal reciprocal translocation in B. napus provide numerous advantages to overcome particular problems for B. napus breeding.

A particular problem for B. napus breeders is the development of an assay to detect the introgression of traits in B. napus breeding programs. Traits that are bred into proximity of the N7/N16 homoeologous chromosomal reciprocal translocation in B. napus can be introduced into new lines of B. napus germplasm through the translocation of the N7/N16 homoeologous chromosomal. Either native traits or transgenic traits may be bred into loci within the chromosomal regions of either the N7 or N16 chromosome. Relying upon the translocation mechanism within specific lines of B. napus allows for the introgression of the trait into a new line of B. napus. As such, the methods and compositions for molecular breeding assays that can detect a N7/N16 homoeologous chromosomal reciprocal translocation in B. napus provide a solution for introgressing traits within B. napus.

A particular problem for B. napus breeders is the development of an assay to detect heterosis in B. napus breeding programs. The identification of "parental type" classes of B. napus lines among the breeding progenies that have been identified to segregate for N7/N16 homoeologous chromosomal reciprocal translocation in B. napus have heterotic advantage. Currently, there is no ability to detect and enrich/discard these variants leading to loss of cost and time efficiencies in breeding. As such, the methods and compositions for molecular breeding assays that can detect a N7/N16 homoeologous chromosomal reciprocal translocation in B. napus provide a solution for detecting heterosis within B. napus.

A particular problem for B. napus breeders is the development of an assay for signal detection in B. napus breeding programs. Typical commercial scale "signal detection" methods rely on a single reference genetic map and marker order, by-passing the construction of de novo population specific genetic map for signal detection. If a large homoeologous chromosomal reciprocal translocation, such as N7/N16, are differentially distributed/fixed in the heterotic pools, and the mapping populations are segregating for N7/N16 homoeologous chromosomal reciprocal translocation, then such signal detection assays could lead to inaccurate assignments of quantitative trait loci and genes present on these chromosomes, directly impacting marker driven forward and backcross breeding selections. As such, the methods and compositions for molecular breeding assays that can detect a N7/N16 homoeologous chromosomal reciprocal translocation in *B. napus* provide a solution for detecting the N7/N16 homoeologous chromosomal reciprocal translocation within *B. napus*.

Novel methods have now been disclosed for detecting the N7/N16 homoeologous chromosomal reciprocal translocations in *B. napus*. The disclosed methods can be deployed as high throughput assays allowing for the rapid and efficient identification of a subset of samples that can then be further processed through traditional plant breeding methodologies. The disclosed assays describe high quality, high throughput processes for identifying and obtaining the N7/N16 homoeologous chromosomal reciprocal translocations in *B. napus*.

Definitions

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises", "comprising", "includes", "including", "has", "having", "contains"," or "containing", or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of an embodiment of the disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques were designed primarily for this sorting out.

As used herein, the term "polymerase chain reaction" and "PCR" generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified.

Term "amplicon" refers to as natural or manually amplification event (for example, polymerase chain reaction) product formation Polynucleotides (for example, DNA) segment. In some embodiments, amplicon is "length" amplicon, and the length is at least 5 kb, or At least 6 kb, 7 kb, 8 kb, 9 kb, 10 kb, 11 kb, 12 kb, 13 kb, 14 kb, 15 kb, 16 kb, 17 kb, 18 kb, 19 kb, or 20 kb.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence has been introduced into a host cell by genetic engineering (or the progeny thereof) where the transgene/ heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/ heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

A "gene product" as defined herein is any product produced by the gene. For example, the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, New York, 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions: Very High Stringency: Hybridization in 5×SSC buffer at 65° C. for 16 hours; was twice in 2×SSC buffer at room temperature for 15 minutes each; and wash twice in 0.5×SSC buffer at 65° C. for 20 minutes each. High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each. Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query") polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present disclosure is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the disclosure, function of a query polypeptide is inferred from function of a conserved protein sequence where either (1) hit_p<1e-30 or % identity >35% AND query_coverage >50% AND hit_coverage >50%, or (2) hit_p<1e-8 AND query_coverage >70% AND hit_coverage >70%.

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, CA). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ (©1993-2016). DNASTAR. Madison, WI). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. December 15; 73(1):237-44; Higgins and Sharp (1989) CABIOS 5:151-3; Higgins et al. (1992) Comput. Appl. Biosci. 8:189-91). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) J. Mol. Biol. 215:403-10). Further examples of such BLAST alignment programs include Gapped-BLAST or PSI-BLAST (Altschul et al., 1997). In an embodiment, the subject disclosure relates to calculating percent identity between two polynucleotides or amino acid sequences using the EMBOSS suite of alignment programs, including, but not limited to: Matcher, Needle, Stretcher, Water, Word-match, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics,* 2:482-489, 1981, Smith et al., Nucleic Acids Research 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the disclosure will have at least about 40%, 45%, 50%>, 55%, 60%, 65%, 70%, 75%, 80%, 85%, 90%, 91%, 92%, 93%, 94%, 95%, 96%, 97%, 98% 0, 99% or more sequence identity to that particular nucleotide sequence as determined by sequence alignment programs and parameters described elsewhere herein. A biologically active variant of a nucleotide sequence of the disclosure may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "regeneration" means the process of growing a plant from a plant cell (e.g., plant protoplast or explant).

As used herein, the term "culturing" refers to the in vitro propagation of cells or organisms on or in media of various kinds so that the maintenance or growth cell within a liquid culture medium are controlled under a set of physical conditions. It is understood that the descendants of a cell grown in culture may not be completely identical (i.e., morphologically, genetically, or phenotypically) to the parent cell.

As used herein, the term "co-expressing" refers to two or more gene products which are produced at the same time within the same host organism.

As used herein, the term "degenerate" refers to a primer or probe nucleic acid in which certain positions are not defined by a single, specific nucleotide. Thus, in such a degenerate position, the primer or probe sequence can be either one of at least two different nucleotides. Such positions often represent difference in genotypes of the target nucleic acid. A degenerate sequence may also be represented as a mixture of multiple non-degenerate individual sequences which, for the purpose of this disclosure, differ in at least two positions.

As used herein, the term "expression" refers to the combination of intracellular processes, including transcription and translation undergone by a coding DNA molecule such as a structural gene to produce a polypeptide.

As used herein, the term "transgenic cell" means any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

As used herein, the term "transgenic plant" means a plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is typically a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present disclosure is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "linkage disequilibrium" refers to a statistical association between two loci or between a trait and a marker.

As used herein, linkage between genes or markers refers to the phenomenon in which genes or markers on a chromosome show a measurable probability of being passed on together to individuals in the next generation. The closer two genes or markers are to each other, the closer to (1) this probability becomes Thus, the term "linked" may refer to one or more genes or markers that are passed together with a gene with a probability greater than 0.5 (which is expected from independent assortment where markers/genes are located on different chromosomes) Because the proximity of two genes or markers on a chromosome is directly related to the probability that the genes or markers will be passed together to individuals in the next generation, the term "linked" may also refer herein to one or more genes or markers that are located within about 2.0 Mb of one another on the same *Brassica* spp. chromosome. Thus, two "linked" genes or markers may be separated by about 2.1 Mb, 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb, about 1.05 Mb, about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb: about 0.25 Mb: about 0.20 Mb; about 0.15 Mb; about 0.10 Mb; about 0.05 Mb; about 0.025 Mb; about 0.012 Mb; and about 0.01 Mb. A gene may be "linked" to a marker that resides within an exon or intron of the gene. In this case, the separation between the linked gene and marker is 0.00 Mb.

Markers and/or genes may also be "linked" to a phenotype, for example, a phenotype in which the linked gene or gene linked to the linked marker is involved. As will be understood by those of skill in the art, the length of this marker will vary if nucleotides are added or subtracted from the span of genomic DNA located between the distal ends of the particular primers used when annealed.

As used herein, the term "tightly linked" may refer to one or more genes or markers that are located within about 0.5 Mb of one another on the same chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.12 Mb; about 0.1 Mb, about 0.05 Mb, and about 0.00 Mb.

As used herein, the term "extremely tightly linked" may refer to one or more genes or markers that are located within about 100 kb of one another on the same chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb, about 30 kb, about 25 kb; about 20 kb; about 15 kb; about 12 kb; about 10 kb; about 5 kb; about 1 kb, and about 0 kb.

Linked, tightly linked, and extremely tightly genetic markers may be useful in marker-assisted breeding programs to identify individuals comprising linked phenotypes and/or gene types, and to breed these traits and/or genes into *Brassica* varieties.

Additional markers can be identified as equivalent to this exemplary marker, for example, by determining the frequency of recombination between the additional marker and the exemplary SSR marker Such determinations may utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in any cultivar, then the additional marker is considered equivalent to the particular reference marker for the purposes of use in the presently disclosed methods.

As used herein, the term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum) "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

The term "zygosity" means determining whether the source of nucleic acid appears heterozygous, homozygous, or hemizygous.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hemizygous" means having an allele of a gene at a given locus on one chromosome in the diploid state, for which there is no corresponding locus on the other chromosome of the pair.

As used herein, the term "introgression" refers to a genomic segment that has moved from one individual, species, variety or cultivar into the genome of another individual, species, variety or cultivar, by crossing those individuals, species, varieties or cultivars.

As used herein, the terms "introgressing", "introgress" and "introgressed" refer to both a natural and artificial process whereby individual genes or entire traits are moved from one individual, species, variety or cultivar into the genome of another species, variety or cultivar, by crossing those species, varieties or cultivars. In plant breeding, the process usually involves selfing or backcrossing to the recurrent parent to provide for an increasingly homozygous plant having essentially the characteristics of the recurrent parent in addition to the introgressed gene or trait.

The term "backcross" refers to the process wherein the plant resulting from a cross between two parental lines is crossed with one of its parental lines, wherein the parental line used in the backcross is referred to as the recurrent parent. Repeated backcrossing results in the genome becoming more and more homozygous or inbred.

The term "selfing" refers to the process of self-fertilization wherein an individual is pollinated or fertilized with its own pollen.

Unless otherwise specifically explained, all technical and scientific terms used herein have the same meaning as commonly understood by those of ordinary skill in the art to which this disclosure belongs. Definitions of common terms in molecular biology can be found in, for example: Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

EMBODIMENTS

A plant cell, callus, tissue or plant may be identified and isolated by selecting or screening the plant material for the N7/N16 homoeologous chromosomal reciprocal translocations in *B. napus*. Various assays can be employed to detect the polynucleotides that comprise the N7/N16 homoeologous chromosomal reciprocal translocations in *B. napus*. The following techniques are useful in a variety of situations, and in one embodiment, are useful in detecting the presence or absence of the N7/N16 homoeologous chromosomal reciprocal translocations in *B. napus*. For example, the presence of the molecule can be determined in a variety of ways, including using a primer or probe of the sequence in an amplification reaction. In an embodiment the disclosure relates method of detecting a plant comprising the N7/N16 homoeologous chromosomal reciprocal translocations in *B. napus* via an amplification reaction in which an amplified product or amplicon is generated. The detection of the amplicon is an indication of whether the plant contains the N7/N16 homoeologous chromosomal reciprocal translocations in *B. napus.*

Amplification of a nucleic acid sequence may be carried out by any suitable methodologies. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "35R") (see J. Guatelli et al., Proc. Natl. Acad. Sci. USA 87, 1874-1878 (1990)), the QB replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

The polynucleotides that comprise the N7/N16 homoeologous chromosomal reciprocal translocations in *B. napus,* or segments thereof, can be used as primers and/or probes for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject disclosure. Mutations, insertions, and deletions can be produced in a given primer by methods known to an ordinarily skilled artisan.

As such, the chromosomal interval of: base pairs 17578019 to 17583020 of chromosome 7 from the DH12075 v1.1 genome is provided as SEQ ID NO: 1; of base pairs 20106368 to 20111369 of chromosome 7 from the NS1822BC genome is provided as SEQ ID NO: 2; of base pairs 13651438 to 13656439 of chromosome 16 from the DH12075 v1.1 genome is provided as SEQ ID NO:3; and, of base pairs 8089982 to 8094983 of chromosome 16 from the NS1822BC genome is provided as SEQ ID NO:4. In addition, probe sequences are provided herein: DHN16 probe sequences are provided as SEQ ID NO: 21-137; DHN7 probe sequences are provided as SEQ ID NO: 138-254; NSN16 probe sequences are provided as SEQ ID NO: 255-371; NSN7 probe sequences are provided as SEQ ID NO: 372-488. In addition, primer sequences are provided herein: DHN7 primer sequences are provided as SEQ ID NO: 489-2990, SEQ ID NO:5 SEQ ID NO:6, SEQ ID NO:13 and SEQ ID NO: 15; DHN16 primer sequences are provided as SEQ ID NO: 2991-5492, SEQ ID NO:7, SEQ ID NO:8, SEQ ID NO: 17 and SEQ ID NO: 19; NSN7 primer sequences are provided as SEQ ID NO: 5493-8026, SEQ ID NO:9, SEQ ID NO: 10, SEQ ID NO: 14 and SEQ ID NO:16; and, NSN16 primer sequences are provided as SEQ ID NO: 8027-10560, SEQ ID NO:11, SEQ ID NO:12, SEQ ID NO:18 and SEQ ID NO:20. These sequences provide exemplified compositions that can be used in an amplification reaction. Those with skill in the art could utilize the primer and probe sequences as disclosed to amplify a fragment of the genomic sequences and to detect the resulting amplicon.

In some embodiments an amplicon can be detected. In an aspect of this embodiment the amplicon is detected on an agarose gel via electrophoresis. Those with skill in the art appreciate the various types of agarose gel electrophoresis reagents and techniques that may be used. For instance pulsed field gel electrophoresis, pulsed orthogonal gel electrophoresis agarose multigel electrophoresis, and traditional agarose gel electrophoresis can be used with the subject disclosure. In further embodiments the size of the amplicon can be detected to determine whether the assay for the N7/N16 homoeologous chromosomal reciprocal translocations in *B. napus.* In an aspect the size of the amplicon can be about 50 base pairs, 100 base pairs, 150 base pairs, 200 base pairs, 250 base pairs, 300 base pairs, 350 base pairs, 400 base pairs, 450 base pairs, 500 base pairs, 550 base pairs, 600 base pairs, 650 base pairs, 700 base pairs, 750 base pairs, 800 base pairs, 850 base pairs, 900 base pairs, 950 base pairs, 1 kilobase pairs, 2 kilobase pairs, 3 kilobase pairs, 4 kilobase pairs, 5 kilobase pairs, 6 kilobase pairs, 7 kilobase pairs, 8 kilobase pairs, 9 kilobase pairs, 10 kilobase pairs, 11 kilobase pairs, 12 kilobase pairs, 13 kilobase pairs, 14 kilobase pairs, 15 kilobase pairs, 16 kilobase pairs, 17 kilobase pairs, 18 kilobase pairs, 19 kilobase pairs, or 20 kilobase pairs.

Following the completion of the PCR reaction and probe detection, a table and distribution graph may be generated using, for example, any suitable computer graphics software. Results obtained with wild-type, hemizygous and homozygous DNA of similar and/or known genotypic backgrounds may serve as positive or negative controls. In a segregating population, three clusters of data points may be obtained, allowing the visual determination of a sample result as likely belonging to one of the segregated clusters. Alternatively, data analysis computer software may be used to calculate the probability that a sample result belongs to each segregated cluster, with the most probable cluster serving as the sample designation. When a visual determination is made, the boundary of each cluster may be arbitrary, for example, when three clusters of data points are clearly visible.

Raw fluorescence intensity data may also be analyzed directly from a plate reader using a suitable analysis package, such as KLIMS (KBioscience laboratory information management system). A graph with the relative fluorescence units (RFU) of a fluorescence signal generated by a specific probe for a mutant allele plotted on one axis, and the RFU of a fluorescence signal generated by a specific probe for the wild-type allele plotted on the other axis may be generated. Zygosity determinations may then be made based on the cluster separation in a graphical display of the data.

Samples that do not contain the N7/N16 homoeologous chromosomal reciprocal translocation in a *B. napus* may only result in fluorescence readings of the wild-type PCR product. Samples containing hemizygous or homozygous mutant genomic DNA may result in RFU readings for the mutant-specific probe higher than that of a negative background control. If a sample yields no adequate results, the genomic DNA in the sample may not be of adequate quality and/or quantity, and a new DNA preparation and/or new PCR reaction should be performed. Preferably, a negative control sample containing no DNA sample shows very low detection of gene-specific probe(s). It is also preferable that known homozygous controls show only high detection of the mutant or wild-type DNA in the control, and that known hemizygous controls show both high detection of the mutant and wild-type DNA.

In an embodiment, the amplification reaction is quantified. In other embodiments, the amplification reaction is quantitated using a signature profile, in which the signature profile is selected from the group consisting of a melting temperature or a fluorescence signature profile. In some embodiments the amplification reaction is quantitated via the Delta Delta ct method. In other embodiments the amplification reaction is quantitated via the comparative cycle threshold method. In further embodiments the amplification reaction is quantitated via the standard curve method.

Standard Curve. Nucleic acids can be used to establish a standard curve. These methods are well known and include internal controls, double stranded DNA, a cDNA expressing a target gene, or an in vitro generated single stranded DNA. Methods may vary according to the nucleic acid chosen to serve as the standard to establish a standard curve.

Comparative Cycle Threshold. The comparative cycle threshold (Ct) method, also known as the $2^{-\Delta\Delta Ct}$ method, is also used to quantify DNA levels. The Ct method compares a test reaction with a control or calibrator sample. The Ct values of both the control/calibrator sample and the test sample are normalized. In an embodiment of the invention, the Ct values were normalized to an arbitrary cutoff, 20-22. In another embodiment, the Ct values were normalized to within 1 Ct value of a negative control (a sample with no inhibition). This allows for the sensitivity of the assay and proper dynamic range.

Ct Method. The Ct method can also be described by the $\Delta\Delta Ct$ formula; $\Delta\Delta Ct = \Delta Ct_{test}$ sample-$\Delta Ct_{reference\ sample}$. The amplification efficiencies of the test sample and the reference sample must be about the same for the formula to operate. Amplification efficiencies can be determined by a comparison of the samples with template dilution. The amplification efficiency is about the same when a plot of cDNA dilution versus $\Delta Ct$ approximates zero.

DNA may be isolated (for example, extracted, and purified) from plant tissue by methods known to those of skill in the art. Commercial kits for DNA isolation are available, for example, from Qiagen, Inc. In some embodiments, leaf discs from a particular plant are punched and transferred into collection tubes. The puncher may be cleaned after each sampling with 70% alcohol, rinsing in water, and drying. DNA extraction buffers may be prepared according to the manufacturer's recommendations. DNA may then be isolated using the kit according to the manufacturer's instructions. Finally, the concentration of the isolated DNA may be determined using, for example, a Quant-iT™ PicoGreen® Quantfication Kit (Invitrogen, Carlsbad, Calif.) and a spectrophotometer, or by any other suitable technique.

In further embodiments, the compositions and methods of the subject disclosure may be used to design novel primer and probe sequences to the chromosomal interval of base pairs 17578019 to 17583020 of chromosome 7 from the DH12075 v1.1 genome is provided as SEQ ID NO: 1. Those with skill in the art could utilize the disclosure to design primers of about 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs 24 base pairs, 25 base pairs, 26 base pairs, 27 base pairs, 28 base pairs, 29 base pairs, 30 base pairs or more that can bind this polynucleotide sequence (e.g. SEQ ID NO:1). The primers that can be designed to bind the sequence could either be directly complementary to the sequence or the reverse complement of the sequence. Likewise, those with skill in the art could utilize the disclosure to design probes of about 12 base pairs, 13 base pairs, 14 base pairs, 15 base pairs, 16 base pairs, 17 base pairs, 18 base pairs, 19 base pairs, 20 base pairs, or more that can bind this polynucleotide sequence (e.g. SEQ ID NO:1). The probes that can be designed to bind the sequence could either be directly complementary to the sequence or the reverse complement of the sequence. Exemplary DHN7 primer sequences are provided as SEQ ID NO: 489-2990, SEQ ID NO:5 SEQ ID NO:6, SEQ ID NO: 13 and SEQ ID NO:15. Exemplary DHN7 probe sequences are provided as SEQ ID NO: 138-254. Those with skill in the art would be able to design and produce such compositions given that the chromosomal interval of base pairs 17578019 to 17583020 of chromosome 7 from the DH12075 v1.1 genome is provided as SEQ ID NO: 1 is disclosed herein.

In further embodiments, the compositions and methods of the subject disclosure may be used to design novel primer and probe sequences to the chromosomal interval of base pairs 20106368 to 20111369 of chromosome 7 from the NS1822BC genome is provided as SEQ ID NO: 2. Those with skill in the art could utilize the disclosure to design primers of about 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs 24 base pairs, 25 base pairs, 26 base pairs, 27 base pairs, 28 base pairs, 29 base pairs, 30 base pairs or more that can bind this polynucleotide sequence (e.g. SEQ ID NO:2). The primers that can be designed to bind the sequence could either be directly complementary to the sequence or the reverse complement of the sequence. Likewise, those with skill in the art could utilize the disclosure to design probes of about 12 base pairs, 13 base pairs, 14 base pairs, 15 base pairs, 16 base pairs, 17 base pairs, 18 base pairs, 19 base pairs, 20 base pairs, or more that can bind this polynucleotide sequence (e.g. SEQ ID NO:2). The probes that can be designed to bind the sequence could either be directly complementary to the sequence or the reverse complement of the sequence. Exemplary NSN7 primer sequences are provided as SEQ ID NO: 5493-8026, SEQ ID NO:9, SEQ ID NO:10, SEQ ID NO: 14 and SEQ ID NO:16. Exemplary NSN7 probe sequences are provided as SEQ ID NO: 372-488. Those with skill in the art would be able to design and produce such compositions given that the chromosomal interval of base pairs 20106368 to 20111369 of chromosome 7 from the NS1822BC genome is provided as SEQ ID NO:2 is disclosed herein.

In further embodiments, the compositions and methods of the subject disclosure may be used to design novel primer and probe sequences to the chromosomal interval of base pairs 13651438 to 13656439 of chromosome 16 from the DH12075 v1.1 genome is provided as SEQ ID NO: 3. Those with skill in the art could utilize the disclosure to design primers of about 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs 24 base pairs, 25 base pairs, 26 base pairs, 27 base pairs, 28 base pairs, 29 base pairs, 30 base pairs or more that can bind this polynucleotide sequence (e.g. SEQ ID NO:3). The primers that can be designed to bind the sequence could either be directly complementary to the sequence or the reverse complement of the sequence. Likewise, those with skill in the art could utilize the disclosure to design probes of about 12 base pairs, 13 base pairs, 14 base pairs, 15 base pairs, 16 base pairs, 17 base pairs, 18 base pairs, 19 base pairs, 20 base pairs, or more that can bind this polynucleotide sequence (e.g. SEQ ID NO:3). The probes that can be designed to bind the sequence could either be directly complementary to the sequence or the reverse complement of the sequence. Exemplary DHN16 primer sequences are provided as SEQ ID NO: 2991-5492, SEQ ID NO:7, SEQ ID NO:8, SEQ ID NO: 17 and SEQ ID NO:19. Exemplary DHN16 probe sequences are provided as SEQ ID NO: 21-137. Those with skill in the art would be able to design and produce such compositions given that the chromosomal interval of base pairs 13651438 to 13656439 of chromosome 16 from the DH12075 v1.1 genome is provided as SEQ ID NO:3 is disclosed herein.

In further embodiments, the compositions and methods of the subject disclosure may be used to design novel primer and probe sequences to the chromosomal interval of base pairs base pairs 8089982 to 8094983 of chromosome 16 from the NS1822BC genome is provided as SEQ ID NO: 4. Those with skill in the art could utilize the disclosure to design primers of about 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs 24 base pairs, 25 base pairs, 26 base pairs, 27 base pairs, 28 base pairs, 29 base pairs, 30 base pairs or more that can bind this polynucleotide sequence (e.g. SEQ ID NO:4). The primers that can be designed to bind the sequence could either be directly complementary to the sequence or the reverse complement of the sequence. Likewise, those with skill in the art could utilize the disclosure to design probes of about 12 base pairs, 13 base pairs, 14 base pairs, 15 base pairs, 16 base pairs, 17 base pairs, 18 base pairs, 19 base pairs, 20 base pairs, or more that can bind this polynucleotide sequence (e.g. SEQ ID NO:4). The probes that can be designed to bind the sequence could either be directly complementary to the sequence or the reverse complement of the sequence. Exemplary NSN16 primer sequences are provided as SEQ ID NO: 8027-10560, SEQ ID NO:11, SEQ ID NO:12, SEQ ID NO:18 and SEQ ID NO:20. Exemplary NSN16 probe sequences are provided as SEQ ID NO: 255-371. Those with skill in the art would be able to design and produce such a compositions given that the chromosomal interval of base pairs 8089982 to 8094983 of chromosome 16 from the NS1822BC genome is provided as SEQ ID NO:4 is disclosed herein.

In other embodiments, compositions and methods of the subject disclosure may be used in specific amplification assays such an end-point amplification assay to the N7/N16 homoeologous chromosomal reciprocal translocation. For example, an end-point PCR assay for testing the zygosity of *B. napus* containing the N7/N16 homoeologous chromo-somal reciprocal translocations has been developed. In an embodiment, a method for determining the zygosity of the N7/N16 homoeologous chromosomal reciprocal transloca-tions gene in a *B. napus* plant includes an amplification assay. Such an amplification or PCR assay can be quantita-tive and/or real-time and/or in a multiplex format. In an embodiment, a method employs TaqMan®-style probes (dual-labeled probes to fluoresce upon 5'→3' exonuclease activity). In an embodiment, a method employs TaqMan®-style probes and oligonucleotides that selectively hybridize to the N7/N16 homoeologous chromosomal reciprocal translocation. In an embodiment, the N7/N16 homoeologous chromosomal reciprocal translocationprobes can be coupled to a detectable label at the 5' end of the oligonucleotide. In an embodiment, the oligonucleotide can also be coupled to a quencher moiety at the 3' end. An example of a quencher moiety for the N7/N16 homoeologous chromosomal recip-rocal translocation is Black Hole Quencher™ (Biosearch Technologies, Novato, Calif.). Suitable instrumentation will thereby detect the fluorescence produced from the cleavage of the oligonucleotide probe by the nuclease activity of the DNA polymerase during replication. Analysis software then determines the quantity of amplification product based upon the fluorescence data.

In an embodiment, an end-point method for the N7/N16 homoeologous chromosomal reciprocal translocation in a *B. napus* includes; a) performing a first PCR assay using a first probe, a first forward primer, and a first reverse primer on a polynucleotide sample from *B. napus*; b) quantifying the first probes; and c) confirming that the N7/N16 homoeolo-gous chromosomal reciprocal translocation occurred within the *B. napus* genome. In an embodiment, the probes are detectably labeled. In an embodiment, the primers and probes are specific for the N7/N16 homoeologous chromo-somal reciprocal translocation in a *B. napus*. In an embodi-ment probe sequences are provided herein: DHN16 probe sequences are provided as SEQ ID NO: 21-137; DHN7 probe sequences are provided as SEQ ID NO: 138-254; NSN16 probe sequences are provided as SEQ ID NO: 255-371; NSN7 probe sequences are provided as SEQ ID NO: 372-488. In an embodiment primer sequences are provided herein: DHN7 primer sequences are provided as SEQ ID NO: 489-2990, SEQ ID NO:5 SEQ ID NO:6, SEQ ID NO: 13 and SEQ ID NO: 15; DHN16 primer sequences are provided as SEQ ID NO: 2991-5492, SEQ ID NO:7, SEQ ID NO: 8, SEQ ID NO: 17 and SEQ ID NO: 19; NSN7 primer sequences are provided as SEQ ID NO: 5493-8026, SEQ ID NO:9, SEQ ID NO: 10, SEQ ID NO: 14 and SEQ ID NO: 16; and, NSN16 primer sequences are provided as SEQ ID NO: 8027-10560, SEQ ID NO:11, SEQ ID NO: 12, SEQ ID NO:18 and SEQ ID NO:20. In an additional embodiment the N7/N16 homoeologous chromosomal reciprocal translocation is linked to the associated trait (native or transgenic) at a distance of about 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilo-base pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs.

In some embodiments the fluorescent signal or fluorescent dye is selected from the group consisting of a HEX fluo-rescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. These fluorescent signals or fluorescent dyes provide exem-plified compositions that can be used in an amplification reaction.

In other embodiments the quencher is selected from the group consisting of a Dabcyl quencher, a Tamra quencher, a Qx1 quencher, an Iowa Black FQ quencher, an Iowa Black RQ quencher, an IR Dye QC-1 quencher, a Minor Groove Binding quencher, or a Blackhole quencher. These quench-ers provide exemplified compositions that can be used in an amplification reaction.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 μM, less than 4 μM, or less than 2.7 μM. These dyes provide exemplified compositions that can be used in an amplification reaction.

Target-specific primers and probes may be labeled, for example, with fluorescent dyes (e.g., FAM, VIC, and MGBNFQ), which may allow rapid quantification of a target-specific fluorescent signal. PCR products may be measured after a pre-determined number of cycles, for example, when the reaction is in the early exponential phase.

In some embodiments, a label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a Bodipy® dye (e.g., FL, 530/ 550, TR, TMR, etc.), an Alexa Fluor® dye (e.g., 488, 532, 546, 568, 594, 555, 653, 647, 660, 680, etc.), a dichlororho-damine dye, an energy transfer dye (e.g., Bigdye®. v 1 dyes, Bigdye® v 2 dyes, Bigdye® v 3 dyes, etc.), Lucifer dyes (e.g., Lucifer yellow, etc.), Cascade Blue®, Oregon Green®, and the like. Fluorescent dyes can be distinguished and measured during amplification by their emitted excitation and/or emission spectra.

In an embodiment, a PCR assay method can include loading a PCR reaction mixture in a PCR assay tube, wherein the PCR reaction mixture comprises a polymerase with 5' to 3' nuclease activity, deoxynucleotides, a buffer, a first and a second forward primer, a first and a second reverse primer, a first and a second probe, and a polynucle-otide sample, and wherein the first probe and the second probe comprise fluorescent dyes with distinguishable exci-tation/emission spectra; and performing an amplification step(s) under amplification conditions such that the 5' to 3' nuclease activity of the polymerase cleaves the first and second probes, thereby releasing fluorescent dyes compris-ing distinguishable excitation/emission spectra.

Compositions and methods of the subject disclosure may be used in specific amplification assays such as a zygosity assay. For example, an end-point PCR assay for testing the zygosity of B. napus containing the N7/N16 homoeologous chromosomal reciprocal translocations has been developed. This assay enables large scale and high throughput screening of B. napus germplasms with the N7/N16 homoeologous chromosomal reciprocal translocations. This assay will also increase the scale of using N7/N16 homoeologous chromo-somal reciprocal translocations system for the development of B. napus lines.

In an embodiment, a method for determining zygosity of N7/N16 homoeologous chromosomal reciprocal transloca-tion in a B. napus includes; a) performing a first PCR assay using a first probe, a first forward primer, and a first reverse primer on a polynucleotide sample from B. napus; b) per-forming a second PCR assay using a second probe, a second forward primer, and a second reverse primer on the poly-nucleotide sample from B. napus; c) quantifying the first and second probes; and d) comparing the quantified first and second probes to determine zygosity. In an embodiment, the probes are detectably labeled. In an embodiment, the prim-ers and probes are specific for the N7/N16 homoeologous chromosomal reciprocal translocation in a B. napus. In an embodiment probe sequences are provided herein: DHN16 probe sequences are provided as SEQ ID NO: 21-137; DHN7 probe sequences are provided as SEQ ID NO: 138-254; NSN16 probe sequences are provided as SEQ ID NO: 255-371; NSN7 probe sequences are provided as SEQ ID NO: 372-488. In an embodiment primer sequences are provided herein: DHN7 primer sequences are provided as SEQ ID NO: 489-2990, SEQ ID NO:5 SEQ ID NO:6, SEQ ID NO:13 and SEQ ID NO:15; DHN16 primer sequences are provided as SEQ ID NO: 2991-5492, SEQ ID NO:7, SEQ ID NO:8, SEQ ID NO: 17 and SEQ ID NO: 19; NSN7 primer sequences are provided as SEQ ID NO: 5493-8026, SEQ ID NO:9, SEQ ID NO: 10, SEQ ID NO: 14 and SEQ ID NO:16; and, NSN16 primer sequences are provided as SEQ ID NO: 8027-10560, SEQ ID NO: 11, SEQ ID NO: 12, SEQ ID NO: 18 and SEQ ID NO:20.

Compositions and methods of the subject disclosure may be used in specific amplification assays such an assay to detect trait introgression resulting from the N7/N16 homoe-ologous chromosomal reciprocal translocation. For example, an end-point PCR assay for testing the zygosity of B. napus containing the N7/N16 homoeologous chromo-somal reciprocal translocations has been developed. This assay enables large scale and high throughput screening of B. napus germplasms with the N7/N16 homoeologous chro-mosomal reciprocal translocations. This assay will also increase the scale of using N7/N16 homoeologous chromo-somal reciprocal translocations system for the development of B. napus lines. Through the detection of the N7/N16 homoeologous chromosomal reciprocal translocation any associated trait (native or transgenic) that is within about 1 megabase pairs, 950 kilobase pairs, 900 kilobase pairs, 850 kilobase pairs, 800 kilobase pairs, 750 kilobase pairs, 700 kilobase pairs, 650 kilobase pairs, 600 kilobase pairs, 550 kilobase pairs, 500 kilobase pairs, 450 kilobase pairs, 400 kilobase pairs, 350 kilobase pairs, 300 kilobase pairs, 250 kilobase pairs, 200 kilobase pairs, 150 kilobase pairs, 100 kilobase pairs, 90 kilobase pairs, 80 kilobase pairs, 70 kilobase pairs, 60 kilobase pairs, 50 kilobase pairs, 40 kilobase pairs, 30 kilobase pairs, 20 kilobase pairs, 10 kilobase pairs, 9 kilobase pairs, 8 kilobase pairs, 7 kilobase pairs, 6 kilobase pairs, 5 kilobase pairs, 4 kilobase pairs, 3 kilobase pairs, 2 kilobase pairs, 1 kilobase pairs, 750 base pairs, or 500 base pairs can be detected by the assay. Those with skill in the art, would appreciate that a linked trait will remain linked to the N7/N16 chromosomal regions after the resulting translocation, and that an assay to detect the N7/N16 chromosomal regions as they are translocated within the B. napus genome will indicate the presence of any linked trait. Especially, wherein the breakage point of the N7/N16 chromosomal translocation is identified as provided within this disclosure.

Traits For Introgression

In some embodiments the assay to detect the N7/N16 homoeologous chromosomal reciprocal translocation in B. napus can be used to detect the introgression of traits (native and transgenic) via B. napus breeding programs.

Native traits of interest may be detected with the N7/N16 homoeologous chromosomal reciprocal translocation in B. napus assay of the subject disclosure. Exemplary native traits of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the N7/N16 homoeologous chromosomal locus in B. napus is further stacked with at least one other native trait coding sequence encoding a gene product con-ferring insecticidal resistance, herbicide tolerance, small RNA expression, nitrogen use efficiency, water use effi-ciency, or nutritional quality.

Native traits of interest can include genes and traits f the seeds may be evaluated using techniques such as Near Infrared Reflectance Spectroscopy.

Transgenes of interest may be detected with the N7/N16 homoeologous chromosomal reciprocal translocation in *B. napus* assay of the subject disclosure. Exemplary transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the N7/N16 homoeologous chromosomal locus in *B. napus* is further stacked with at least one other transgene/heterologous coding sequence encoding a selectable marker or a gene product conferring insecticidal resistance, herbicide tolerance, small RNA expression, nitrogen use efficiency, water use efficiency, or nutritional quality.

1. Insect Resistance

Various insect resistance genes can be further stacked with the N7/N16 homoeologous chromosomal locus in *B. napus*. The N7/N16 homoeologous chromosomal locus in *B. napus* can be operably linked with at least one other gene expression cassette containing an insect resistance gene. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab (truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be can be further stacked with the N7/N16 homoeologous chromosomal locus in *B. napus*. The N7/N16 homoeologous chromosomal locus in *B. napus* can be operably linked with at least one other gene expression cassette containing a herbicide tolerance gene. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr 1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be further stacked with the N7/N16 homoeologous chromosomal locus in *B. napus*. The N7/N16 homoeologous chromosomal locus in *B. napus* can be operably linked with at least one other gene expression cassette containing an agronomic trait gene. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be can be further stacked with the N7/N16 homoeologous chromosomal locus in *B. napus*. The N7/N16 homoeologous chromosomal locus in *B. napus* can be operably linked with at least one other gene expression cassette containing a DNA binding gene. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be can be further stacked with N7/N16 homoeologous chromosomal locus in *B. napus*. The N7/N16 homoeologous chromosomal locus in *B. napus* can be operably linked with at least one other gene expression cassette containing a small RNA sequence. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pRI small RNA (degrades RI transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be can be further stacked with the N7/N16 homoeologous chromosomal locus in *B. napus*. The N7/N16 homoeologous chromosomal locus in *B. napus* can be operably linked with at least one other gene expression cassette containing a reporter gene. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), 8-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/ streptinomycin resistance (AAD), and hygromycin phos- photransferase (HPT or HGR) as well as genes conferring resistance to herbicidal compounds. Herbicide resistance genes generally code for a modified target protein insensi- tive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bro- moxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbi- cides.

In an embodiment, herbicides can inhibit the growing point or meristem, including imidazolinone or sulfonylurea, and genes for resistance/tolerance of acetohydroxyacid syn- thase (AHAS) and acetolactate synthase (ALS) for these herbicides are well known. Glyphosate resistance genes include mutant 5-enolpyruvylshikimate-3-phosphate syn- thase (EPSPs) and dgt-28 genes (via the introduction of recombinant nucleic acids and/or various forms of in vivo mutagenesis of native EPSPs genes), aroA genes and gly- phosate acetyl transferase (GAT) genes, respectively). Resistance genes for other phosphono compounds include bar and pat genes from *Streptomyces* species, including *Streptomyces hygroscopicus* and *Streptomyces* viridichro- mogenes, and pyridinoxy or phenoxy proprionic acids and cyclohexones (ACCase inhibitor-encoding genes). Exem- plary genes conferring resistance to cyclohexanediones and/ or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phos- photransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phos- photransferase (NEO); hygromycin phosphotransferase (HPT or HYG); dihydrofolate reductase (DHFR); phosphi- nothricin acetyltransferase; 2,2-dichloropropionic acid dehalogenase; acetohydroxyacid synthase; 5-enolpyruvyl- shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothri- cin. The above list of selectable marker genes is not meant to be limiting. Any reporter or selectable marker gene are encompassed by the present disclosure.

In some embodiments the coding sequences are synthe- sized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heter- ologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166, 302, and 5,380,831, herein incorporated by reference.

Molecular Confirmation

Methods of confirming the N7/N16 homoeologous chro- mosomal reciprocal translocation in *B. napus* are known in the art. For example the detection of the N7/N16 homoe- ologous chromosomal reciprocal translocation in *B. napus* can be achieved, for example, by the polymerase chain reaction (PCR). The PCR detection is done by the use of two oligonucleotide primers flanking the polymorphic segment of the polymorphism followed by DNA amplification. This step involves repeated cycles of heat denaturation of the DNA followed by annealing of the primers to their comple- mentary sequences at low temperatures, and extension of the annealed primers with DNA polymerase. Size separation of DNA fragments on agarose or polyacrylamide gels follow- ing amplification, comprises the major part of the method- ology. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Follow- ing successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybrid- ization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybrid- ization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLID™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLID) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

The tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

Plant Compositions and Breeding

In other embodiments, the subject disclosure provides a cell, tissue, or plant comprising the N7/N16 homoeologous chromosomal reciprocal translocation in *B. napus*. In some embodiments, cell, tissue, or plant of *B. napus* in accordance with the present disclosure includes, but is not limited to, any variety or line of *B. napus*. Thus, any variety or line of *B. napus* be selected with the as provided subject disclosure. In embodiments, *B. napus* is in reference to the common name of rapeseed, oilseed rape, rape or canola. In some embodiments, the genetic background within a variety or line of *B. napus* may vary.

In a further embodiment, the subject disclosure provides a seed comprising the N7/N16 homoeologous chromosomal reciprocal translocation. In subsequent embodiments a seed from *B. napus* is provided. A *B. napus* seed may be composed of three structural parts: (1) the outer hull, which is a protective outer covering; and (2) the embryo (which also includes the cotyledons).

The subject disclosure also relates to one or more *B. napus* plant parts. *B. napus* plant parts include plant cells, plant protoplasts, plant cell tissue cultures from which plants can be regenerated, plant DNA, plant calli, plant clumps, and plant cells that are intact in plants or parts of plants, such as embryos, pollen, ovules, flowers, seeds, leaves, roots, root tips, anthers, and the like.

In subsequent embodiments, the subject disclosure relates to a *B. napus* cell comprising the N7/N16 homoeologous chromosomal reciprocal translocation. In other embodiments, the subject disclosure relates to a *B. napus* plant part comprising the N7/N16 homoeologous chromosomal reciprocal translocation. In further embodiments, the subject disclosure relates to a *B. napus* plant tissue comprising the N7/N16 homoeologous chromosomal reciprocal translocation. In additional embodiments, the subject disclosure relates to a *B. napus* plant comprising the N7/N16 homoeologous chromosomal reciprocal translocation. In some embodiments, the subject disclosure relates to a *B. napus* seed comprising the N7/N16 homoeologous chromosomal reciprocal translocation.

An embodiment of the subject disclosure provides a method for producing a *B. napus* seed comprising the N7/N16 homoeologous chromosomal reciprocal translocation, the method comprising the steps of: a) crossing a female parent plant with a male parent plant; b) harvesting a progeny seed from the cross of (a); c) planting the progeny seed; and, d) growing the progeny seed, wherein the progeny seed comprises the N7/N16 homoeologous chromosomal reciprocal translocation.

In additional embodiments, the subject disclosure relates to female and male parent plants that are *B. napus* plants. In further embodiments the male parent plant is isogenic to the female parent plant. In an aspect of the embodiment, the male parent plant is homozygous or heterozygous for the N7/N16 homoeologous chromosomal reciprocal translocation. In another aspect of the embodiment, the female parent plant is homozygous or heterozygous for the N7/N16 homoeologous chromosomal reciprocal translocation.

In yet another aspect of the subject disclosure, processes are provided for producing progeny plants, which processes generally comprise crossing a first parent plant with a second parent plant wherein at least one of the first parent plant or the second parent plant comprises the N7/N16 homoeologous chromosomal reciprocal translocation. These processes may be further exemplified as processes for producing progeny seed or plants, wherein a first plant is crossed with a second plant.

Any time the male plant is crossed with another, different inbred plant, a progeny or first generation ($F_1$) hybrid plant is produced. As such, a progeny or $F_1$ hybrid plant may be produced by crossing the first plant with any second inbred plant. Therefore, any progeny or $F_1$ hybrid plant or seed that comprises the N7/N16 homoeologous chromosomal reciprocal translocation which is produced with the first parent plant as a parent is an embodiment of the subject disclosure.

In embodiments of the present disclosure, the step of "crossing" the *B. napus* plant comprises planting, preferably in pollinating proximity, seeds of a first inbred *B. napus* plant and a second, distinct inbred *B. napus* plant. In other embodiments, the step of "crossing" the *B. napus* plant comprises planting, manually pollinating a first inbred *B. napus* plant with pollen to a second, distinct inbred *B. napus* plant.

In an embodiment, the *B. napus* plant that comprises the N7/N16 homoeologous chromosomal reciprocal translocation are treated with one or more agricultural chemicals as considered appropriate by the grower.

A further step comprises harvesting the seeds, near or at maturity, from the plant that received the pollen. In a particular embodiment, seed is harvested from the female parent plant, and when desired, the harvested seed can be grown to produce a progeny or first generation ($F_1$) hybrid plant.

Yet another step comprises drying and conditioning the seeds, including the treating, sizing (or grading) of seeds, and packaging for sale to growers for the production of oil and grain. As with inbred seed, it may be desirable to treat hybrid seeds with compositions that render the seeds and seedlings grown therefrom more hardy when exposed to adverse conditions. Mention should be made that resulting progeny or hybrid seed may be sold to growers for the production of oil and grain and not for breeding or seed production.

Still further, the subject disclosure provides a progeny plant produced by growing the harvested seeds produced on the *B. napus* plant that comprises the N7/N16 homoeologous chromosomal reciprocal translocation as well as grain produced by the progeny plant.

In an additional embodiment, the subject disclosure relates to a method for producing a progeny plant, the method further comprising the steps of: e) crossing the progeny plant, with another plant comprising a desired trait to produce F1 progeny plants; f) selecting F1 progeny plants that have the desired trait to produce selected F1 progeny plants; g) crossing the selected F1 progeny plants with the progeny *B. napus* plant that comprises the N7/N16 homoeologous chromosomal reciprocal translocation plant to produce backcross progeny plants; h) selecting for backcross progeny plants that have the desired trait; and, i) repeating steps (g) and (h) three or more times in succession to produce selected fourth or higher backcross progeny plants that comprise the desired trait.

Various breeding schemes may be used to produce progeny plants. In one method, generally referred to as the pedigree method, the parent may be crossed with another different plant such as a second inbred parent plant, which either itself exhibits one or more selected desirable characteristic(s) or imparts selected desirable characteristic(s) to a hybrid combination. If the two original parent plants do not provide all the desired characteristics, then other sources can be included in the breeding population. Progeny plants, that is, pure breeding, homozygous inbred lines, can also be used as starting materials for breeding or source populations from which to develop progeny plants.

Thereafter, resulting seed is harvested and resulting superior progeny plants are selected and selfed or sib-mated in succeeding generations, such as for about five to about seven or more generations, until a generation is produced that no longer segregates for substantially all factors for which the inbred parents differ, thereby providing a large number of distinct, pure-breeding inbred lines.

In another embodiment for generating progeny plants, generally referred to as backcrossing, one or more desired traits may be introduced into the parent by crossing the parent plants with another plant (referred to as the donor or non-recurrent parent) which carries the gene(s) encoding the particular trait(s) of interest to produce $F_1$ progeny plants. Both dominant and recessive alleles may be transferred by backcrossing. The donor plant may also be an inbred, but in the broadest sense can be a member of any plant variety or population cross-fertile with the recurrent parent. Next, $F_1$ progeny plants that have the desired trait are selected. Then, the selected progeny plants are crossed with the parent or restored fertile parent to produce backcross progeny plants. Thereafter, backcross progeny plants comprising the desired trait and the physiological and morphological characteristics of the parent are selected. This cycle is repeated for about one to about eight cycles, preferably for about three or more times in succession to produce selected higher backcross progeny plants that comprise the desired trait and all of the physiological and morphological characteristics of the parent when grown in the same environmental conditions. Exemplary desired trait(s) include insect resistance, enhanced nutritional quality, herbicide resistance, yield stability, yield enhancement and resistance to bacterial, fungal and viral disease. One of ordinary skill in the art of plant breeding would appreciate that a breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant, and preferably the traits are measured on plants grown under the same environmental conditions.

This method results in the generation of progeny inbred plants with substantially all of the desired morphological and physiological characteristics of the recurrent parent and the particular transferred trait(s) of interest. Because such progeny inbred plants are heterozygous for loci controlling the transferred trait(s) of interest, the last backcross generation would subsequently be selfed to provide pure breeding progeny for the transferred trait(s).

In other embodiments for generating progeny plants the subject disclosure relates to the production of doubled haploid plants produced from *B. napus* microspores, wherein the doubled haploid plants comprise the N7/N16 homoeologous chromosomal reciprocal translocation. Those with skill in the art would appreciate that a microspore derived embryo may be produced from microspores that are obtained from the anthers of *B. napus*. These microspores—formed from pollen mother cells that undergo meiosis—are generated into embryos and later into mature plant by maintenance on the appropriate culture media followed by transfer to soil. The microspores are haploid cells. Those with skill in the art would understand that in some instances a haploid cell may spontaneously give rise to a diploid cell or cells following mitosis. Likewise, those with skill in the art would understand that a chromosome-doubling agent may be applied to increase the ploidy of a haploid cell. In aspects of such an embodiment the haploid cell becomes a diploid cell. Such a diploid cell may give rise to a *B. napus* plant comprising the N7/N16 homoeologous chromosomal reciprocal translocation. The methods of the present disclosure do not depend on a particular genetic mechanism of chromosome doubling. Typically, induced chromosome doubling of the invention involves administering an effective amount of a chromosome-doubling agent to a cell, preferably a haploid cell. Any agent that is known to increase the ploidy of cells may be employed in the methods of the subject disclosure. Exemplary, and non-limiting, chromosome doubling agents include, but are not limited to, trifluralin, colchicine, oryzalin, amiprophosmethyl and pronamide. Depending on the desired outcome, a chromosome-doubling agent may be administered to a tissue, or a cell thereof, but, is usually the doubling agent is applied directly to microspores via addition to the culture medium. In certain aspects of this embodiment, an effective amount of a chromosome-doubling agent is administered after obtaining the haploid embryo. In other aspects of this embodiment, an effective amount of a chromosome-doubling agent is administered at the microspore stage of *B. napus* development. Accordingly, the subject disclosure provides methods and compositions for developing progeny plants comprising the N7/N16 homoeologous chromosomal reciprocal translocation from *B. napus* microspores.

In further embodiments the subject disclosure relates to the determination of recombinant genetic frequencies in *B. napus* plants comprising the N7/N16 homoeologous chromosomal reciprocal translocation. In certain aspects, doubled haploid *B. napus* plants comprising the N7/N16 homoeologous chromosomal reciprocal translocation produced from microspores are used to determine the recombinant genetic frequencies. In other aspects, progeny *B. napus* plants comprising the N7/N16 homoeologous chromosomal reciprocal translocation are used to determine the recombinant genetic frequencies. In an aspect of this embodiment, the assays disclosed for the N7/N16 homoeologous chromosomal reciprocal translocation can be performed to identify linkage disequilibrium within the disclosed genomic sequences; for example, SEQ ID NO:1, SEQ ID NO:2, SEQ ID NO:3 and/or SEQ ID NO:4. The linkage of the polynucleotides from these genomic sequences (e.g., SEQ ID NO:1, SEQ ID NO: 2, SEQ ID NO:3, and/or SEQ ID NO:4) can be assayed using the methodologies and compositions as provided within this disclosure to determine the relative genetic distance to the N7/N16 homoeologous chromosomal reciprocal translocation. In an aspect of this embodiment, the assays disclosed for the N7/N16 homoeologous chromosomal reciprocal translocation can be performed to identify linkage disequilibrium within any *B. napus* genomic sequence on chromosome 7 or chromosome 16. The linkage of the polynucleotides from any *B. napus* genomic sequence on chromosome 7 or chromosome 16 can be assayed using the methodologies and compositions as provided within this disclosure to determine the relative genetic distance to the N7/N16 homoeologous chromosomal reciprocal translocation. In some aspects the linkage between the polynucleotides assayed from the genomic sequences can be linked, tightly linked, or extremely tightly linked to the N7/N16 homoeologous chromosomal reciprocal translocation. Those with skill in the art would appreciate that linkage of any polynucleotide sequence from the genomic sequences as disclosed herein (for example, SEQ ID NO:1, SEQ ID NO: 2, SEQ ID NO:3, and/or SEQ ID NO:4) to the breakage point of the N7/N16 homoeologous chromosomal reciprocal translocation may refer to the phenomenon in which the polynucleotides show a measurable probability of being passed on with the N7/N16 homoeologous chromosomal reciprocal translocation in the next generation. Likewise, those with skill in the art would appreciate that linkage of any polynucleotide sequence from within any *B. napus* genomic sequence on chromosome 7 or chromosome 16 to the breakage point of the N7/N16 homoeologous chromosomal reciprocal translocation may refer to the phenomenon in which the polynucleotides show a measurable probability of being passed on with the N7/N16 homoeologous chromosomal reciprocal translocation in the next generation. Thus, those with skill in the art would appreciate that the linkage of one polynucleotide sequence to another polynucleotide sequence may be measured and/or expressed as a recombination frequency. When the presence of a gene contributes to a phenotype in an individual, any polynucleotide sequences that are linked to the gene may be said to be linked to the phenotype. Accordingly, in aspects of this disclosure when the presence of the N7/N16 homoeologous chromosomal reciprocal translocation contributes to a phenotype in an individual, the polynucleotide sequences of the N7/N16 homoeologous chromosomal reciprocal translocation as provided in this subject disclosure that are linked to the gene may be said to be linked to the phenotype.

In a subsequent embodiment, the disclosure related to introducing a desired trait into *B. napus* plants comprising the N7/N16 homoeologous chromosomal reciprocal translocation plant. In an aspect of the embodiment, the desired trait is selected from the group consisting of a native trait or a transgenic trait that includes an insecticidal resistance trait, herbicide tolerant trait, disease resistance trait, yield increase trait, nutritional quality trait, agronomic increase trait, and combinations thereof.

The Introgression of a desirable trait in plants may be facilitated by repeated backcrossing. Described herein are methods for producing a *B. napus* plant with N7/N16 homoeologous chromosomal reciprocal translocation, through conventional plant breeding involving sexual reproduction. Methods may comprise crossing a first parent plant that comprises in its genome at least one copy of a trait to a second parent plant, so as to produce $F_1$ progeny. The first plant can be any plant or variety of *B. napus*. The second parent plant can be any plant that is capable of producing viable progeny plants (i.e., seeds) when crossed with the first plant. The first and second parent plants may be of the same *B. napus* line or variety. The methods may further involve selfing the $F_1$ progeny to produce $F_2$ progeny. Methods may further involve one or more generations of backcrossing the $F_1$ or $F_2$ progeny plants to a plant of the same line or genotype as either the first or second parent plant. Alternatively, the $F_1$ progeny of the first cross, or any subsequent cross, can be crossed to a third plant that is of a different line or genotype than either the first or second plant.

In some embodiments, progeny plants are subjected to a genotype and/or zygosity determination, as outlined in the disclosure. Once progeny plants have been genotyped, and/ or their zygosity determined, the skilled artisan may select those progeny plants that have a desired genetic composition. Such selected progeny plants may be used in further crosses, selfing, or cultivation. Methods of introgression of a trait that are directed according to methods of the disclosure reduce or eliminate the cultivation and/or reproduction of plants that do not have a desired genetic composition, and thereby provide desirable reliability and predictability (through expected Mendelian patterns of inheritance).

Backcrossing may be accelerated by the use of the N7/N16 homoeologous chromosomal reciprocal translocation assays of the pending application to identify plants with the greatest genetic complement from the recurrent parent.

Direct selection may be applied where a single locus acts as a dominant trait, such as the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. In the instance where the characteristic being transferred is a recessive allele, it may be necessary to introduce a test of the progeny to determine if the desired characteristic has been successfully transferred. The process of selection, whether direct or indirect, is then repeated for all additional backcross generations.

It should be appreciated by those having ordinary skill in the art that backcrossing can be combined with pedigree breeding as where the parent is crossed with another plant, the resultant progeny are crossed back to the parent or restored fertile parent and thereafter, the resulting progeny of this single backcross are subsequently inbred to develop new inbred lines. This combination of backcrossing and pedigree breeding is useful as when recovery of fewer than all of the parent characteristics than would be obtained by a conventional backcross are desired.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Discovery and Validation of
Chromosomal N7/N16 Reciprocal Translocation
Break Points in *B. napus*

To discover the location of the N7/N16 chromosomal break point in *B. napus*, an end-to-end chromosome assembly based on single molecule long read sequencing for *B. napus* line NS1822BC was developed. The resulting reference genetic map of line NS1822BC revealed the presence of an N7/N16 homoeologous chromosomal reciprocal translocation. Using a global alignment of the NS1822BC genome with that of publicly available *B. napus* line DH12075 genome (which does not contain the N7/N6 homoeologous chromosomal reciprocal translocation), the location and sequences of the two break-points on N7 and N16 chromosomes were identified for the first time. As provided herein, SEQ ID NO 4: provides the sequence of the N7/N16 homoeologous chromosomal reciprocal transloca-tion of chromosome 16 as compared to the wildtype sequence of chromosome 16 of SEQ ID NO:3. As provided herein, SEQ ID NO:2: provides the sequence of the N7/N16 homoeologous chromosomal reciprocal translocation of chromosome 7 as compared to the wildtype sequence of chromosome 7 of SEQ ID NO: 1. This analysis resulted in the precise estimation of the genetic and physical length of the N7/N16 homoeologous chromosomal reciprocal trans-location (Table 1). Furthermore, it was discovered that nearly one-third of the bottom end of the N7 chromosome (a 37 cM segment starting from 65.8 cM to the end of the chromosome at 102.8 cM in genetic space and an ~7.8 Mb physical segment starting from 17580520 bp to 25458507 on DH12075 genome) was involved in the homoeotic exchange with N16 chromosome. Similarly, an ~9.8 cM genetic seg-ment (0-9.8 cM) at the top of the N16 chromosome (~8.1 Mb physical segment starting from 0-13653938 bp on DH12075 genome) was involved in the homoeotic exchange with N7 chromosome. These exchanged segments were positioned in an inverted orientation in the individuals containing N7/N16 HRT.

Next, the N7/N16 homoeologous chromosomal reciprocal translocation was assessed and characterized in elite germ-plasm lines from North America (NA), Australia (AU), and Europe (EU). From this analysis, it was determined that the N7/N16 homoeologous chromosomal reciprocal transloca-tion is fixed in NA germplasm lines, nearly absent in EU germplasm lines, and segregates in AU germplasm lines (Table 2).

TABLE 1

Physical co-ordinates of the N7/N16 homoeologous chromosomal reciprocal translocation break-points

| Genome | Chromosome | Break point position left in bp | Break point position right in bp |
|---|---|---|---|
| DH12075 v1.1 | N7 | 17580519 | 17580520 |
| DH12075 v1.1 | N16 | 13653938 | 13653939 |
| NS1822BC | N7 | 20108868 | 20108869 |
| NS1822BC | N16 | 8092482 | 8092483 |

TABLE 2

| Germplasm characterization | | | |
|---|---|---|---|
| Breeding Geography | Total lines | Lines with Translocation | Lines without Translocation |
| Australian Spring type | 145 | 47 | 98 |
| European Winter type | 255 | 4 | 251 |
| North American Spring type | 434 | 400 | 34 |
| Total | 834 | 451 | 383 |

Example 2: Detection of N7/N16 Homoeologous Chromosomal Reciprocal Translocation Using Agarose-Based PCR Assays The genome sequence of the public DH12075 line that does not contain the N7/N16 translocation was used to develop two "wild type PCR assays" to detect the absence of the reciprocal chromosomal exchanges at both the N7 and N16 chromosomal sites respectively. The assays were designed using primers (Primer3 software: available on the world wide web at bioprod.phibred.com/primer3/cgi-bin/primer3_www.cgi) that flank the site of break-point sequences (Table 3, and Table 4). PCR amplification prod-ucts from these assays when run on an (1%) agarose gel produced a band of 2,366 bp for N7 and 1,963 bp for N16, diagnostic for the wild type configuration or absence of the N7/N16 translocation.

The genome sequence of the proprietary NS1822BC line that does contain the N7/N16 translocation was used to develop two PCR assays each on N7 and N16 that detect the reciprocal translocation. These assays were developed using primers that flank the chromosome exchange points on N7 and N16 chromosome sequences (Table 3, and Table 4). When run on the agarose gels these assays produce products of 1,828 bp for N7 and 1,893 bp for N16 that will detect the presence of N7 and N16 reciprocal recombination.

TABLE 3

| Sequence IDs and physical positions used in the Detection of N7/N16 homoeologous chromosomal reciprocal translocation using agarose-based PCR assays | | | | | |
|---|---|---|---|---|---|
| SEQ ID NO: | Sequence description | Genome | Chromosome | Physical location (start) | Physical location (end) |
| SEQ ID NO: 1 | N7 HRT Seq 1 | DH12075 v1.1 | N7 | 17578019 | 17583020 |
| SEQ ID NO: 2 | N7 HRT Seq 2 | NS1822BC | N7 | 20106368 | 20111369 |
| SEQ ID NO: 3 | N16 HRT Seq 1 | DH12075 v1.1 | N16 | 13651438 | 13656439 |
| SEQ ID NO: 4 | N16 HRT Seq 2 | NS1822BC | N16 | 8089982 | 8094983 |

TABLE 4

Primer IDs, physical positions, and sequences used in the
Detection of N7/N16 homoeologous chromosomal reciprocal
translocation using agarose-based PCR assays

| Primer ID | Reference physical position | Sequence ID physical position | Sequence |
|---|---|---|---|
| DH N7 F | DH12075 N7:17580813 | N7 HRT Seq 1: 2501 | TTTAACAAAGTAAGGT GTTTCTTGTG SEQ ID NO: 5 |
| DH N7 R | DH12075 N7:17578511 | N7 HRT Seq 1: 174 | TTAAGCCAACATGTGC AGGA SEQ ID NO: 6 |
| DH N16 F | DH12075 N16:13653931 | N16 HRT Seq 1: 2132 | AGCGACTTTTCACAAA GTAGGG SEQ ID NO: 7 |
| DH N16 R | DH12075 N16:13655875 | N16 HRT Seq 1: 4094 | TGATGGTTAAAACCCA CTGC SEQ ID NO: 8 |
| NS N7 F | NS1822BC N7:20108854 | N7 HRT Seq 2: 2509 | CAACGACTTTTCACAA AGTAGGG SEQ ID NO: 9 |
| NS N7 R | NS1822BC N7:20107032 | N7 HRT Seq 2: 665 | GCCTCAGTTATTATGT TTGTGATGG SEQ ID NO: 10 |
| NS N16 F | NS1822BC N16:8094055 | N16 HRT Seq 2: 4074 | GTGATGGTTAAAACCC ACTGC SEQ ID NO: 11 |
| NS N16 R | NS1822BC N16:8092164 | N16 HRT Seq 2: 2183 | TTTAACAAAGTAAGGT GTTTCTTGTG SEQ ID NO: 12 |

The lines NS1882BC (confirmed to have the translocation) and DH12075 (confirmed to not contain the translocation) were used as positive and negative controls when testing the effectiveness of the PCR assay to detect the presence or absence of translocation. PCR reactions were set up in 20 ul volume containing 2 ul of DNA (~8 ng), 4 ul of 100 mM primers (2 ul forward 2 ul reverse), 10 ul Phusion GC Master Mix™ (Fisher scientific) and 4 ul of water. PCR conditions were as follows: 98° C. for 30 secs, followed by 35 cycles of 98° C. for 10 secs, 61° C. for 30 secs, and 72° C. for 120 secs, with a final extension of 72° C. for 7 mins and a final infinite hold at 4° C. PCR products were separated on a 1% agarose gel (SeaKem GTG agarose™, Lonza) containing Sybr Safe (Sybr Safe DNA gel stain™, Unity) in 1X TAE buffer (Omnipur TAE buffer, Thermo Fisher Scientific) for 1 h and visualized and photographed using an Alpha Imager utilizing a bottom illumination plate set to emit light at ~530 nm. Gel images were scored with a score of one (1) representing presence and a score of zero (0) representing absence of the reciprocal translocation.

Example 3: Detection of N7/N16 Homoeologous Chromosomal Reciprocal Translocation Using High-Throughput Competitive Allele-Specific PCR Genotyping (KASPR™) Assays High-throughput markers greatly facilitate the large-scale germplasm screening and breeding. Co-dominant assays that allow detection of translocated lines from non-translocated for N7/N16 homoeologous chromosomal reciprocal translocation were designed using the breakpoint sites at both N7 and N16 sequences. The KASPAR™ genotyping system is comprised of two components (1) the SNP-specific assay (a combination of three unlabelled primers), and (2) the universal Reaction Mix, which contains all other required components including the universal fluorescent reporting system and a specially-developed Taq polymerase. The four primers, allele-specific 1 (A1), allele-specific 2 (A2), and two common (C1 and C2), or reverse, (Table 5) were designed using the assay design algorithm of the workflow manager, Kraken™ (LGC Genomics, Hoddesdon, Hertfordshire, UK).

TABLE 5

Primer identification and physical positions, used in the
detection of N7/N16 homoeologous chromosomal reciprocal
translocation using KASP ™ assays:

| Primer | Primer ID | Reference physical position | Sequence ID physical position | Sequence |
|---|---|---|---|---|
| N7 A1 | N7_S3 F1 | DH12075 N7:17580752 | N7 HRT Seq 1: 2415 | GTCCGTTTGCTTTAAT AAGCCCAA SEQ ID NO: 13 |
| N7 A2 | N7_S3 F2 | NS1822BC N7:20108782 | N7 HRT Seq 2: 2416 | TCCCGTGTGCTTTAAT AAGCCCAG SEQ ID NO: 14 |
| N7 C1 | Cr5 DH | DH12075 N7:17580893 | N7 HRT Seq 1: | AGATCAGCGACTTTTC ACAAA |

TABLE 5-continued

Primer identification and physical positions, used in the
detection of N7/N16 homoeologous chromosomal reciprocal
translocation using KASP ™ assays:

| Primer | Primer ID | Reference physical position | Sequence ID physical position | Sequence |
|--------|-----------|------------------------------|-------------------------------|----------|
| | | | 2875 | SEQ ID NO: 15 |
| N7 C2 | Cr5 NS | NS1822BC | N7 HRT | CCAGTTTTCAGAGGG |
| | | N7:20108860 | Seq 2: | AGTTTT |
| | | | 2556 | SEQ ID NO: 16 |
| N16 A1 | DH16_PA F | DH12075 | N16 HRT | ACCTCAACCTCAACCC |
| | | N16:13654237 | Seq 1: | CAATC |
| | | | 2437 | SEQ ID NO: 17 |
| N16 A2 | N16_NS_F2 | NS1822BC | N16 HRT | GGAGGAGGAGGAGGA |
| | | N16:8092483 | Seq 2: | GTCGTT |
| | | | 2501 | SEQ ID NO: 18 |
| N16 C1 | DH16_PA_ Cr2 | DH12075 | N16 HRT | GGGATTGGATTACGG |
| | | N16:13654263 | Seq 1: | TTTTCGGGTT |
| | | | 2487 | SEQ ID NO: 19 |
| N16 C2 | NS16_PA_CR1 | NS1822BC | N16 HRT | ATTTTCCACATGGGTG |
| | | N16:8092428 | Seq 2: | AACCACAA |
| | | | 2470 | SEQ ID NO: 20 |

Primers were designed using the LGC Genomics assay design software. As such, 1.5 ul of ~4 ng/ul of DNA was used in the assay mix (~6 ng), and 12 ul of 100 mM of each forward primer and 30 ul of 100 mM of each of the common reverse primers and 16 ul of water was combined to make each assay. Next, 13.6 ul of the assay was combined with 1000 ul of KASP Master Mix™ (LGC Genomics, Hoddesdon, Hertfordshire, UK). A Meridian™ (LGC Genomics, Hoddesdon, Hertfordshire, UK) liquid handler dispensed 1.3 ul of the mix onto a 1536 plate containing ~6 ng of dried DNA. The plate was sealed with a Phusion™ laser sealer (LGC Genomics, Hoddesdon, Hertfordshire, UK) and thermocycled using a LGC Genomics™, Hoddesdon, Hertfordshire, UK hydrocycler with the following conditions: 95° C. for 15 min, 10 cycles of 95° C. for 20 sec, 61° C. stepped down to 55° C. for 1 min, 29 cycles of 95° C. for 20 sec, and 55° C. for 1 min. The excitation at wavelengths 485 (FAM) and 520 (VIC) was measured with a Pherastar™ plate reader (BMG Labtech, Offenburg, Germany). The values were normalized against ROX and plotted and scored on scatterplots utilizing the KRAKEN software (LGC Genomics, Hoddesdon, Hertfordshire, UK).

Example 4: Detection of N7/N16 Homoeologous Chromosomal Reciprocal Translocation Using an Endpoint Assay Development Generally, the endpoint genotyping system is comprised of a forward and reverse primer and two fluoresce labeled probes. The oligonucleotide primers amplify a specific region of the wildtype N7 or N16 chromosome, and the translocated N7 or N16 chromosome. The oligonucleotide probe binds to the amplicon between the two primers and are labeled with the VIC or FAM fluorescent reporter dye, at the 5' end and MGBNFQ (minor grove binding non-fluorescent quencher) as a quencher at the 3' end.

An exhaustive listing of endpoint genotyping systems (e.g., TAQMAN™, KASPAR™, or other known assays) that rely on amplifiable primers (SEQ ID NO:489-10560) and probes (SEQ ID NO:21-488) that spanned the N7/N16 translocation break-point site were designed. As provided herein the wildtype chromosome 7 can be assayed with SEQ ID NO:489-2990 and probed with SEQ ID NO: 138-254.

The assay for wildtype chromosome 7 utilizes any of SEQ ID NO: 489-1739 as a forward or 5' primer, in combination with any of SEQ ID NO: 1740-2990 as a reverse or 3' primer, and in combination any of SEQ ID NO:138-254 as a probe. As provided herein the wildtype chromosome 16 can be assayed with SEQ ID NO:2991-5492 and probed with SEQ ID NO:21-137. The assay for wildtype chromosome 16 utilizes any of SEQ ID NO: 2991-4241 as a forward or 5' primer, in combination with any of SEQ ID NO:4242-5492 as a reverse or 3' primer, and in combination any of SEQ ID NO: 21-137 as a probe. As provided herein the homoeologous chromosomal reciprocal translocation of chromosome 7 can be assayed with SEQ ID NO: 5493-8026 and probed with SEQ ID NO: 372-488. The assay for the homoeologous chromosomal reciprocal translocation of chromosome 7 utilizes any of SEQ ID NO: 5493-6759 as a forward or 5' primer, in combination with any of SEQ ID NO:6760-8026 as a reverse or 3' primer, and in combination any of SEQ ID NO:372-488 as a probe. As provided herein the homoeologous chromosomal reciprocal translocation of chromosome 16 can be assayed with SEQ ID NO: 8027-10560 and probed with SEQ ID NO:255-371. The assay for the homoeologous chromosomal reciprocal translocation of chromosome 16 utilizes any of SEQ ID NO:8027-9294 as a forward or 5' primer, in combination with any of SEQ ID NO:9295-10560 as a reverse or 3' primer, and in combination any of SEQ ID NO:255-371 as a probe. Those with skill in the art can utilize such compositions to devise an assay for the detection of N7/N16 homoeologous chromosomal reciprocal translocation in *B. napus*.

These primer and probe sequences as disclosed herein can be used as diagnostic assays for the detection of N7/N16 homoeologous chromosomal reciprocal translocation. As such, 1.5 ul of the ~6 ng/ul DNA is used in the assay mix, and 18 uM of each probe, and 4 uM of each primer is combined to make each assay. Next, 13.6 ul of the assay is combined with 1000 ul of ToughMix PCR Master Mix™ (Quanta Beverly, Mass, USA). A Meridian (LGC Genomics, Hoddesdon, Hertfordshire, UK) liquid handler dispenses 1.3 ul of the mix onto a 1536 plate containing ~6 ng of dried DNA. The plate is sealed with a Phusion™ laser sealer (LGC Genomics, Hoddesdon, Hertfordshire, UK) and thermocycled using a LGC Genomics™, Hoddesdon, Hertfordshire, UK hydrocycler with the following conditions: 94° C. for 15 min, 40 cycles of 94° C. for 30 secs, 60° C. for 1 min. PCR products are measured using at wavelengths 485 (FAM) and 520 (VIC) by a Pherastar plate reader (BMG Labtech, Offenburg, Germany). The values are normalized against ROX and plotted and scored on scatterplots utilizing the KRAKEN software (LGC Genomics, Hoddesdon, Hertfordshire, UK). Genotype is determined by the presence or absence of fluorescence specific to the translocation.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

---

What is claimed is:

1. A method of breeding a canola plant comprising a N7/N16 homoeologous chromosomal reciprocal translocation comprising SEQ ID NO: 2, the method comprising:

(a) amplifying nucleic acid from a canola plant, tissue, or cell with a primer pair consisting of SEQ ID NO: 13 and SEQ ID NO: 15 or the complements thereof under very high stringency conditions to generate am amplicon, (b) hybridizing a labeled probe comprising SEQ ID NO: 511 with the amplicon to detect the N7/N16 homoeologous chromosomal reciprocal translocation of SEQ ID NO:2, (b) selecting the canola plant, tissue, or cell with the N7/N16 homoeologous chromosomal reciprocal translocation of SEQ ID NO:2; and (c) breeding the canola plant, to obtain a progeny of the canola plant, tissue, or cell comprising the N7/N16 homoeologous chromosomal reciprocal translocation comprising SEQ ID NO:2.

2. The method of claim 1, the method further comprising:

(a) quantitating the amplicon produced by an amplification reaction.

3. The method of claim 2, wherein quantitating the results of the amplification reaction comprises producing a signature profile.

4. The signature profile of claim 3, wherein the signature profile is selected from the group consisting of a melting temperature curve signature profile and a fluorescence signature profile.

5. The method of claim 4, wherein the signature profile is produced from an intercalating DNA dye, a cyanine dye, or a fluorescent dye.

6. The method of claim 1, the method further comprising determining the presence or absence of the N7/N16 homoeologous chromosomal reciprocal translocation by determining the nucleotide sequence of said nucleic acid.

7. The method of claim 1, the method further comprising determining the presence or absence of the N7/N16 homoeologous chromosomal reciprocal translocation by determining the size of said nucleic acid.

8. The method of claim 7, wherein said determining the size comprises HPLC or electrophoresis.

* * * * *

SEQUENCE LISTING

```
<160> NUMBER OF SEQ ID NOS: 1115

<210> SEQ ID NO 1
<211> LENGTH: 5002
<212> TYPE: DNA
<213> ORGANISM: brassica napus

<400> SEQUENCE: 1
aattaagaaa aacatttgta taaaaatatt ttctaaaata tttttaatat gtgagcatat      60
atattttaat gaattttta tatatataca agtaatctga tatttgagtt aaaatttttg     120
gaaacataaa atgctaattt cgaattatgt ttgtgtgatt atttgtaaga agattaagcc     180
aacatgtgca ggaaaaacac ctggttaaca atgagaaaat gaaagatttg gctctgtttt     240
acaggaataa tgagctttct ttaagcagca attttaagcc tccaacaaga gaaatcaaa     300 gttcatcggc taaactatat atctttacat aacaagacgg tttctgccgc atagtctttc     360
agtttcgtgt cttgagaaac ccaacctaca aaagttcctg ctttattctt atttcttcac     420
agcagaacac tcgacctttt cacctgacag tagctgaaga ccggaccaga accctctaac     480
gccatggacg acaacaactt atggtgggaa gccagctaag tttggcccca tgccctgtta     540
agtagtcaat aagaaccaca taagaagact aatgtatcaa caacctcgtt ataattgtaa     600
ttactcctta attaacaaac caagtattca gcattacaaa agtatagtga cttggatgag     660
aaaagcctca gttattatgt ttgtgatggt ttccacattt taacgttgtc acgtgaaaca     720
ctagtaccta aggtacgcaa agtatcaaat attagaatcc ctatgtacca ttttcttcaa     780
catgatcttg ttttagtgaa ggctttcact gccgcacatg tgattacgtt gaaaagtaaa     840
ggcctccaca tgaaaaatct atcaatttac gtctatcaag ccatgaaaac cagcctcaat     900
acacattccc tgcatagatg ctactcttga acatactaaa ctccacgaaa ctatggtatt     960
ttctcatgtg acttgtcagc tcgatacaag ttttagatac taaaaactat cttaaccaca    1020
atccccttga caattgcatc tacagttaaa gctaaatacc ttgtgaagca ttgagattaa    1080
ctttaggaaa cgataactag acgttagtac tcgttttcag aaagtaccat ctataaggca    1140
accactccag tgactgctac atctacctta agggcaaact tcaagcaggg acaagtattg    1200
cacagaaact acgttagata cagtagctga ctatacccga tactgaacac actaagaggg    1260
tccagaagct gtgactgttg ttgctgttgc atgtcttcca actgcggaaa cgccaaatca    1320
gctcctgaac tcacagcccc agcactagac ggcgtccctt tcgcttcaat gagccgccac    1380
atgtaccaag acccaacaga cctatacgga cgccacttct cgcaaatccc ctccatctgc    1440
gaaggacgag gcagctccgg caagtcataa agcatctgca cacctttcct cacaccaaga    1500
tcgttaacag gcaacacatc aggtctatga agcgagttta tcataaacat atgaaccgac    1560
cacgacccaa tcccgttaac catcgtcagc atcgtgaaca gagacttatc atccatgctc    1620
acaatcccag aatccgacaa gataccgttt tgatactttc tcgcgagatc gtggaggtaa    1680
ctcgctttcc tcccggagac accaatctga cgaagctcct gaggcgtcaa aggcaagaca    1740
```

-continued

```
ttctccggaa cgacgccgtt ttcgcctccg cagagggaaa cgaagcgcgt gtagattgag    1800
ttccccgctt tggcagcaag ctgctggtag aggatgcttc ggatgagagc caagaaggga    1860
gtgttgaaag actcgtactt tggcggtggg tgtgcgtcga tcaacgaggc taggagagga    1920
tcgacgctgc ggaggtgggt aatcgccgct tcgagctctc cctcgcaagt tagagacttt    1980
gcgtggatcc tcggtggctg cgatggtttg cccttcggtg aaggtctcgc gtcgttgttg    2040
ggagaaagct ttctgatttt tcgaggacgg agagggattt tggaaggagg ggaggataca    2100
ttgcttagct cggtgattct cggggcttcg atggtggttg atgagacgat tgagccggga    2160
acggaggcgg aggaggagtc gtcggaatcg ttgctttgcg gtggttgaga aggttgtggt    2220
tcacccatgt ggaaaatcga attgggttga attagggttt tgtttgatcg cttgaagaag    2280
taatcggaga atggacacgg cggagtgaag ttgcgtcttt tggcttgact ttgattcttt    2340
tctgacgcgc ttttaactat agtggccttc acgctccgat gtcttctgtg tgggctttat    2400
gataaaaaag tagagtccgt ttgctttaat aagcccaaac tggattactt gggtctttca    2460
actgagctca atatacacaa gaaacacctt actttgttaa atttaaaata gttacaaagt    2520
aaataaaagt tgattaaaac tccctctgaa aactgggggg aaaagtcgtt gatctattgt    2580
tttcatataa tttgagaatt aactgagtga tgttttgtg gtcaacaaaa gagttaatta    2640
atgggaaatt gcatccaata tacacacaaa aaaacaaaat tcactaacta actaaaaaca    2700
ccccctctct cctactttct cttcctatct ctctctactc tctctctctc taaaaatcta    2760
atttcacttt tttttttggct attcagcaaa taagcccctta attaattggg tgatgaataa    2820
gccgaaactg gaatgcttga gttagaccct tctttgtgaa ataaataaca attaaatact    2880
tttccaagag tcttgatcta ttgttttcat ataatttgag actttactga gtaatgttat    2940
gtttaatttt attataagga ttaaagaata aaatatacaa tggcgatggg aaggactatt    3000
cactacaaaa aaaacattga attgtatcac ttaaattgta tcacaaaaat aagtgatacc    3060
attttaaatc acttattcag aactgaaaca aatatttata cttttaaatc atttatagta    3120
attgatgtta ttattaatta atttaacatc agttcgatat aagtgatgtc ttttcttta    3180 atttgtatca ttttaacaaa aatgatacaa ttatataaaa ttatatcaat tacacaattg    3240
atgcatatat tattttgttt agtatcactt atttaaatga tctataattt acatcagtaa    3300
aataattgat gctaataaaa attatatata tatatatata tatattagca tcggtctaat    3360
aaaaatgata ttgtttttaa tcttattttg catctgttga aatatattat ctagtacaaa    3420
attagtttgg atctataaaa taattaataa atataatata attgtataat tatatactaa    3480
acaggatcta ttatagttcc ccaaaaaaag gaaccacaat cccacataaa acgtgaacta    3540
atcagttaaa aagtagggaa taccagaaat agtatatat tcttgtgatt ttaatttttt    3600
gttagcttta attttactgg atcataattt tctataactg tttcacttca atattttcat    3660
cttcgtctct ttttcatttt ttctctgtttt cagtttctta aacttttgtt cagagcttaa    3720
aatttgttgt tttggttatt tgatcagaaa cagatttcaa caatatcaag cattatatga    3780
gtcacgatga caaatgcgtt tcttttcatg aaagggttta aagattgctg aagtttgcta    3840
atcaaacgac tctgattaaa cttttgagag gtattatttc tttttttcttt ctctattctc    3900 aaacttttg aaaactacaa gttcttatat ttttttgttta tgtcttaata atcattctct    3960
attaggatca gaataattca gagatatatg aagacacgac aagagtgatt tgaaatgtgg    4020
aggaaaatcg atagagattg aagatgaaaa aagaagatgc aaagaatgag aagaaagaag    4080
```

-continued

```
aagaatctgg atataattgc tagtattttt tttgtatctc cgcattcttc atgttttttt      4140
ctttctcata actagtaatt tgtttaactt tctatagtct tttttttcttc tctgtacctt      4200 ttttatttt cttgtttttct tggctacgtt atatttcaat ggaaaattaa taaattgtta      4260
caaaataata ttttatttta tatgtatttt ctactctaca aatgattcta atatttaaaa      4320
caataactat aaatagtaaa actattaaaa tatttttttaa taaatcgata ttaatttatt      4380
aaattattaa ttaatatttt attaactaaa tcagttattt taattgatgt caatactaat      4440
atcatttgga aaaattgatg taattgttaa tatcgttttt acaattgata tatatattga      4500
catcacataa agtaactgat gaaaatataa taatttctta catcatttgt taataaaatg      4560
atgtaaatta tttgtatcac cactttcaga gtcatttatt taagtgatgt aaaattattt      4620
tacatcattt ataactaatg caaaaatata aattaaatga tgctaaatga cttttttttt      4680
tgtagtgatt gtacatgtga ggaacgagga ggaaacaaaa agacttgatc agtgttatgt      4740
acaatgcaga tatataaata tttgtggtca acaaaaaaaa ttagatcgtg gtgatgtgga      4800
gacagtaata tcagatcaca aagacgtgtt tggtgtgata tgatactctg tctttctgac      4860
catctcttac ctcacatttc gctcgttttg ttttttgttc ttttatttct ttctaccaaa      4920
cagcaaacta aaaaacaatg aaaataaata ttttttttat ttaatataaa gtctaccatc      4980
tttaaaaata atattctggc tt                                               5002
```

```
<210> SEQ ID NO 2
<211> LENGTH: 5002
<212> TYPE: DNA
<213> ORGANISM: brassica napus

<400> SEQUENCE: 2
aattaagaaa aacatttgta taaaaatatt ttctaaaata ttttttaatat gtgagcatat        60 atattttaat gaattttttta tatatataca agtaatctga tatttgagtt aaaatttttg       120
gaaacataaa atgctaattt cgaattatgt ttgtgtgatt atttgtaaga agattaagcc       180
aacatgtgca ggaaaaacac ctggttaaca atgagaaaat gaaagatttg gctctgtttt       240
acaggaataa tgagctttct ttaagcagca attttaagcc tccaacaaga gaaaatcaaa       300
gttcatcggc taaactatat atctttacat aacaagacgg tttctgccgc atagtctttc       360
agtttcgtgt cttgagaaac ccaacctaca aaagttcctg ctttattctt atttcttcac       420
agcagaacac tcgacctttt cacctgacag tagctgaaga ccggaccaga accctctaac       480
gccatggacg acaacaactt atggtgggaa gccagctaag tttggcccca tgccctgtta       540
agtagtcaat aagaaccaca taagaagact aatgtatcaa caacctcgtt ataattgtaa       600
ttactcctta attaacaaac caagtattca gcattacaaa agtatagtga cttggatgag       660
aaaagcctca gttattatgt ttgtgatggt ttccacattt taacgttgtc acgtgaaaca       720
ctagtaccta aggtacgcaa agtatcaaat attagaatcc ctatgtacca ttttcttcaa       780
catgatcttg ttttagtgaa ggctttcact gccgcacatg tgattacgtt gaaaagtaaa       840
ggcctccaca tgaaaaatct atcaatttac gtctatcaag ccatgaaaac cagcctcaat       900
acacattccc tgcatagatg ctactcttga acatactaaa ctccacgaaa ctatggtatt       960
ttctcatgtg acttgtcagc tcgatacaag ttttagatac taaaaactat cttaaccaca      1020
atccccttga caattgcatc tacagttaaa gctaaatacc ttgtgaagca ttgagattaa      1080
ctttaggaaa cgataactag acgttagtac tcgtttttcag aaagtaccat ctataaggca      1140
accactccag tgactgctac atctacctta agggcaaact tcaagcaggg acaagtattg      1200
```

-continued

```
cacagaaact acgttagata cagtagctga ctatacccga tactgaacac actaagaggg    1260
tccagaagct gtgactgttg ttgctgttgc atgtcttcca actgcggaaa cgccaaatca    1320
gctcctgaac tcacagcccc agcactagac ggcgtccctt tcgcttcaat gagccgccac    1380
atgtaccaag acccaacaga cctatacgga cgccacttct cgcaaatccc ctccatctgc    1440
gaaggacgag gcagctccgg caagtcataa agcatctgca cacctttcct cacaccaaga    1500
tcgttaacag gcaacacatc aggtctatga agcgagttta tcataaacat atgaaccgac    1560
cacgacccaa tcccgttaac catcgtcagc atcgtgaaca gagacttatc atccatgctc    1620
acaatcccag aatccgacaa gataccgttt tgatactttc tcgcgagatc gtggaggtaa    1680
ctcgctttcc tcccggagac accaatctga cgaagctcct gaggcgtcaa aggcaagaca    1740
ttctccggaa cgacgccgtt ttcgcctccg cagagggaaa cgaagcgcgt gtagattgag    1800
ttccccgctt tggcagcaag ctgctggtag aggatgcttc ggatgagagc caagaaggga    1860
gtgttgaaag actcgtactt tggcggtggg tgtgcgtcga tcaacgaggc taggagagga    1920
tcgacgctgc ggaggtgggt aatcgccgct tcgagctctc cctcgcaagt tagagacttt    1980
gcgtggatcc tcggtggctg cgatggtttg cccttcggtg aaggtctcgc gtcgttgttg    2040
ggagaaagct ttctgatttt tcgaggacgg agagggattt tggaaggagg ggaggataca    2100
ttgcttagct cggtgattct cggggcttcg atggtggttg atgagacgat tgagccggga    2160
acggaggcgg aggaggagtc gtcggaatcg ttgctttgcg gtggttgaga aggttgtggt    2220
tcacccatgt ggaaaatcga attgggttga attagggttt tgtttgatcg cttgaagaag    2280
taatcggaga atggacacgg cggagtgaag ttgcgtcttt tggcttgact ttgattcttt    2340
tctgacgcgc tttttaactat agtggccttc acgctccgat gtcttctgtg tgggctttat    2400
gataaaaaag tagagtccgt ttgctttaat aagcccaaac tggattactt gggtctttca    2460
actgagctca atatacacaa gcaacaccct actttgtgaa aagtcgctga tcttattgtt    2520
ttcaaataat ttgagaatta actgagtgat gttttgtgg tcaacaaaaa agttaattaa    2580
ttgggagatg aataaaactg gaatgcttaa ttaatttaaa agaaatttta atgaaacaaa    2640
ccctcaacta taactatagg cccatttgtt ttttaacct taagcatttt tataattgtt    2700
agagataata tcaaaagata cgattaacca tttgctattt aggataaata ttatctttt    2760 tttattttgt catttcttat gtcagttaat ttgaccgact tactaccact ataaatagtg    2820
gtttcatctc atttataacg atatgagaac aacaataata atatgatcat ctcacatatt    2880
catctctctt acgttactta gcaaacaaga aacaaatata tatatatata tatatatata    2940
tgtaataata catatataaa tattcaccta ttatttcaca acacgttatc aacacgagct    3000
ctcatatacc ggtgaagtct atcaatccgg aagctctaac caaccgaagc ttatcaatcc    3060
gaaagttctt aaaccagccg agaaaatgcc aaactttgag actatggatg gagatttgtg    3120
tttggcagat agtgcgtcaa cgcacacgat aattaaagat aagaaatatt tctccagtct    3180
caaaataaaa gattacgctg gaagcgtaag tacaatatct ggtaatgcaa agattattat    3240
gagctctgga agagcgaaat tttcaatgcc aggggggaaca atatttgaaa taagtgatgc    3300
attgtatccc cccgagtctc atagaaactt attaagtttt aaggatatcc gaagaaatgg    3360
atatcatatt gagactatga gtaaagatga cactaaattt ctttgcaata agtccgagag    3420
gaaacatata ttggaagagt taagaatgtt atcctctgga ctatattgta cgaaaattac    3480
catgactgag tcctatgccg tggtaaacat gaagtttact gatacattta aaatttggca    3540
```

```
tgagaggcta ggacatcctg gttcagtcat gatgagaaag atagtgtaaa attcgaatgg      3600
ccatccgttg aaaaacggaa aattttttgca aacgggcgag tttacatgta atgcatgttc     3660
tcaaggaaaa cttataactc ggccatcacc agcaaaagta ggcaatgaat caccaatgtt      3720
tttggaaaga atacatggtg atatatgtgg gccgatccac ccaccgtgcg ggccgtttaa      3780
gtattttatg gtattgattg acgcatatag tagatggtca agtgtatctc ttttgacgac      3840
acaaaatacg gctttcgcaa agttcattgc ccagataata aagctgagaa cgcagttctc      3900
agagtatgcc attaagaaag taaggcttga taatgctggt gaatttacat cgcaagcctt      3960
tgatgattat tgtatgtcaa tggggattga tgtggagcat ccagtttccc atgtgcatac      4020
acaaaatggc atggccgagt cattgataaa acagttgcag ttgattgcaa gaccgttagt      4080
cttgagaacg aagctcacaa tttatgtatg gggtcatgct atattgcatg cagctgcact      4140
ggttcggtta agaccgagtg catatcataa atactcccca ttacgattgg catctgggca      4200
agagctagat gtatcccatc tccgtgtctt tgggtgtgcg gtctatgttc cgatagcacc      4260
gccacaaaga acaaaaatgg acccacaaag gagattgaga atatatgtgg gttatacgtc      4320
accaagtata ataagatatc tggaaccagt aactggtgat atgtttatga cacgatttac      4380
caattgccat tttaatgagg atgaatttcc agcgttaggg gaaggaatta atcgaattcc      4440
taaagagatt acttggtgta caccgtcgtt gttacacttt gatcccctta cgaatcaaag      4500
agagctggaa gttcagaaaa ttgtgcattt gcataatttg gcaaacaagt taccagatgc      4560
gttcacagat aagagaaggg tgacgaagtc atgtataccc gctgaaaatg ttccatcaag      4620
agttgatgtt cctagagaac aaactgatgg aaacaaaatg agtgaacctc gagttcagtt      4680 aaagaggga aggtcagcgg gttctaaaaa taaaaatccc caaaagaaaa agaaattgga      4740
tgaacaaagt aaagttccag aagagcctga tatcgaaaaa caaaagataa tggtttaagg      4800
agatgttttt taaatgagaa tatttagttt taaaactcgt tttcagctta ttcaagttct      4860
aaagttttat tgatcttata aaaaattgaa agtttgttcg tagaaactaa ggaatgacaa      4920
tgataatgct tgttcacgtt caagtcttaa attttagaat gaaagatttg ctttcttagg      4980
ttagttatga agatgattgt cg                                               5002
```

<210> SEQ ID NO 3
<211> LENGTH: 5002
<212> TYPE: DNA
<213> ORGANISM: brassica napus

<400> SEQUENCE: 3

```
agtttgttct ctaggaacat caactcttga tggaacattt tcagcgggta tacatgactt      60
cgtcaccctt ctcttatctg tgaacgcatc tggtaacttg tttgccaaat tatgcaaatg      120
cacaattttc tgaacttcca gctctctttg attcgtaagg ggatcaaagt gtaataacga      180
cggtgtacac caagtaatct ctttaggaat tcgattaatt ccttccccta acgctggaaa      240
ttcatcctca ttaaaatggc aattggcaaa tcgtgtcgta aacatatcac cagttactgg      300
ttccagatat cttattatac ttggtgacgt ataacccaca tatattctca atctcctttg      360
tgggtccatt tttgttcttt gtggcggtgc tatcggaaca tagaccgcac acccaaagac      420
acggagatgg gatacatcta gctcttgccc agatgccaat tgtaatgggg agtatttatg      480
atatgcactc ggtcttaacc gaaccagtgc agctgcatgc aatatagcat gaccccatac      540
agaaattgtg agcttcgttc tcaagactaa cggtcttgca atcaactgca accgtttat       600 caatgactcg gccatgccat tttgtgtatg cacatgggaa actggatgct ccacatcaat      660
```

-continued

```
ccccattgac atacaataat catcaaaggc ttgcgatgta aattcaccag cattatcaag     720
ccttactttc ttaatggcat actctgagaa ctgcgttctc agctttatta tctgggcaat     780
gaactttgcg aaagccgtat ttcgtgtcgt caaaagagac acacttgacc atctactaga     840
tgcgtcaatc aataccatga aatacttaaa cggcccgcac ggtgggtgga tcggcccaca     900
tatatcacca tgtattcttt ccaaaaacat tggtgattca ttgcctactt ttgctggtga     960
tggccgagtt ataagttttc cttgagaaca tgcattacat gtaaactcgc ccgtttgcaa    1020 aattttccg tttttcaacg gatggccatt cgaatttgc actatctttc tcatcatgac    1080
tgaaccagga gtgtcctagcc tctcatgcca aattttaaat gtatcagtaa acttcatgtt    1140
taccacggca taggactcag tcatggttat tttcgtacaa tatagtccag aggataacat    1200
tcttaattct tccaatatat gtttcctctc ggacttaatg caaagaaatt caatgccatc    1260
tttactcata gtctcaatat gatatccatt tcttcggata tccttaaaac ttaataagtt    1320
tctatgagac tcgggggggat acaatgcatc acttatttca aatattgttc cccctggcat    1380
tgaaaatttc gctcttccag agcccataat aatctttgca ttactagata ttgtacttac    1440
gcttccagcg taatctttta ttttgagact ggaaaaatat ttcttatctt taattatcgt    1500
gtgcgttgac gcactatctg ccaaacacaa atctccatcc atagtctcaa agtttggcat    1560
tttctcggct ggtttaagaa cttttcggatt gataagcttc ggttggttag agcttccgga    1620
ttgatagact tcaccggtat atgagagctc gtgttgataa cgtgttgtga aataataggt    1680
gaatatttat atatgtatta ttacatatat atatatatat atatatatat atttgtttct    1740
tgtttgcaaa gtaacgtaag agagaggaat atgtgagatg atcatattat tattgttgtt    1800
ctcatatcgt tataaatgag atgaaaccac tatttatagt ggtagtaagt cggtcaaatt    1860
aactgacata agaaaagaca aaataagaaa agataaatatc tatagcaaat ggttaatcgt    1920
atcttttgat attatctcta acaattataa aaatgcttaa gggttaaaaa acaaatgggc    1980
ctatagttat agttgagggt ttgtttcatt aaaatctctt ttaaattaat taagcattcc    2040
agttttattc atctcccaat taattaactt ttttgttgac cacaaaaaca tcactcggtt    2100
aattctcaaa ttatttgaaa acaataagat caacgacttt tcacaaagta gggtgtttct    2160
tgtgtatatt gagttcagtt gaaagaccca agtaatcaag tctgggctta ttaaagcaca    2220
cgggctctac ttttttattat aaagcccaca cagaaaatgt cggagcgtga gctccacttt    2280
agttaaaagc gcgtcagaaa ataatcaaag tcaagcccaa agacgcaact tgactccgcc    2340
gtgtccattc tccgataagg tgtttttcgat tcttcttcgt ctctcttcaa gcgatcaaaa    2400
ccctaattca acccaattcg atttccacat gggtgaacct caacctcaac cccaatcacc    2460
caaacccgaa aaccgtaatc caatcccacc gcaaacaac aacgactcct cctcctcctc    2520
cgcctccgtt cccggctcaa tcgtctcatc aaccaccatc gaagccccga gaatcaccga    2580
gctaagcaat gtatcctcct cccctccttc caaaatccca ctccgtcctc gaaaaatcag    2640
aaagctttct cccaacaacg acgcggtgac gtcatcgaga ccttcagcga agggcaaacc    2700
atcgcagcca ccgaggatcc acgcaaagtc tctaacttgc gagggagagc tcgaagcggc    2760
gataacccac ctccgcagcg tcgatcctct gctagcgtcg ttgatcgacg cacacccacc    2820
gccaaagtac gagtctttca acactccctt cttggctctg atacgaagca ttctctacca    2880
gcagctagct gctaaagcgg ggaactcaat ctacacacgc ttcgtttccc tctgcgcgg    2940 cgaaaacggc gtcgttccgg agaatgtctt gcctttgacg cctcaggagc ttcgtcagat    3000
```

-continued

```
tggtgtctct gggaggaagg cgagttacct ccacgatctt gcgaggaagt atcaaaacgg     3060
gatcttgtcg gattctggga tattgaacat ggatgataag tctctgttca cgatgctgac     3120
gatggttaac gggatcggtt cgtggtcggt tcatatgttt atgatgaact cgcttcatag     3180
acctgatgtg ttgcctgtta acgatcttgg tgtgaggaaa ggtgtgcaga tgctttatga     3240
cttgccagag ttgcctcgtc cttcgcagat ggagggtctt tgcgagaagt ggcgtccgta     3300
taggtctgtt gggtcgtggt acatgtggcg gctcattgaa gctaaaggga ctccgtcgaa     3360
tgctggagcg gtgagttcag gagctgattt ggcgtttccg cagttggaag acttgcaaca     3420
gcaacatcag caacaacagt cacagcttct ggaccctctt agtgtgttca gtatcgggta     3480
tagtcagcta ctgtatctaa cgtagtttct ctgcaatact tgtccctgct tttaccttgc     3540
ttgaagtttg cccttaaggt agatatagca gtcactggag tggttgcctt atagatggta     3600
ctttctgaaa acgagtacta acgtctagtt atcgtttcct taagttaatc tcaatgcttc     3660
aaggtattta gctttaactg tagatgcaat tgtcaagggg attgtggtta agatagtttt     3720
tagtttattt tgtcatctaa aacttgtatc gagctgacaa gtcgcatgaa aaaataccat     3780
agtttcgtgg agtttagtat gttcaagagt agcatctatg cagggaatgt gtattgaggc     3840
tggttttcat ggcttgatag acgtatggat attaattgat agactttttca tgtggagtcc     3900 ttcgctttc aacgtaatca catgtgcggc agtgaaagcc ttcactaaaa caagatcatg     3960
ttgaagaaaa tggtgcatag gggttctaat atttgatact ttgcgtacct taggtactaa     4020
tgtttcacgt gacaacgtta aaatgtggaa aactcaagtg aaagtgaata gtttgcagtg     4080
ggttttaacc atcacaacat aataactgaa gcttttctca tccaagtcac tatacttttg     4140
taatgctaaa tacttggttt gttaattaag gagtaattac aattataacg aggttgttga     4200
tacattagtc ttcttatgcg gttcttattg actacttaac agggcatggg gccaaactta     4260
gctggcttcc caccataagt tgttgtcgtc catggcgtta gagggattct ggtccagtct     4320
tcagatactg tcagatgaaa aggtcgagtc tgctgtgaag aaatacgaat aaagcaggaa     4380
ctttgtaggt tgggtttctt aagacacaaa actgaaagac tatgcagcag aaaccctctt     4440
agtatgtaag atatagttta gctgatgaac tttgattttc tcttgttgga gacttaaaat     4500
tgctgtttaa aaaaactcat aattcatgta aaacagagtc aaatctttca ttttctcatt     4560
gcttaaccag ttgtttgcg ggcataatct tctttgcata atcttcttac aatttttttt     4620
tactaatgaa ttttcgcacg cgtaaatata ttttttttcca aatatttatt agtttatgtt     4680
ttattaattt gaaattagca ttttatgtt ccaaaatttt taaatcaaac atcaaattac     4740
ttatatataa aaaagaattc actaaaatat atatgttcac atattaaaaa tattttagaa     4800
aatgttttta tacaaatgat ttttttaatt aataattaat tataatttgt tttatatatt     4860 aatttttaaaa aatttcataa tagaaaatat tatttcaaga taacaacaca attaagattt     4920
aggaaaaatt ggcaaattgg gcaaattgca agtttgatat tagggagttg gacgacctcg     4980
agtttaaatt agaagattgg ac     5002
```

```
<210> SEQ ID NO 4
<211> LENGTH: 5002
<212> TYPE: DNA
<213> ORGANISM: brassica napus

<400> SEQUENCE: 4
acaaaaaaaa aagtcattta gcatcattta atttatattt ttgcattagt tataaatgat      60
gtaaaataat tttacatcac ttaaataaat gactctgaaa gtggtgatac aaataattta     120
```

```
catcatttta ttaacaaatg atgtaagaaa ttattatatt ttcatcagtt actttatgtg      180
atgtcaatat atatatcaat tgtaaaaacg atattaacaa ttacatcaat ttttccaaat      240
gatattagta ttgacatcaa ttaaaataac tgatttagtt aataaaatat taattaataa      300
tttaataaat taatatcgat ttattaaaaa atattttaat agtttactta tttatagtta      360 ttgtttaaa  tattagaatc atttgtagag tagaaaatac atataaaata aaatattatt      420
ttgtaacaat ttattaattt tccattgaaa tataacatag ccaagaaaac aagaaaaata      480
aaaaaggtac agagaagaaa aaaagaatat agaaagttaa acaaattact agttatgaga      540
aagaaaaaaa catgaagaat gcggagatac aaaaaaaata ctagcaatta tatccagatt      600
cttctttttt cttctcattc tttgcatctt cttttttcat cttcaatctc tatcgatttt      660
cctccacatt tcaaatcact cttgtcgtgt cttcatatat ctctgaatta ttctgatcct      720
aatagagaat gattattaag acataaacaa aaaatataag aacttgtagt tttcaaaaaa      780
tttgagaata gagaaagaaa aaagaaataa tacctctcaa aagtttaatc agagtcgttt      840
gattagcaaa cttcagcaat ctttaaaccc tttcatgaaa agaaacgcat ttgtcatcgt      900
gactcatata atgcttgata ttgttgaaat ctgtttctga tcaaataacc aaaacaacaa      960
attttaagct ctgaacaaaa gtttaagaaa ctgaaacaga gaaaaaatga aaaagagacg     1020
aagatgaaaa tattgaagtg aaacagttat agaaaattat gatccagtaa aattaaagct     1080
aacaaaaaat taaaatcaca agaatattat actatttctg gtattcccta cttttttaact     1140 gattagttca cgttttatgt gggattgtgg ttcctttttt tggggaacta taatagatcc     1200
tgtttagtat ataattatac aattatatta tatttattaa ttattttata gatccaaact     1260
aattttgtac tagataatat atttcaacag atgcaaaata agattaaaaa caatatcatt     1320
tttattagac cgatgctaat atatatatat atatatatat aattttttatt agcatcaatt     1380 attttactga tgtaaattat agatcatttta aataagtgat actaaacaaa ataatatatg     1440
catcaattgt gtaattgata taattttata taattgtatc attttttgtta aaatgataca     1500 aattaaaaga aaagacatca cttatatcga actgatgtta aattaattaa taataacatc     1560
aattactata aatgatttaa aagtataaat atttgtttca gttctgaata agtgatttaa     1620
aatggtatca cttattttttg tgatacaatt taagtgatac aattcaatgt ttttttttgta     1680 gtgaatagtc cttcccatcg ccattgtata ttttattctt taatccttat aataaaatta     1740
aacataacat tactcagtaa agtctcaaat tatatgaaaa caatagatca agactcttgg     1800
aaaagtattt aattgttatt tatttcacaa agaagggtct aactcaagca ttccagtttc     1860
ggcttattca tcacccaatt aattaagggc ttatttgctg aatagccaaa aaaaaagtga     1920
aattagattt ttagagagag agagagtaga gagagatagg aagagaaagt aggagagagg     1980
gggtgttttt agttagttag tgaattttgt ttttttgtgt gtatattgga tgcaatttcc     2040
cattaattaa ctcttttgtt gaccacaaaa acatcactca gttaattctc aaattatatg     2100
aaaacaatag atcaacgact tttcccccca gttttcagag ggagttttaa tcaactttta     2160
tttactttgt aactatttta aatttaacaa agtaaggtgt ttcttgtgta tattgagctc     2220
agttgaaaga cccaagtaat ccagtttggg cttattaaag caaacggact ctactttttt     2280
atcataaagc ccacacagaa gacatcggag cgtgaaggcc actatagtta aaagcgcgtc     2340
agaaaagaat caaagtcaag ccaaaagacg caacttcact ccgccgtgtc cattctccga     2400
ttacttcttc aagcgatcaa acaaaaccct aattcaaccc aattcgattt tccacatggg     2460
```

-continued

```
tgaaccacaa ccttctcaac caccgcaaag caacgattcc gacgactcct cctccgcctc   2520
cgttcccggc tcaatcgtct catcaaccac catcgaagcc ccgagaatca ccgagctaag   2580
caatgtatcc tcccctcctt ccaaaatccc tctccgtcct cgaaaaatca gaaagctttc   2640
tcccaacaac gacgcgagac cttcaccgaa gggcaaacca tcgcagccac cgaggatcca   2700
cgcaaagtct ctaacttgcg agggagagct cgaagcggcg attacccacc tccgcagcgt   2760
cgatcctctc ctagcctcgt tgatcgacgc acacccaccg ccaaagtacg agtctttcaa   2820
cactcccttc ttggctctca tccgaagcat cctctaccag cagcttgctg ccaaagcggg   2880
gaactcaatc tacacacgct tcgtttccct ctgcggcggc gaaaacggcg tcgttccgga   2940
gaatgtcttg cctttgacgc ctcaggagct tcgtcagatt ggtgtctctg ggaggaaggc   3000
gagttacctc cacgatcttg cgaggaagta tcaaaacggg atcttgtcgg attctgggat   3060
attgaacatg gatgataagt ctctgttcac gatgctgacg atggttaacg ggatcggttc   3120
gtggtcggtt catatgttta tgatgaactc gcttcataga cctgatgtgt tgcctgttaa   3180
cgatcttggt gtgaggaaag gtgtgcagat gctttatgac ttgccagagt tgcctcgtcc   3240
ttcgcagatg gagggtcttt gcgagaagtg gcgtccgtat aggtctgttg ggtcgtggta   3300
catgtggcgg ctcattgaag ctaaagggac tccgtcgaat gctggagcgg tgagttcagg   3360
agctgatttg gcgtttccgc agttggaaga cttgcaacag caacatcagc aacaacagtc   3420
acagcttctg gaccctctta gtgtgttcag tatcgggtat agtcagctac tgtatctaac   3480
gtagtttctc tgcaatactt gtccctgctt ttaccttgct tgaagtttgc ccttaaggta   3540
gatatagcag tcactggagt ggttgcctta tagatggtac tttctgaaaa cgagtactaa   3600
cgtctagtta tcgtttcctt aagttaatct caatgcttca aggtatttag ctttaactgt   3660
agatgcaatt gtcaagggga ttgtggttaa gatagttttt agtttatttt gtcatctaaa   3720
acttgtatcg agctgacaag tcgcatgaaa aaataccata gtttcgtgga gtttagtatg   3780
ttcaagagta gcatctatgc agggaatgtg tattgaggct ggttttcatg gcttgataga   3840
cgtatggata ttaattgata gacttttcat gtggagtcct tcgcttttca acgtaatcac   3900
atgtgcggca gtgaaagcct tcactaaaac aagatcatgt tgaagaaaat ggtgcatagg   3960
ggttctaata tttgatactt tgcgtacctt aggtactaat gtttcacgtg acaacgttaa   4020
aatgtggaaa actcaagtga aagtgaatag tttgcagtgg gtttttaacca tcacaacata   4080 ataactgaag ctttttctcat ccaagtcact atactttgt aatgctaaat acttggtttg   4140
ttaattaagg agtaattaca attataacga ggttgttgat acattagtct tcttatgcgg   4200
ttcttattga ctacttaaca gggcatgggg ccaaacttag ctggcttccc accataagtt   4260
gttgtcgtcc atggcgttag agggattctg gtccagtctt cagatactgt cagatgaaaa   4320
ggtcgagtct gctgtgaaga aatacgaata aagcaggaac tttgtaggtt gggtttctta   4380
agacacaaaa ctgaaagact atgcagcaga aaccctctta gtatgtaaga tatagtttag   4440
ctgatgaact ttgattttct cttgttggag acttaaaatt gctgtttaaa aaaactcata   4500
attcatgtaa aacagagtca aatctttcat tttctcattg cttaaccagt tgttttgcgg   4560
gcataatctt ctttgcataa tcttcttaca attttttttt actaatgaat tttcgcacgc   4620
gtaaatatat ttttttccaa atatttatta gtttatgttt tattaatttg aaattagcat   4680
tttatgtttc caaaatttt aaatcaaaca tcaaattact tatatataaa aaagaattca   4740
ctaaaatata tatgttcaca tattaaaaat attttagaaa atgttttat acaaatgatt   4800 tttttaatta ataattaatt ataatttgtt ttatatatta attttaaaaa atttcataat   4860
```

-continued agaaaatatt atttcaagat aacaacacaa ttaagattta ggaaaaattg gcaaattggg     4920
caaattgcaa gtttgatatt agggagttgg acgacctcga gtttaaatta gaagattgga     4980
cgaatcgcct tttccagact tg                                              5002

<210> SEQ ID NO 5
<211> LENGTH: 26
<212> TYPE: DNA
<213> ORGANISM: brassica napus

<400> SEQUENCE: 5
tttaacaaag taaggtgttt cttgtg                                            26

<210> SEQ ID NO 6
<211> LENGTH: 20
<212> TYPE: DNA
<213> ORGANISM: brassica napus

<400> SEQUENCE: 6
ttaagccaac atgtgcagga                                                   20

<210> SEQ ID NO 7
<211> LENGTH: 22
<212> TYPE: DNA
<213> ORGANISM: brassica napus

<400> SEQUENCE: 7
agcgactttt cacaaagtag gg                                                22

<210> SEQ ID NO 8
<211> LENGTH: 20
<212> TYPE: DNA
<213> ORGANISM: brassica napus

<400> SEQUENCE: 8
tgatggttaa aacccactgc                                                   20

<210> SEQ ID NO 9
<211> LENGTH: 23
<212> TYPE: DNA
<213> ORGANISM: brassica napus

<400> SEQUENCE: 9
caacgacttt tcacaaagta ggg                                               23

<210> SEQ ID NO 10
<211> LENGTH: 25
<212> TYPE: DNA
<213> ORGANISM: brassica napus

<400> SEQUENCE: 10
gcctcagtta ttatgtttgt gatgg                                             25

<210> SEQ ID NO 11
<211> LENGTH: 21
<212> TYPE: DNA
<213> ORGANISM: brassica napus

<400> SEQUENCE: 11
gtgatggtta aaacccactg c                                                 21

<210> SEQ ID NO 12

-continued

```
<211> LENGTH: 26
<212> TYPE: DNA
<213> ORGANISM: brassica napus

<400> SEQUENCE: 12
tttaacaaag taaggtgttt cttgtg                                                26

<210> SEQ ID NO 13
<211> LENGTH: 24
<212> TYPE: DNA
<213> ORGANISM: brassica napus

<400> SEQUENCE: 13
gtccgtttgc tttaataagc ccaa                                                  24

<210> SEQ ID NO 14
<211> LENGTH: 24
<212> TYPE: DNA
<213> ORGANISM: brassica napus

<400> SEQUENCE: 14
tcccgtgtgc tttaataagc ccag                                                  24

<210> SEQ ID NO 15
<211> LENGTH: 21
<212> TYPE: DNA
<213> ORGANISM: brassica napus

<400> SEQUENCE: 15
agatcagcga cttttcacaa a                                                     21

<210> SEQ ID NO 16
<211> LENGTH: 21
<212> TYPE: DNA
<213> ORGANISM: brassica napus

<400> SEQUENCE: 16
ccagttttca gagggagttt t                                                     21

<210> SEQ ID NO 17
<211> LENGTH: 21
<212> TYPE: DNA
<213> ORGANISM: brassica napus

<400> SEQUENCE: 17
ccagttttca gagggagttt t                                                     21

<210> SEQ ID NO 18
<211> LENGTH: 21
<212> TYPE: DNA
<213> ORGANISM: brassica napus

<400> SEQUENCE: 18
ggaggaggag gaggagtcgt t                                                     21

<210> SEQ ID NO 19
<211> LENGTH: 25
<212> TYPE: DNA
<213> ORGANISM: brassica napus

<400> SEQUENCE: 19
gggattggat tacggttttc gggtt                                                 25
```

-continued

```
<210> SEQ ID NO 20
<211> LENGTH: 24
<212> TYPE: DNA
<213> ORGANISM: brassica napus

<400> SEQUENCE: 20
attttccaca tgggtgaacc acaa                                      24

<210> SEQ ID NO 21
<211> LENGTH: 13
<212> TYPE: DNA
<213> ORGANISM: brassica napus

<400> SEQUENCE: 21
ggaggaggag gag                                                  13

<210> SEQ ID NO 22
<211> LENGTH: 13
<212> TYPE: DNA
<213> ORGANISM: brassica napus

<400> SEQUENCE: 22
ggagtcgttg ttg                                                  13

<210> SEQ ID NO 23
<211> LENGTH: 13
<212> TYPE: DNA
<213> ORGANISM: brassica napus

<400> SEQUENCE: 23
gagtcgttgt tgt                                                  13

<210> SEQ ID NO 24
<211> LENGTH: 13
<212> TYPE: DNA
<213> ORGANISM: brassica napus

<400> SEQUENCE: 24
agtcgttgtt gtt                                                  13

<210> SEQ ID NO 25
<211> LENGTH: 13
<212> TYPE: DNA
<213> ORGANISM: brassica napus

<400> SEQUENCE: 25
gtcgttgttg ttt                                                  13

<210> SEQ ID NO 26
<211> LENGTH: 13
<212> TYPE: DNA
<213> ORGANISM: brassica napus

<400> SEQUENCE: 26
tcgttgttgt ttt                                                  13

<210> SEQ ID NO 27
<211> LENGTH: 13
<212> TYPE: DNA
<213> ORGANISM: brassica napus

<400> SEQUENCE: 27
cgttgttgtt ttg                                                  13
```

-continued

```
<210> SEQ ID NO 28
<211> LENGTH: 13
<212> TYPE: DNA
<213> ORGANISM: brassica napus

<400> SEQUENCE: 28
gttgttgttt tgc                                                    13

<210> SEQ ID NO 29
<211> LENGTH: 13
<212> TYPE: DNA
<213> ORGANISM: brassica napus

<400> SEQUENCE: 29
ttgttgtttt gcg                                                    13

<210> SEQ ID NO 30
<211> LENGTH: 13
<212> TYPE: DNA
<213> ORGANISM: brassica napus

<400> SEQUENCE: 30
tgttgttttg cgg                                                    13

<210> SEQ ID NO 31
<211> LENGTH: 13
<212> TYPE: DNA
<213> ORGANISM: brassica napus

<400> SEQUENCE: 31
gttgttttgc ggt                                                    13

<210> SEQ ID NO 32
<211> LENGTH: 13
<212> TYPE: DNA
<213> ORGANISM: brassica napus

<400> SEQUENCE: 32
gaggaggagg agt                                                    13

<210> SEQ ID NO 33
<211> LENGTH: 13
<212> TYPE: DNA
<213> ORGANISM: brassica napus

<400> SEQUENCE: 33
ttgttttgcg gtg                                                    13

<210> SEQ ID NO 34
<211> LENGTH: 13
<212> TYPE: DNA
<213> ORGANISM: brassica napus

<400> SEQUENCE: 34
tgttttgcgg tgg                                                    13

<210> SEQ ID NO 35
<211> LENGTH: 13
<212> TYPE: DNA
<213> ORGANISM: brassica napus

<400> SEQUENCE: 35
gttttgcggt ggg                                                    13
```

-continued

```
<210> SEQ ID NO 36
<211> LENGTH: 13
<212> TYPE: DNA
<213> ORGANISM: brassica napus

<400> SEQUENCE: 36
aggaggagga gtc                                                        13

<210> SEQ ID NO 37
<211> LENGTH: 13
<212> TYPE: DNA
<213> ORGANISM: brassica napus

<400> SEQUENCE: 37
ggaggaggag tcg                                                        13

<210> SEQ ID NO 38
<211> LENGTH: 13
<212> TYPE: DNA
<213> ORGANISM: brassica napus

<400> SEQUENCE: 38
gaggaggagt cgt                                                        13

<210> SEQ ID NO 39
<211> LENGTH: 13
<212> TYPE: DNA
<213> ORGANISM: brassica napus

<400> SEQUENCE: 39
aggaggagtc gtt                                                        13

<210> SEQ ID NO 40
<211> LENGTH: 13
<212> TYPE: DNA
<213> ORGANISM: brassica napus

<400> SEQUENCE: 40
ggaggagtcg ttg                                                        13

<210> SEQ ID NO 41
<211> LENGTH: 13
<212> TYPE: DNA
<213> ORGANISM: brassica napus

<400> SEQUENCE: 41
gaggagtcgt tgt                                                        13

<210> SEQ ID NO 42
<211> LENGTH: 13
<212> TYPE: DNA
<213> ORGANISM: brassica napus

<400> SEQUENCE: 42
aggagtcgtt gtt                                                        13

<210> SEQ ID NO 43
<211> LENGTH: 14
<212> TYPE: DNA
<213> ORGANISM: brassica napus

<400> SEQUENCE: 43
```

-continued

```
ggaggaggag gagt                                                14

<210> SEQ ID NO 44
<211> LENGTH: 14
<212> TYPE: DNA
<213> ORGANISM: brassica napus

<400> SEQUENCE: 44
ggagtcgttg ttgt                                                14

<210> SEQ ID NO 45
<211> LENGTH: 14
<212> TYPE: DNA
<213> ORGANISM: brassica napus

<400> SEQUENCE: 45
gagtcgttgt tgtt                                                14

<210> SEQ ID NO 46
<211> LENGTH: 14
<212> TYPE: DNA
<213> ORGANISM: brassica napus

<400> SEQUENCE: 46
agtcgttgtt gttt                                                14

<210> SEQ ID NO 47
<211> LENGTH: 14
<212> TYPE: DNA
<213> ORGANISM: brassica napus

<400> SEQUENCE: 47
gtcgttgttg tttt                                                14

<210> SEQ ID NO 48
<211> LENGTH: 14
<212> TYPE: DNA
<213> ORGANISM: brassica napus

<400> SEQUENCE: 48
tcgttgttgt tttg                                                14

<210> SEQ ID NO 49
<211> LENGTH: 14
<212> TYPE: DNA
<213> ORGANISM: brassica napus

<400> SEQUENCE: 49
cgttgttgtt ttgc                                                14

<210> SEQ ID NO 50
<211> LENGTH: 14
<212> TYPE: DNA
<213> ORGANISM: brassica napus

<400> SEQUENCE: 50
gttgttgttt tgcg                                                14

<210> SEQ ID NO 51
<211> LENGTH: 14
<212> TYPE: DNA
<213> ORGANISM: brassica napus

<400> SEQUENCE: 51
```
ttgttgtttt gcgg                                                    14

<210> SEQ ID NO 52
<211> LENGTH: 14
<212> TYPE: DNA
<213> ORGANISM: brassica napus

<400> SEQUENCE: 52
tgttgttttg cggt                                                    14

<210> SEQ ID NO 53
<211> LENGTH: 14
<212> TYPE: DNA
<213> ORGANISM: brassica napus

<400> SEQUENCE: 53
gttgttttgc ggtg                                                    14

<210> SEQ ID NO 54
<211> LENGTH: 14
<212> TYPE: DNA
<213> ORGANISM: brassica napus

<400> SEQUENCE: 54
gaggaggagg agtc                                                    14

<210> SEQ ID NO 55
<211> LENGTH: 14
<212> TYPE: DNA
<213> ORGANISM: brassica napus

<400> SEQUENCE: 55
ttgttttgcg gtgg                                                    14

<210> SEQ ID NO 56
<211> LENGTH: 14
<212> TYPE: DNA
<213> ORGANISM: brassica napus

<400> SEQUENCE: 56
tgttttgcgg tggg                                                    14

<210> SEQ ID NO 57
<211> LENGTH: 14
<212> TYPE: DNA
<213> ORGANISM: brassica napus

<400> SEQUENCE: 57
aggaggagga gtcg                                                    14

<210> SEQ ID NO 58
<211> LENGTH: 14
<212> TYPE: DNA
<213> ORGANISM: brassica napus

<400> SEQUENCE: 58
ggaggaggag tcgt                                                    14

<210> SEQ ID NO 59
<211> LENGTH: 14
<212> TYPE: DNA
<213> ORGANISM: brassica napus

<400> SEQUENCE: 59
gaggaggagt cgtt                                                  14

<210> SEQ ID NO 60
<211> LENGTH: 14
<212> TYPE: DNA
<213> ORGANISM: brassica napus

<400> SEQUENCE: 60
aggaggagtc gttg                                                  14

<210> SEQ ID NO 61
<211> LENGTH: 14
<212> TYPE: DNA
<213> ORGANISM: brassica napus

<400> SEQUENCE: 61
ggaggagtcg ttgt                                                  14

<210> SEQ ID NO 62
<211> LENGTH: 14
<212> TYPE: DNA
<213> ORGANISM: brassica napus

<400> SEQUENCE: 62
gaggagtcgt tgtt                                                  14

<210> SEQ ID NO 63
<211> LENGTH: 14
<212> TYPE: DNA
<213> ORGANISM: brassica napus

<400> SEQUENCE: 63
aggagtcgtt gttg                                                  14

<210> SEQ ID NO 64
<211> LENGTH: 15
<212> TYPE: DNA
<213> ORGANISM: brassica napus

<400> SEQUENCE: 64
ggaggaggag gagtc                                                 15

<210> SEQ ID NO 65
<211> LENGTH: 15
<212> TYPE: DNA
<213> ORGANISM: brassica napus

<400> SEQUENCE: 65
ggagtcgttg ttgtt                                                 15

<210> SEQ ID NO 66
<211> LENGTH: 15
<212> TYPE: DNA
<213> ORGANISM: brassica napus

<400> SEQUENCE: 66
gagtcgttgt tgttt                                                 15

<210> SEQ ID NO 67
<211> LENGTH: 15
<212> TYPE: DNA
<213> ORGANISM: brassica napus

<400> SEQUENCE: 67
agtcgttgtt gtttt                                                  15

<210> SEQ ID NO 68
<211> LENGTH: 15
<212> TYPE: DNA
<213> ORGANISM: brassica napus

<400> SEQUENCE: 68
gtcgttgttg ttttg                                                  15

<210> SEQ ID NO 69
<211> LENGTH: 15
<212> TYPE: DNA
<213> ORGANISM: brassica napus

<400> SEQUENCE: 69
tcgttgttgt tttgc                                                  15

<210> SEQ ID NO 70
<211> LENGTH: 15
<212> TYPE: DNA
<213> ORGANISM: brassica napus

<400> SEQUENCE: 70
cgttgttgtt ttgcg                                                  15

<210> SEQ ID NO 71
<211> LENGTH: 15
<212> TYPE: DNA
<213> ORGANISM: brassica napus

<400> SEQUENCE: 71
gttgttgttt tgcgg                                                  15

<210> SEQ ID NO 72
<211> LENGTH: 15
<212> TYPE: DNA
<213> ORGANISM: brassica napus

<400> SEQUENCE: 72
ttgttgtttt gcggt                                                  15

<210> SEQ ID NO 73
<211> LENGTH: 15
<212> TYPE: DNA
<213> ORGANISM: brassica napus

<400> SEQUENCE: 73
tgttgttttg cggtg                                                  15

<210> SEQ ID NO 74
<211> LENGTH: 15
<212> TYPE: DNA
<213> ORGANISM: brassica napus

<400> SEQUENCE: 74
gttgttttgc ggtgg                                                  15

<210> SEQ ID NO 75
<211> LENGTH: 15
<212> TYPE: DNA

<213> ORGANISM: brassica napus

<400> SEQUENCE: 75
gaggaggagg agtcg                                                                   15

<210> SEQ ID NO 76
<211> LENGTH: 15
<212> TYPE: DNA
<213> ORGANISM: brassica napus

<400> SEQUENCE: 76
ttgttttgcg gtggg                                                                   15

<210> SEQ ID NO 77
<211> LENGTH: 15
<212> TYPE: DNA
<213> ORGANISM: brassica napus

<400> SEQUENCE: 77
aggaggagga gtcgt                                                                   15

<210> SEQ ID NO 78
<211> LENGTH: 15
<212> TYPE: DNA
<213> ORGANISM: brassica napus

<400> SEQUENCE: 78
ggaggaggag tcgtt                                                                   15

<210> SEQ ID NO 79
<211> LENGTH: 15
<212> TYPE: DNA
<213> ORGANISM: brassica napus

<400> SEQUENCE: 79
gaggaggagt cgttg                                                                   15

<210> SEQ ID NO 80
<211> LENGTH: 15
<212> TYPE: DNA
<213> ORGANISM: brassica napus

<400> SEQUENCE: 80
aggaggagtc gttgt                                                                   15

<210> SEQ ID NO 81
<211> LENGTH: 15
<212> TYPE: DNA
<213> ORGANISM: brassica napus

<400> SEQUENCE: 81
ggaggagtcg ttgtt                                                                   15

<210> SEQ ID NO 82
<211> LENGTH: 15
<212> TYPE: DNA
<213> ORGANISM: brassica napus

<400> SEQUENCE: 82
gaggagtcgt tgttg                                                                   15

<210> SEQ ID NO 83
<211> LENGTH: 15

<212> TYPE: DNA
<213> ORGANISM: brassica napus

<400> SEQUENCE: 83
aggagtcgtt gttgt                                                                    15

<210> SEQ ID NO 84
<211> LENGTH: 16
<212> TYPE: DNA
<213> ORGANISM: brassica napus

<400> SEQUENCE: 84
ggaggaggag gagtcg                                                                   16

<210> SEQ ID NO 85
<211> LENGTH: 16
<212> TYPE: DNA
<213> ORGANISM: brassica napus

<400> SEQUENCE: 85
ggagtcgttg ttgttt                                                                   16

<210> SEQ ID NO 86
<211> LENGTH: 16
<212> TYPE: DNA
<213> ORGANISM: brassica napus

<400> SEQUENCE: 86
gagtcgttgt tgtttt                                                                   16

<210> SEQ ID NO 87
<211> LENGTH: 16
<212> TYPE: DNA
<213> ORGANISM: brassica napus

<400> SEQUENCE: 87
agtcgttgtt gttttg                                                                   16

<210> SEQ ID NO 88
<211> LENGTH: 16
<212> TYPE: DNA
<213> ORGANISM: brassica napus

<400> SEQUENCE: 88
gtcgttgttg ttttgc                                                                   16

<210> SEQ ID NO 89
<211> LENGTH: 16
<212> TYPE: DNA
<213> ORGANISM: brassica napus

<400> SEQUENCE: 89
tcgttgttgt tttgcg                                                                   16

<210> SEQ ID NO 90
<211> LENGTH: 16
<212> TYPE: DNA
<213> ORGANISM: brassica napus

<400> SEQUENCE: 90
cgttgttgtt ttgcgg                                                                   16

<210> SEQ ID NO 91

-continued

```
<211> LENGTH: 16
<212> TYPE: DNA
<213> ORGANISM: brassica napus

<400> SEQUENCE: 91
gttgttgttt tgcggt                                                    16

<210> SEQ ID NO 92
<211> LENGTH: 16
<212> TYPE: DNA
<213> ORGANISM: brassica napus

<400> SEQUENCE: 92
ttgttgtttt gcggtg                                                    16

<210> SEQ ID NO 93
<211> LENGTH: 16
<212> TYPE: DNA
<213> ORGANISM: brassica napus

<400> SEQUENCE: 93
tgttgttttg cggtgg                                                    16

<210> SEQ ID NO 94
<211> LENGTH: 16
<212> TYPE: DNA
<213> ORGANISM: brassica napus

<400> SEQUENCE: 94
gttgttttgc ggtggg                                                    16

<210> SEQ ID NO 95
<211> LENGTH: 16
<212> TYPE: DNA
<213> ORGANISM: brassica napus

<400> SEQUENCE: 95
gaggaggagg agtcgt                                                    16

<210> SEQ ID NO 96
<211> LENGTH: 16
<212> TYPE: DNA
<213> ORGANISM: brassica napus

<400> SEQUENCE: 96
aggaggagga gtcgtt                                                    16

<210> SEQ ID NO 97
<211> LENGTH: 16
<212> TYPE: DNA
<213> ORGANISM: brassica napus

<400> SEQUENCE: 97
ggaggaggag tcgttg                                                    16

<210> SEQ ID NO 98
<211> LENGTH: 16
<212> TYPE: DNA
<213> ORGANISM: brassica napus

<400> SEQUENCE: 98
gaggaggagt cgttgt                                                    16
```

-continued

```
<210> SEQ ID NO 99
<211> LENGTH: 16
<212> TYPE: DNA
<213> ORGANISM: brassica napus

<400> SEQUENCE: 99
aggaggagtc gttgtt                                                      16

<210> SEQ ID NO 100
<211> LENGTH: 16
<212> TYPE: DNA
<213> ORGANISM: brassica napus

<400> SEQUENCE: 100
ggaggagtcg ttgttg                                                      16

<210> SEQ ID NO 101
<211> LENGTH: 16
<212> TYPE: DNA
<213> ORGANISM: brassica napus

<400> SEQUENCE: 101
gaggagtcgt tgttgt                                                      16

<210> SEQ ID NO 102
<211> LENGTH: 16
<212> TYPE: DNA
<213> ORGANISM: brassica napus

<400> SEQUENCE: 102
aggagtcgtt gttgtt                                                      16

<210> SEQ ID NO 103
<211> LENGTH: 17
<212> TYPE: DNA
<213> ORGANISM: brassica napus

<400> SEQUENCE: 103
ggaggaggag gagtcgt                                                     17

<210> SEQ ID NO 104
<211> LENGTH: 17
<212> TYPE: DNA
<213> ORGANISM: brassica napus

<400> SEQUENCE: 104
ggagtcgttg ttgtttt                                                     17

<210> SEQ ID NO 105
<211> LENGTH: 17
<212> TYPE: DNA
<213> ORGANISM: brassica napus

<400> SEQUENCE: 105
gagtcgttgt tgttttg                                                     17

<210> SEQ ID NO 106
<211> LENGTH: 17
<212> TYPE: DNA
<213> ORGANISM: brassica napus

<400> SEQUENCE: 106
agtcgttgtt gttttgc                                                     17
```

-continued

<210> SEQ ID NO 107
<211> LENGTH: 17
<212> TYPE: DNA
<213> ORGANISM: brassica napus

<400> SEQUENCE: 107
gtcgttgttg ttttgcg                                                  17

<210> SEQ ID NO 108
<211> LENGTH: 17
<212> TYPE: DNA
<213> ORGANISM: brassica napus

<400> SEQUENCE: 108
tcgttgttgt tttgcgg                                                  17

<210> SEQ ID NO 109
<211> LENGTH: 17
<212> TYPE: DNA
<213> ORGANISM: brassica napus

<400> SEQUENCE: 109
cgttgttgtt ttgcggt                                                  17

<210> SEQ ID NO 110
<211> LENGTH: 17
<212> TYPE: DNA
<213> ORGANISM: brassica napus

<400> SEQUENCE: 110
gttgttgttt tgcggtg                                                  17

<210> SEQ ID NO 111
<211> LENGTH: 17
<212> TYPE: DNA
<213> ORGANISM: brassica napus

<400> SEQUENCE: 111
ttgttgtttt gcggtgg                                                  17

<210> SEQ ID NO 112
<211> LENGTH: 17
<212> TYPE: DNA
<213> ORGANISM: brassica napus

<400> SEQUENCE: 112
tgttgttttg cggtggg                                                  17

<210> SEQ ID NO 113
<211> LENGTH: 17
<212> TYPE: DNA
<213> ORGANISM: brassica napus

<400> SEQUENCE: 113
gaggaggagg agtcgtt                                                  17

<210> SEQ ID NO 114
<211> LENGTH: 17
<212> TYPE: DNA
<213> ORGANISM: brassica napus

<400> SEQUENCE: 114
aggaggagga gtcgttg                                                  17

-continued

```
<210> SEQ ID NO 115
<211> LENGTH: 17
<212> TYPE: DNA
<213> ORGANISM: brassica napus

<400> SEQUENCE: 115
ggaggaggag tcgttgt                                                    17

<210> SEQ ID NO 116
<211> LENGTH: 17
<212> TYPE: DNA
<213> ORGANISM: brassica napus

<400> SEQUENCE: 116
gaggaggagt cgttgtt                                                    17

<210> SEQ ID NO 117
<211> LENGTH: 17
<212> TYPE: DNA
<213> ORGANISM: brassica napus

<400> SEQUENCE: 117
aggaggagtc gttgttg                                                    17

<210> SEQ ID NO 118
<211> LENGTH: 17
<212> TYPE: DNA
<213> ORGANISM: brassica napus

<400> SEQUENCE: 118
ggaggagtcg ttgttgt                                                    17

<210> SEQ ID NO 119
<211> LENGTH: 17
<212> TYPE: DNA
<213> ORGANISM: brassica napus

<400> SEQUENCE: 119
gaggagtcgt tgttgtt                                                    17

<210> SEQ ID NO 120
<211> LENGTH: 17
<212> TYPE: DNA
<213> ORGANISM: brassica napus

<400> SEQUENCE: 120
aggagtcgtt gttgttt                                                    17

<210> SEQ ID NO 121
<211> LENGTH: 18
<212> TYPE: DNA
<213> ORGANISM: brassica napus

<400> SEQUENCE: 121
ggaggaggag gagtcgtt                                                   18

<210> SEQ ID NO 122
<211> LENGTH: 18
<212> TYPE: DNA
<213> ORGANISM: brassica napus

<400> SEQUENCE: 122
```

-continued

```
ggagtcgttg ttgttttg                                              18

<210> SEQ ID NO 123
<211> LENGTH: 18
<212> TYPE: DNA
<213> ORGANISM: brassica napus

<400> SEQUENCE: 123
gagtcgttgt tgttttgc                                              18

<210> SEQ ID NO 124
<211> LENGTH: 18
<212> TYPE: DNA
<213> ORGANISM: brassica napus

<400> SEQUENCE: 124
agtcgttgtt gttttgcg                                              18

<210> SEQ ID NO 125
<211> LENGTH: 18
<212> TYPE: DNA
<213> ORGANISM: brassica napus

<400> SEQUENCE: 125
tcgttgttgt tttgcggt                                              18

<210> SEQ ID NO 126
<211> LENGTH: 18
<212> TYPE: DNA
<213> ORGANISM: brassica napus

<400> SEQUENCE: 126
cgttgttgtt ttgcggtg                                              18

<210> SEQ ID NO 127
<211> LENGTH: 18
<212> TYPE: DNA
<213> ORGANISM: brassica napus

<400> SEQUENCE: 127
gttgttgttt tgcggtgg                                              18

<210> SEQ ID NO 128
<211> LENGTH: 18
<212> TYPE: DNA
<213> ORGANISM: brassica napus

<400> SEQUENCE: 128
ttgttgtttt gcggtggg                                              18

<210> SEQ ID NO 129
<211> LENGTH: 18
<212> TYPE: DNA
<213> ORGANISM: brassica napus

<400> SEQUENCE: 129
gtcgttgttg ttttgcgg                                              18

<210> SEQ ID NO 130
<211> LENGTH: 18
<212> TYPE: DNA
<213> ORGANISM: brassica napus

<400> SEQUENCE: 130
```

-continued

```
gaggaggagg agtcgttg                                          18

<210> SEQ ID NO 131
<211> LENGTH: 18
<212> TYPE: DNA
<213> ORGANISM: brassica napus

<400> SEQUENCE: 131
aggaggagga gtcgttgt                                          18

<210> SEQ ID NO 132
<211> LENGTH: 18
<212> TYPE: DNA
<213> ORGANISM: brassica napus

<400> SEQUENCE: 132
ggaggaggag tcgttgtt                                          18

<210> SEQ ID NO 133
<211> LENGTH: 18
<212> TYPE: DNA
<213> ORGANISM: brassica napus

<400> SEQUENCE: 133
gaggaggagt cgttgttg                                          18

<210> SEQ ID NO 134
<211> LENGTH: 18
<212> TYPE: DNA
<213> ORGANISM: brassica napus

<400> SEQUENCE: 134
aggaggagtc gttgttgt                                          18

<210> SEQ ID NO 135
<211> LENGTH: 18
<212> TYPE: DNA
<213> ORGANISM: brassica napus

<400> SEQUENCE: 135
ggaggagtcg ttgttgtt                                          18

<210> SEQ ID NO 136
<211> LENGTH: 18
<212> TYPE: DNA
<213> ORGANISM: brassica napus

<400> SEQUENCE: 136
gaggagtcgt tgttgttt                                          18

<210> SEQ ID NO 137
<211> LENGTH: 18
<212> TYPE: DNA
<213> ORGANISM: brassica napus

<400> SEQUENCE: 137
aggagtcgtt gttgtttt                                          18

<210> SEQ ID NO 138
<211> LENGTH: 13
<212> TYPE: DNA
<213> ORGANISM: brassica napus
```

-continued

```
<400> SEQUENCE: 138
caccttactt tgt                                                    13

<210> SEQ ID NO 139
<211> LENGTH: 13
<212> TYPE: DNA
<213> ORGANISM: brassica napus

<400> SEQUENCE: 139
ttgttaaatt taa                                                    13

<210> SEQ ID NO 140
<211> LENGTH: 13
<212> TYPE: DNA
<213> ORGANISM: brassica napus

<400> SEQUENCE: 140
tgttaaattt aaa                                                    13

<210> SEQ ID NO 141
<211> LENGTH: 13
<212> TYPE: DNA
<213> ORGANISM: brassica napus

<400> SEQUENCE: 141
gttaaattta aaa                                                    13

<210> SEQ ID NO 142
<211> LENGTH: 13
<212> TYPE: DNA
<213> ORGANISM: brassica napus

<400> SEQUENCE: 142
ttaaatttaa aat                                                    13

<210> SEQ ID NO 143
<211> LENGTH: 13
<212> TYPE: DNA
<213> ORGANISM: brassica napus

<400> SEQUENCE: 143
taaatttaaa ata                                                    13

<210> SEQ ID NO 144
<211> LENGTH: 13
<212> TYPE: DNA
<213> ORGANISM: brassica napus

<400> SEQUENCE: 144
aaatttaaaa tag                                                    13

<210> SEQ ID NO 145
<211> LENGTH: 13
<212> TYPE: DNA
<213> ORGANISM: brassica napus

<400> SEQUENCE: 145
aatttaaaat agt                                                    13

<210> SEQ ID NO 146
<211> LENGTH: 13
<212> TYPE: DNA
<213> ORGANISM: brassica napus
```

-continued

<400> SEQUENCE: 146
atttaaaata gtt                                                                                        13

<210> SEQ ID NO 147
<211> LENGTH: 13
<212> TYPE: DNA
<213> ORGANISM: brassica napus

<400> SEQUENCE: 147
tttaaaatag tta                                                                                        13

<210> SEQ ID NO 148
<211> LENGTH: 13
<212> TYPE: DNA
<213> ORGANISM: brassica napus

<400> SEQUENCE: 148
ttaaaatagt tac                                                                                        13

<210> SEQ ID NO 149
<211> LENGTH: 13
<212> TYPE: DNA
<213> ORGANISM: brassica napus

<400> SEQUENCE: 149
accttacttt gtt                                                                                        13

<210> SEQ ID NO 150
<211> LENGTH: 13
<212> TYPE: DNA
<213> ORGANISM: brassica napus

<400> SEQUENCE: 150
taaaatagtt aca                                                                                        13

<210> SEQ ID NO 151
<211> LENGTH: 13
<212> TYPE: DNA
<213> ORGANISM: brassica napus

<400> SEQUENCE: 151
aaaatagtta caa                                                                                        13

<210> SEQ ID NO 152
<211> LENGTH: 13
<212> TYPE: DNA
<213> ORGANISM: brassica napus

<400> SEQUENCE: 152
aaatagttac aaa                                                                                        13

<210> SEQ ID NO 153
<211> LENGTH: 13
<212> TYPE: DNA
<213> ORGANISM: brassica napus

<400> SEQUENCE: 153
ccttactttg tta                                                                                        13

<210> SEQ ID NO 154
<211> LENGTH: 13
<212> TYPE: DNA

<213> ORGANISM: brassica napus

<400> SEQUENCE: 154
cttactttgt taa                                                          13

<210> SEQ ID NO 155
<211> LENGTH: 13
<212> TYPE: DNA
<213> ORGANISM: brassica napus

<400> SEQUENCE: 155
ttactttgtt aaa                                                          13

<210> SEQ ID NO 156
<211> LENGTH: 13
<212> TYPE: DNA
<213> ORGANISM: brassica napus

<400> SEQUENCE: 156
tactttgtta aat                                                          13

<210> SEQ ID NO 157
<211> LENGTH: 13
<212> TYPE: DNA
<213> ORGANISM: brassica napus

<400> SEQUENCE: 157
actttgttaa att                                                          13

<210> SEQ ID NO 158
<211> LENGTH: 13
<212> TYPE: DNA
<213> ORGANISM: brassica napus

<400> SEQUENCE: 158
ctttgttaaa ttt                                                          13

<210> SEQ ID NO 159
<211> LENGTH: 13
<212> TYPE: DNA
<213> ORGANISM: brassica napus

<400> SEQUENCE: 159
tttgttaaat tta                                                          13

<210> SEQ ID NO 160
<211> LENGTH: 14
<212> TYPE: DNA
<213> ORGANISM: brassica napus

<400> SEQUENCE: 160
caccttactt tgtt                                                         14

<210> SEQ ID NO 161
<211> LENGTH: 14
<212> TYPE: DNA
<213> ORGANISM: brassica napus

<400> SEQUENCE: 161
ttgttaaatt taaa                                                         14

<210> SEQ ID NO 162
<211> LENGTH: 14

```
<212> TYPE: DNA
<213> ORGANISM: brassica napus

<400> SEQUENCE: 162
tgttaaattt aaaa                                                    14

<210> SEQ ID NO 163
<211> LENGTH: 14
<212> TYPE: DNA
<213> ORGANISM: brassica napus

<400> SEQUENCE: 163
gttaaattta aaat                                                    14

<210> SEQ ID NO 164
<211> LENGTH: 14
<212> TYPE: DNA
<213> ORGANISM: brassica napus

<400> SEQUENCE: 164
ttaaatttaa aata                                                    14

<210> SEQ ID NO 165
<211> LENGTH: 14
<212> TYPE: DNA
<213> ORGANISM: brassica napus

<400> SEQUENCE: 165
taaatttaaa atag                                                    14

<210> SEQ ID NO 166
<211> LENGTH: 14
<212> TYPE: DNA
<213> ORGANISM: brassica napus

<400> SEQUENCE: 166
aaatttaaaa tagt                                                    14

<210> SEQ ID NO 167
<211> LENGTH: 14
<212> TYPE: DNA
<213> ORGANISM: brassica napus

<400> SEQUENCE: 167
aatttaaaat agtt                                                    14

<210> SEQ ID NO 168
<211> LENGTH: 14
<212> TYPE: DNA
<213> ORGANISM: brassica napus

<400> SEQUENCE: 168
atttaaaata gtta                                                    14

<210> SEQ ID NO 169
<211> LENGTH: 14
<212> TYPE: DNA
<213> ORGANISM: brassica napus

<400> SEQUENCE: 169
tttaaaatag ttac                                                    14

<210> SEQ ID NO 170
```

-continued

<211> LENGTH: 14
<212> TYPE: DNA
<213> ORGANISM: brassica napus

<400> SEQUENCE: 170
ttaaaatagt taca                                                      14

<210> SEQ ID NO 171
<211> LENGTH: 14
<212> TYPE: DNA
<213> ORGANISM: brassica napus

<400> SEQUENCE: 171
accttacttt gtta                                                      14

<210> SEQ ID NO 172
<211> LENGTH: 14
<212> TYPE: DNA
<213> ORGANISM: brassica napus

<400> SEQUENCE: 172
taaaatagtt acaa                                                      14

<210> SEQ ID NO 173
<211> LENGTH: 14
<212> TYPE: DNA
<213> ORGANISM: brassica napus

<400> SEQUENCE: 173
aaaatagtta caaa                                                      14

<210> SEQ ID NO 174
<211> LENGTH: 14
<212> TYPE: DNA
<213> ORGANISM: brassica napus

<400> SEQUENCE: 174
ccttactttg ttaa                                                      14

<210> SEQ ID NO 175
<211> LENGTH: 14
<212> TYPE: DNA
<213> ORGANISM: brassica napus

<400> SEQUENCE: 175
cttactttgt taaa                                                      14

<210> SEQ ID NO 176
<211> LENGTH: 14
<212> TYPE: DNA
<213> ORGANISM: brassica napus

<400> SEQUENCE: 176
ttactttgtt aaat                                                      14

<210> SEQ ID NO 177
<211> LENGTH: 14
<212> TYPE: DNA
<213> ORGANISM: brassica napus

<400> SEQUENCE: 177
tactttgtta aatt                                                      14

-continued

```
<210> SEQ ID NO 178
<211> LENGTH: 14
<212> TYPE: DNA
<213> ORGANISM: brassica napus

<400> SEQUENCE: 178
actttgttaa attt                                                    14

<210> SEQ ID NO 179
<211> LENGTH: 14
<212> TYPE: DNA
<213> ORGANISM: brassica napus

<400> SEQUENCE: 179
ctttgttaaa ttta                                                    14

<210> SEQ ID NO 180
<211> LENGTH: 14
<212> TYPE: DNA
<213> ORGANISM: brassica napus

<400> SEQUENCE: 180
tttgttaaat ttaa                                                    14

<210> SEQ ID NO 181
<211> LENGTH: 15
<212> TYPE: DNA
<213> ORGANISM: brassica napus

<400> SEQUENCE: 181
caccttactt tgtta                                                   15

<210> SEQ ID NO 182
<211> LENGTH: 15
<212> TYPE: DNA
<213> ORGANISM: brassica napus

<400> SEQUENCE: 182
ttgttaaatt taaaa                                                   15

<210> SEQ ID NO 183
<211> LENGTH: 15
<212> TYPE: DNA
<213> ORGANISM: brassica napus

<400> SEQUENCE: 183
tgttaaattt aaaat                                                   15

<210> SEQ ID NO 184
<211> LENGTH: 15
<212> TYPE: DNA
<213> ORGANISM: brassica napus

<400> SEQUENCE: 184
gttaaattta aaata                                                   15

<210> SEQ ID NO 185
<211> LENGTH: 15
<212> TYPE: DNA
<213> ORGANISM: brassica napus

<400> SEQUENCE: 185
ttaaatttaa aatag                                                   15
```

-continued

```
<210> SEQ ID NO 186
<211> LENGTH: 15
<212> TYPE: DNA
<213> ORGANISM: brassica napus

<400> SEQUENCE: 186
taaatttaaa atagt                                                          15

<210> SEQ ID NO 187
<211> LENGTH: 15
<212> TYPE: DNA
<213> ORGANISM: brassica napus

<400> SEQUENCE: 187
aaatttaaaa tagtt                                                          15

<210> SEQ ID NO 188
<211> LENGTH: 15
<212> TYPE: DNA
<213> ORGANISM: brassica napus

<400> SEQUENCE: 188
aatttaaaat agtta                                                          15

<210> SEQ ID NO 189
<211> LENGTH: 15
<212> TYPE: DNA
<213> ORGANISM: brassica napus

<400> SEQUENCE: 189
atttaaaata gttac                                                          15

<210> SEQ ID NO 190
<211> LENGTH: 15
<212> TYPE: DNA
<213> ORGANISM: brassica napus

<400> SEQUENCE: 190
tttaaaatag ttaca                                                          15

<210> SEQ ID NO 191
<211> LENGTH: 15
<212> TYPE: DNA
<213> ORGANISM: brassica napus

<400> SEQUENCE: 191
ttaaaatagt tacaa                                                          15

<210> SEQ ID NO 192
<211> LENGTH: 15
<212> TYPE: DNA
<213> ORGANISM: brassica napus

<400> SEQUENCE: 192
accttacttt gttaa                                                          15

<210> SEQ ID NO 193
<211> LENGTH: 15
<212> TYPE: DNA
<213> ORGANISM: brassica napus

<400> SEQUENCE: 193
taaaatagtt acaaa                                                          15
```

-continued

<210> SEQ ID NO 194
<211> LENGTH: 15
<212> TYPE: DNA
<213> ORGANISM: brassica napus

<400> SEQUENCE: 194
ccttactttg ttaaa                                                              15

<210> SEQ ID NO 195
<211> LENGTH: 15
<212> TYPE: DNA
<213> ORGANISM: brassica napus

<400> SEQUENCE: 195
cttactttgt aaat                                                               15

<210> SEQ ID NO 196
<211> LENGTH: 15
<212> TYPE: DNA
<213> ORGANISM: brassica napus

<400> SEQUENCE: 196
ttactttgtt aaatt                                                              15

<210> SEQ ID NO 197
<211> LENGTH: 15
<212> TYPE: DNA
<213> ORGANISM: brassica napus

<400> SEQUENCE: 197
tactttgtta aattt                                                              15

<210> SEQ ID NO 198
<211> LENGTH: 15
<212> TYPE: DNA
<213> ORGANISM: brassica napus

<400> SEQUENCE: 198
actttgttaa attta                                                              15

<210> SEQ ID NO 199
<211> LENGTH: 15
<212> TYPE: DNA
<213> ORGANISM: brassica napus

<400> SEQUENCE: 199
ctttgttaaa tttaa                                                              15

<210> SEQ ID NO 200
<211> LENGTH: 15
<212> TYPE: DNA
<213> ORGANISM: brassica napus

<400> SEQUENCE: 200
tttgttaaat ttaaa                                                              15

<210> SEQ ID NO 201
<211> LENGTH: 16
<212> TYPE: DNA
<213> ORGANISM: brassica napus

<400> SEQUENCE: 201

-continued caccttactt tgttaa                                                    16

<210> SEQ ID NO 202
<211> LENGTH: 16
<212> TYPE: DNA
<213> ORGANISM: brassica napus

<400> SEQUENCE: 202
ttgttaaatt taaaat                                                    16

<210> SEQ ID NO 203
<211> LENGTH: 16
<212> TYPE: DNA
<213> ORGANISM: brassica napus

<400> SEQUENCE: 203
tgttaaattt aaaata                                                    16

<210> SEQ ID NO 204
<211> LENGTH: 16
<212> TYPE: DNA
<213> ORGANISM: brassica napus

<400> SEQUENCE: 204
gttaaattta aaatag                                                    16

<210> SEQ ID NO 205
<211> LENGTH: 16
<212> TYPE: DNA
<213> ORGANISM: brassica napus

<400> SEQUENCE: 205
ttaaatttaa aatagt                                                    16

<210> SEQ ID NO 206
<211> LENGTH: 16
<212> TYPE: DNA
<213> ORGANISM: brassica napus

<400> SEQUENCE: 206
taaatttaaa atagtt                                                    16

<210> SEQ ID NO 207
<211> LENGTH: 16
<212> TYPE: DNA
<213> ORGANISM: brassica napus

<400> SEQUENCE: 207
aaatttaaaa tagtta                                                    16

<210> SEQ ID NO 208
<211> LENGTH: 16
<212> TYPE: DNA
<213> ORGANISM: brassica napus

<400> SEQUENCE: 208
aatttaaaat agttac                                                    16

<210> SEQ ID NO 209
<211> LENGTH: 16
<212> TYPE: DNA
<213> ORGANISM: brassica napus

<400> SEQUENCE: 209

-continued

```
atttaaaata gttaca                                             16

<210> SEQ ID NO 210
<211> LENGTH: 16
<212> TYPE: DNA
<213> ORGANISM: brassica napus

<400> SEQUENCE: 210
tttaaaatag ttacaa                                             16

<210> SEQ ID NO 211
<211> LENGTH: 16
<212> TYPE: DNA
<213> ORGANISM: brassica napus

<400> SEQUENCE: 211
ttaaaatagt tacaaa                                             16

<210> SEQ ID NO 212
<211> LENGTH: 16
<212> TYPE: DNA
<213> ORGANISM: brassica napus

<400> SEQUENCE: 212
accttacttt gttaaa                                             16

<210> SEQ ID NO 213
<211> LENGTH: 16
<212> TYPE: DNA
<213> ORGANISM: brassica napus

<400> SEQUENCE: 213
ccttactttg ttaaat                                             16

<210> SEQ ID NO 214
<211> LENGTH: 16
<212> TYPE: DNA
<213> ORGANISM: brassica napus

<400> SEQUENCE: 214
cttactttgt taaatt                                             16

<210> SEQ ID NO 215
<211> LENGTH: 16
<212> TYPE: DNA
<213> ORGANISM: brassica napus

<400> SEQUENCE: 215
ttactttgtt aaattt                                             16

<210> SEQ ID NO 216
<211> LENGTH: 16
<212> TYPE: DNA
<213> ORGANISM: brassica napus

<400> SEQUENCE: 216
tactttgtta aattta                                             16

<210> SEQ ID NO 217
<211> LENGTH: 16
<212> TYPE: DNA
<213> ORGANISM: brassica napus
```

-continued

```
<400> SEQUENCE: 217
actttgttaa atttaa                                              16

<210> SEQ ID NO 218
<211> LENGTH: 16
<212> TYPE: DNA
<213> ORGANISM: brassica napus

<400> SEQUENCE: 218
ctttgttaaa tttaaa                                              16

<210> SEQ ID NO 219
<211> LENGTH: 16
<212> TYPE: DNA
<213> ORGANISM: brassica napus

<400> SEQUENCE: 219
tttgttaaat ttaaaa                                              16

<210> SEQ ID NO 220
<211> LENGTH: 17
<212> TYPE: DNA
<213> ORGANISM: brassica napus

<400> SEQUENCE: 220
caccttactt tgttaaa                                             17

<210> SEQ ID NO 221
<211> LENGTH: 17
<212> TYPE: DNA
<213> ORGANISM: brassica napus

<400> SEQUENCE: 221
ttgttaaatt taaaata                                             17

<210> SEQ ID NO 222
<211> LENGTH: 17
<212> TYPE: DNA
<213> ORGANISM: brassica napus

<400> SEQUENCE: 222
tgttaaattt aaaatag                                             17

<210> SEQ ID NO 223
<211> LENGTH: 17
<212> TYPE: DNA
<213> ORGANISM: brassica napus

<400> SEQUENCE: 223
gttaaattta aaatagt                                             17

<210> SEQ ID NO 224
<211> LENGTH: 17
<212> TYPE: DNA
<213> ORGANISM: brassica napus

<400> SEQUENCE: 224
ttaaatttaa aatagtt                                             17

<210> SEQ ID NO 225
<211> LENGTH: 17
<212> TYPE: DNA
<213> ORGANISM: brassica napus
```

-continued

```
<400> SEQUENCE: 225
taaatttaaa atagtta                                                    17

<210> SEQ ID NO 226
<211> LENGTH: 17
<212> TYPE: DNA
<213> ORGANISM: brassica napus

<400> SEQUENCE: 226
aaatttaaaa tagttac                                                    17

<210> SEQ ID NO 227
<211> LENGTH: 17
<212> TYPE: DNA
<213> ORGANISM: brassica napus

<400> SEQUENCE: 227
aatttaaaat agttaca                                                    17

<210> SEQ ID NO 228
<211> LENGTH: 17
<212> TYPE: DNA
<213> ORGANISM: brassica napus

<400> SEQUENCE: 228
atttaaaata gttacaa                                                    17

<210> SEQ ID NO 229
<211> LENGTH: 17
<212> TYPE: DNA
<213> ORGANISM: brassica napus

<400> SEQUENCE: 229
tttaaaatag ttacaaa                                                    17

<210> SEQ ID NO 230
<211> LENGTH: 17
<212> TYPE: DNA
<213> ORGANISM: brassica napus

<400> SEQUENCE: 230
accttacttt gttaaat                                                    17

<210> SEQ ID NO 231
<211> LENGTH: 17
<212> TYPE: DNA
<213> ORGANISM: brassica napus

<400> SEQUENCE: 231
ccttactttg ttaaatt                                                    17

<210> SEQ ID NO 232
<211> LENGTH: 17
<212> TYPE: DNA
<213> ORGANISM: brassica napus

<400> SEQUENCE: 232
cttactttgt taaattt                                                    17

<210> SEQ ID NO 233
<211> LENGTH: 17
<212> TYPE: DNA
```

-continued

```
<213> ORGANISM: brassica napus

<400> SEQUENCE: 233
ttactttgtt aaattta                                              17

<210> SEQ ID NO 234
<211> LENGTH: 17
<212> TYPE: DNA
<213> ORGANISM: brassica napus

<400> SEQUENCE: 234
tactttgtta aatttaa                                              17

<210> SEQ ID NO 235
<211> LENGTH: 17
<212> TYPE: DNA
<213> ORGANISM: brassica napus

<400> SEQUENCE: 235
actttgttaa atttaaa                                              17

<210> SEQ ID NO 236
<211> LENGTH: 17
<212> TYPE: DNA
<213> ORGANISM: brassica napus

<400> SEQUENCE: 236
ctttgttaaa tttaaaa                                              17

<210> SEQ ID NO 237
<211> LENGTH: 17
<212> TYPE: DNA
<213> ORGANISM: brassica napus

<400> SEQUENCE: 237
tttgttaaat ttaaaat                                              17

<210> SEQ ID NO 238
<211> LENGTH: 18
<212> TYPE: DNA
<213> ORGANISM: brassica napus

<400> SEQUENCE: 238
caccttactt tgttaaat                                             18

<210> SEQ ID NO 239
<211> LENGTH: 18
<212> TYPE: DNA
<213> ORGANISM: brassica napus

<400> SEQUENCE: 239
ttgttaaatt taaaatag                                             18

<210> SEQ ID NO 240
<211> LENGTH: 18
<212> TYPE: DNA
<213> ORGANISM: brassica napus

<400> SEQUENCE: 240
tgttaaattt aaaatagt                                             18

<210> SEQ ID NO 241
<211> LENGTH: 18
```

```
<212> TYPE: DNA
<213> ORGANISM: brassica napus

<400> SEQUENCE: 241
gttaaattta aaatagtt                                              18

<210> SEQ ID NO 242
<211> LENGTH: 18
<212> TYPE: DNA
<213> ORGANISM: brassica napus

<400> SEQUENCE: 242
taaatttaaa atagttac                                              18

<210> SEQ ID NO 243
<211> LENGTH: 18
<212> TYPE: DNA
<213> ORGANISM: brassica napus

<400> SEQUENCE: 243
aaatttaaaa tagttaca                                              18

<210> SEQ ID NO 244
<211> LENGTH: 18
<212> TYPE: DNA
<213> ORGANISM: brassica napus

<400> SEQUENCE: 244
aatttaaaat agttacaa                                              18

<210> SEQ ID NO 245
<211> LENGTH: 18
<212> TYPE: DNA
<213> ORGANISM: brassica napus

<400> SEQUENCE: 245
atttaaaata gttacaaa                                              18

<210> SEQ ID NO 246
<211> LENGTH: 18
<212> TYPE: DNA
<213> ORGANISM: brassica napus

<400> SEQUENCE: 246
ttaaatttaa aatagtta                                              18

<210> SEQ ID NO 247
<211> LENGTH: 18
<212> TYPE: DNA
<213> ORGANISM: brassica napus

<400> SEQUENCE: 247
accttacttt gttaaatt                                              18

<210> SEQ ID NO 248
<211> LENGTH: 18
<212> TYPE: DNA
<213> ORGANISM: brassica napus

<400> SEQUENCE: 248
ccttactttg ttaaattt                                              18

<210> SEQ ID NO 249
```

-continued

```
<211> LENGTH: 18
<212> TYPE: DNA
<213> ORGANISM: brassica napus

<400> SEQUENCE: 249
cttactttgt taaattta                                                  18

<210> SEQ ID NO 250
<211> LENGTH: 18
<212> TYPE: DNA
<213> ORGANISM: brassica napus

<400> SEQUENCE: 250
ttactttgtt aaatttaa                                                  18

<210> SEQ ID NO 251
<211> LENGTH: 18
<212> TYPE: DNA
<213> ORGANISM: brassica napus

<400> SEQUENCE: 251
tactttgtta aatttaaa                                                  18

<210> SEQ ID NO 252
<211> LENGTH: 18
<212> TYPE: DNA
<213> ORGANISM: brassica napus

<400> SEQUENCE: 252
actttgttaa atttaaaa                                                  18

<210> SEQ ID NO 253
<211> LENGTH: 18
<212> TYPE: DNA
<213> ORGANISM: brassica napus

<400> SEQUENCE: 253
ctttgttaaa tttaaaat                                                  18

<210> SEQ ID NO 254
<211> LENGTH: 18
<212> TYPE: DNA
<213> ORGANISM: brassica napus

<400> SEQUENCE: 254
tttgttaaat ttaaaata                                                  18

<210> SEQ ID NO 255
<211> LENGTH: 13
<212> TYPE: DNA
<213> ORGANISM: brassica napus

<400> SEQUENCE: 255
gcaaagcaac gat                                                       13

<210> SEQ ID NO 256
<211> LENGTH: 13
<212> TYPE: DNA
<213> ORGANISM: brassica napus

<400> SEQUENCE: 256
cgattccgac gac                                                       13
```

-continued

```
<210> SEQ ID NO 257
<211> LENGTH: 13
<212> TYPE: DNA
<213> ORGANISM: brassica napus

<400> SEQUENCE: 257
gattccgacg act                                                        13

<210> SEQ ID NO 258
<211> LENGTH: 13
<212> TYPE: DNA
<213> ORGANISM: brassica napus

<400> SEQUENCE: 258
attccgacga ctc                                                        13

<210> SEQ ID NO 259
<211> LENGTH: 13
<212> TYPE: DNA
<213> ORGANISM: brassica napus

<400> SEQUENCE: 259
ttccgacgac tcc                                                        13

<210> SEQ ID NO 260
<211> LENGTH: 13
<212> TYPE: DNA
<213> ORGANISM: brassica napus

<400> SEQUENCE: 260
tccgacgact cct                                                        13

<210> SEQ ID NO 261
<211> LENGTH: 13
<212> TYPE: DNA
<213> ORGANISM: brassica napus

<400> SEQUENCE: 261
ccgacgactc ctc                                                        13

<210> SEQ ID NO 262
<211> LENGTH: 13
<212> TYPE: DNA
<213> ORGANISM: brassica napus

<400> SEQUENCE: 262
cgacgactcc tcc                                                        13

<210> SEQ ID NO 263
<211> LENGTH: 13
<212> TYPE: DNA
<213> ORGANISM: brassica napus

<400> SEQUENCE: 263
gacgactcct cct                                                        13

<210> SEQ ID NO 264
<211> LENGTH: 13
<212> TYPE: DNA
<213> ORGANISM: brassica napus

<400> SEQUENCE: 264
acgactcctc ctc                                                        13
```

-continued

```
<210> SEQ ID NO 265
<211> LENGTH: 13
<212> TYPE: DNA
<213> ORGANISM: brassica napus

<400> SEQUENCE: 265
cgactcctcc tcc                                                        13

<210> SEQ ID NO 266
<211> LENGTH: 13
<212> TYPE: DNA
<213> ORGANISM: brassica napus

<400> SEQUENCE: 266
caaagcaacg att                                                        13

<210> SEQ ID NO 267
<211> LENGTH: 13
<212> TYPE: DNA
<213> ORGANISM: brassica napus

<400> SEQUENCE: 267
gactcctcct ccg                                                        13

<210> SEQ ID NO 268
<211> LENGTH: 13
<212> TYPE: DNA
<213> ORGANISM: brassica napus

<400> SEQUENCE: 268
actcctcctc cgc                                                        13

<210> SEQ ID NO 269
<211> LENGTH: 13
<212> TYPE: DNA
<213> ORGANISM: brassica napus

<400> SEQUENCE: 269
ctcctcctcc gcc                                                        13

<210> SEQ ID NO 270
<211> LENGTH: 13
<212> TYPE: DNA
<213> ORGANISM: brassica napus

<400> SEQUENCE: 270
aaagcaacga ttc                                                        13

<210> SEQ ID NO 271
<211> LENGTH: 13
<212> TYPE: DNA
<213> ORGANISM: brassica napus

<400> SEQUENCE: 271
aagcaacgat tcc                                                        13

<210> SEQ ID NO 272
<211> LENGTH: 13
<212> TYPE: DNA
<213> ORGANISM: brassica napus

<400> SEQUENCE: 272
agcaacgatt ccg                                                        13
```

-continued

```
<210> SEQ ID NO 273
<211> LENGTH: 13
<212> TYPE: DNA
<213> ORGANISM: brassica napus

<400> SEQUENCE: 273
gcaacgattc cga                                                      13

<210> SEQ ID NO 274
<211> LENGTH: 13
<212> TYPE: DNA
<213> ORGANISM: brassica napus

<400> SEQUENCE: 274
caacgattcc gac                                                      13

<210> SEQ ID NO 275
<211> LENGTH: 13
<212> TYPE: DNA
<213> ORGANISM: brassica napus

<400> SEQUENCE: 275
aacgattccg acg                                                      13

<210> SEQ ID NO 276
<211> LENGTH: 13
<212> TYPE: DNA
<213> ORGANISM: brassica napus

<400> SEQUENCE: 276
acgattccga cga                                                      13

<210> SEQ ID NO 277
<211> LENGTH: 14
<212> TYPE: DNA
<213> ORGANISM: brassica napus

<400> SEQUENCE: 277
gcaaagcaac gatt                                                     14

<210> SEQ ID NO 278
<211> LENGTH: 14
<212> TYPE: DNA
<213> ORGANISM: brassica napus

<400> SEQUENCE: 278
cgattccgac gact                                                     14

<210> SEQ ID NO 279
<211> LENGTH: 14
<212> TYPE: DNA
<213> ORGANISM: brassica napus

<400> SEQUENCE: 279
gattccgacg actc                                                     14

<210> SEQ ID NO 280
<211> LENGTH: 14
<212> TYPE: DNA
<213> ORGANISM: brassica napus

<400> SEQUENCE: 280
```

-continued

```
attccgacga ctcc                                                    14

<210> SEQ ID NO 281
<211> LENGTH: 14
<212> TYPE: DNA
<213> ORGANISM: brassica napus

<400> SEQUENCE: 281
ttccgacgac tcct                                                    14

<210> SEQ ID NO 282
<211> LENGTH: 14
<212> TYPE: DNA
<213> ORGANISM: brassica napus

<400> SEQUENCE: 282
tccgacgact cctc                                                    14

<210> SEQ ID NO 283
<211> LENGTH: 14
<212> TYPE: DNA
<213> ORGANISM: brassica napus

<400> SEQUENCE: 283
ccgacgactc ctcc                                                    14

<210> SEQ ID NO 284
<211> LENGTH: 14
<212> TYPE: DNA
<213> ORGANISM: brassica napus

<400> SEQUENCE: 284
cgacgactcc tcct                                                    14

<210> SEQ ID NO 285
<211> LENGTH: 14
<212> TYPE: DNA
<213> ORGANISM: brassica napus

<400> SEQUENCE: 285
gacgactcct cctc                                                    14

<210> SEQ ID NO 286
<211> LENGTH: 14
<212> TYPE: DNA
<213> ORGANISM: brassica napus

<400> SEQUENCE: 286
acgactcctc ctcc                                                    14

<210> SEQ ID NO 287
<211> LENGTH: 14
<212> TYPE: DNA
<213> ORGANISM: brassica napus

<400> SEQUENCE: 287
cgactcctcc tccg                                                    14

<210> SEQ ID NO 288
<211> LENGTH: 14
<212> TYPE: DNA
<213> ORGANISM: brassica napus

<400> SEQUENCE: 288
```

-continued

```
caaagcaacg attc                                          14

<210> SEQ ID NO 289
<211> LENGTH: 14
<212> TYPE: DNA
<213> ORGANISM: brassica napus

<400> SEQUENCE: 289
gactcctcct ccgc                                          14

<210> SEQ ID NO 290
<211> LENGTH: 14
<212> TYPE: DNA
<213> ORGANISM: brassica napus

<400> SEQUENCE: 290
actcctcctc cgcc                                          14

<210> SEQ ID NO 291
<211> LENGTH: 14
<212> TYPE: DNA
<213> ORGANISM: brassica napus

<400> SEQUENCE: 291
aaagcaacga ttcc                                          14

<210> SEQ ID NO 292
<211> LENGTH: 14
<212> TYPE: DNA
<213> ORGANISM: brassica napus

<400> SEQUENCE: 292
aagcaacgat tccg                                          14

<210> SEQ ID NO 293
<211> LENGTH: 14
<212> TYPE: DNA
<213> ORGANISM: brassica napus

<400> SEQUENCE: 293
agcaacgatt ccga                                          14

<210> SEQ ID NO 294
<211> LENGTH: 14
<212> TYPE: DNA
<213> ORGANISM: brassica napus

<400> SEQUENCE: 294
gcaacgattc cgac                                          14

<210> SEQ ID NO 295
<211> LENGTH: 14
<212> TYPE: DNA
<213> ORGANISM: brassica napus

<400> SEQUENCE: 295
caacgattcc gacg                                          14

<210> SEQ ID NO 296
<211> LENGTH: 14
<212> TYPE: DNA
<213> ORGANISM: brassica napus
```

-continued

```
<400> SEQUENCE: 296
aacgattccg acga                                                    14

<210> SEQ ID NO 297
<211> LENGTH: 14
<212> TYPE: DNA
<213> ORGANISM: brassica napus

<400> SEQUENCE: 297
acgattccga cgac                                                    14

<210> SEQ ID NO 298
<211> LENGTH: 15
<212> TYPE: DNA
<213> ORGANISM: brassica napus

<400> SEQUENCE: 298
gcaaagcaac gattc                                                   15

<210> SEQ ID NO 299
<211> LENGTH: 15
<212> TYPE: DNA
<213> ORGANISM: brassica napus

<400> SEQUENCE: 299
cgattccgac gactc                                                   15

<210> SEQ ID NO 300
<211> LENGTH: 15
<212> TYPE: DNA
<213> ORGANISM: brassica napus

<400> SEQUENCE: 300
gattccgacg actcc                                                   15

<210> SEQ ID NO 301
<211> LENGTH: 15
<212> TYPE: DNA
<213> ORGANISM: brassica napus

<400> SEQUENCE: 301
attccgacga ctcct                                                   15

<210> SEQ ID NO 302
<211> LENGTH: 15
<212> TYPE: DNA
<213> ORGANISM: brassica napus

<400> SEQUENCE: 302
ttccgacgac tcctc                                                   15

<210> SEQ ID NO 303
<211> LENGTH: 15
<212> TYPE: DNA
<213> ORGANISM: brassica napus

<400> SEQUENCE: 303
tccgacgact cctcc                                                   15

<210> SEQ ID NO 304
<211> LENGTH: 15
<212> TYPE: DNA
<213> ORGANISM: brassica napus
```

-continued

```
<400> SEQUENCE: 304
ccgacgactc ctcct                                              15

<210> SEQ ID NO 305
<211> LENGTH: 15
<212> TYPE: DNA
<213> ORGANISM: brassica napus

<400> SEQUENCE: 305
cgacgactcc tcctc                                             15

<210> SEQ ID NO 306
<211> LENGTH: 15
<212> TYPE: DNA
<213> ORGANISM: brassica napus

<400> SEQUENCE: 306
gacgactcct cctcc                                             15

<210> SEQ ID NO 307
<211> LENGTH: 15
<212> TYPE: DNA
<213> ORGANISM: brassica napus

<400> SEQUENCE: 307
acgactcctc ctccg                                             15

<210> SEQ ID NO 308
<211> LENGTH: 15
<212> TYPE: DNA
<213> ORGANISM: brassica napus

<400> SEQUENCE: 308
cgactcctcc tccgc                                             15

<210> SEQ ID NO 309
<211> LENGTH: 15
<212> TYPE: DNA
<213> ORGANISM: brassica napus

<400> SEQUENCE: 309
caaagcaacg attcc                                             15

<210> SEQ ID NO 310
<211> LENGTH: 15
<212> TYPE: DNA
<213> ORGANISM: brassica napus

<400> SEQUENCE: 310
gactcctcct ccgcc                                             15

<210> SEQ ID NO 311
<211> LENGTH: 15
<212> TYPE: DNA
<213> ORGANISM: brassica napus

<400> SEQUENCE: 311
aaagcaacga ttccg                                             15

<210> SEQ ID NO 312
<211> LENGTH: 15
<212> TYPE: DNA
```

-continued

```
<213> ORGANISM: brassica napus

<400> SEQUENCE: 312
aagcaacgat tccga                                                    15

<210> SEQ ID NO 313
<211> LENGTH: 15
<212> TYPE: DNA
<213> ORGANISM: brassica napus

<400> SEQUENCE: 313
agcaacgatt ccgac                                                    15

<210> SEQ ID NO 314
<211> LENGTH: 15
<212> TYPE: DNA
<213> ORGANISM: brassica napus

<400> SEQUENCE: 314
gcaacgattc cgacg                                                    15

<210> SEQ ID NO 315
<211> LENGTH: 15
<212> TYPE: DNA
<213> ORGANISM: brassica napus

<400> SEQUENCE: 315
caacgattcc gacga                                                    15

<210> SEQ ID NO 316
<211> LENGTH: 15
<212> TYPE: DNA
<213> ORGANISM: brassica napus

<400> SEQUENCE: 316
aacgattccg acgac                                                    15

<210> SEQ ID NO 317
<211> LENGTH: 15
<212> TYPE: DNA
<213> ORGANISM: brassica napus

<400> SEQUENCE: 317
acgattccga cgact                                                    15

<210> SEQ ID NO 318
<211> LENGTH: 16
<212> TYPE: DNA
<213> ORGANISM: brassica napus

<400> SEQUENCE: 318
gcaaagcaac gattcc                                                   16

<210> SEQ ID NO 319
<211> LENGTH: 16
<212> TYPE: DNA
<213> ORGANISM: brassica napus

<400> SEQUENCE: 319
cgattccgac gactcc                                                   16

<210> SEQ ID NO 320
<211> LENGTH: 16
```

-continued

```
<212> TYPE: DNA
<213> ORGANISM: brassica napus

<400> SEQUENCE: 320
gattccgacg actcct                                                    16

<210> SEQ ID NO 321
<211> LENGTH: 16
<212> TYPE: DNA
<213> ORGANISM: brassica napus

<400> SEQUENCE: 321
attccgacga ctcctc                                                    16

<210> SEQ ID NO 322
<211> LENGTH: 16
<212> TYPE: DNA
<213> ORGANISM: brassica napus

<400> SEQUENCE: 322
ttccgacgac tcctcc                                                    16

<210> SEQ ID NO 323
<211> LENGTH: 16
<212> TYPE: DNA
<213> ORGANISM: brassica napus

<400> SEQUENCE: 323
tccgacgact cctcct                                                    16

<210> SEQ ID NO 324
<211> LENGTH: 16
<212> TYPE: DNA
<213> ORGANISM: brassica napus

<400> SEQUENCE: 324
ccgacgactc ctcctc                                                    16

<210> SEQ ID NO 325
<211> LENGTH: 16
<212> TYPE: DNA
<213> ORGANISM: brassica napus

<400> SEQUENCE: 325
cgacgactcc tcctcc                                                    16

<210> SEQ ID NO 326
<211> LENGTH: 16
<212> TYPE: DNA
<213> ORGANISM: brassica napus

<400> SEQUENCE: 326
gacgactcct cctccg                                                    16

<210> SEQ ID NO 327
<211> LENGTH: 16
<212> TYPE: DNA
<213> ORGANISM: brassica napus

<400> SEQUENCE: 327
acgactcctc ctccgc                                                    16

<210> SEQ ID NO 328
```

-continued

```
<211> LENGTH: 16
<212> TYPE: DNA
<213> ORGANISM: brassica napus

<400> SEQUENCE: 328
cgactcctcc tccgcc                                                    16

<210> SEQ ID NO 329
<211> LENGTH: 16
<212> TYPE: DNA
<213> ORGANISM: brassica napus

<400> SEQUENCE: 329
caaagcaacg attccg                                                    16

<210> SEQ ID NO 330
<211> LENGTH: 16
<212> TYPE: DNA
<213> ORGANISM: brassica napus

<400> SEQUENCE: 330
aaagcaacga ttccga                                                    16

<210> SEQ ID NO 331
<211> LENGTH: 16
<212> TYPE: DNA
<213> ORGANISM: brassica napus

<400> SEQUENCE: 331
aagcaacgat tccgac                                                    16

<210> SEQ ID NO 332
<211> LENGTH: 16
<212> TYPE: DNA
<213> ORGANISM: brassica napus

<400> SEQUENCE: 332
agcaacgatt ccgacg                                                    16

<210> SEQ ID NO 333
<211> LENGTH: 16
<212> TYPE: DNA
<213> ORGANISM: brassica napus

<400> SEQUENCE: 333
gcaacgattc cgacga                                                    16

<210> SEQ ID NO 334
<211> LENGTH: 16
<212> TYPE: DNA
<213> ORGANISM: brassica napus

<400> SEQUENCE: 334
caacgattcc gacgac                                                    16

<210> SEQ ID NO 335
<211> LENGTH: 16
<212> TYPE: DNA
<213> ORGANISM: brassica napus

<400> SEQUENCE: 335
aacgattccg acgact                                                    16
```

```
<210> SEQ ID NO 336
<211> LENGTH: 16
<212> TYPE: DNA
<213> ORGANISM: brassica napus

<400> SEQUENCE: 336
acgattccga cgactc                                             16

<210> SEQ ID NO 337
<211> LENGTH: 17
<212> TYPE: DNA
<213> ORGANISM: brassica napus

<400> SEQUENCE: 337
gcaaagcaac gattccg                                            17

<210> SEQ ID NO 338
<211> LENGTH: 17
<212> TYPE: DNA
<213> ORGANISM: brassica napus

<400> SEQUENCE: 338
cgattccgac gactcct                                            17

<210> SEQ ID NO 339
<211> LENGTH: 17
<212> TYPE: DNA
<213> ORGANISM: brassica napus

<400> SEQUENCE: 339
gattccgacg actcctc                                            17

<210> SEQ ID NO 340
<211> LENGTH: 17
<212> TYPE: DNA
<213> ORGANISM: brassica napus

<400> SEQUENCE: 340
attccgacga ctcctcc                                            17

<210> SEQ ID NO 341
<211> LENGTH: 17
<212> TYPE: DNA
<213> ORGANISM: brassica napus

<400> SEQUENCE: 341
ttccgacgac tcctcct                                            17

<210> SEQ ID NO 342
<211> LENGTH: 17
<212> TYPE: DNA
<213> ORGANISM: brassica napus

<400> SEQUENCE: 342
tccgacgact cctcctc                                            17

<210> SEQ ID NO 343
<211> LENGTH: 17
<212> TYPE: DNA
<213> ORGANISM: brassica napus

<400> SEQUENCE: 343
ccgacgactc ctcctcc                                            17
```

-continued

<210> SEQ ID NO 344
<211> LENGTH: 17
<212> TYPE: DNA
<213> ORGANISM: brassica napus

<400> SEQUENCE: 344
cgacgactcc tcctccg                                                    17

<210> SEQ ID NO 345
<211> LENGTH: 17
<212> TYPE: DNA
<213> ORGANISM: brassica napus

<400> SEQUENCE: 345
gacgactcct cctccgc                                                    17

<210> SEQ ID NO 346
<211> LENGTH: 17
<212> TYPE: DNA
<213> ORGANISM: brassica napus

<400> SEQUENCE: 346
acgactcctc ctccgcc                                                    17

<210> SEQ ID NO 347
<211> LENGTH: 17
<212> TYPE: DNA
<213> ORGANISM: brassica napus

<400> SEQUENCE: 347
caaagcaacg attccga                                                    17

<210> SEQ ID NO 348
<211> LENGTH: 17
<212> TYPE: DNA
<213> ORGANISM: brassica napus

<400> SEQUENCE: 348
aaagcaacga ttccgac                                                    17

<210> SEQ ID NO 349
<211> LENGTH: 17
<212> TYPE: DNA
<213> ORGANISM: brassica napus

<400> SEQUENCE: 349
aagcaacgat tccgacg                                                    17

<210> SEQ ID NO 350
<211> LENGTH: 17
<212> TYPE: DNA
<213> ORGANISM: brassica napus

<400> SEQUENCE: 350
agcaacgatt ccgacga                                                    17

<210> SEQ ID NO 351
<211> LENGTH: 17
<212> TYPE: DNA
<213> ORGANISM: brassica napus

<400> SEQUENCE: 351
gcaacgattc cgacgac                                                    17

-continued

<210> SEQ ID NO 352
<211> LENGTH: 17
<212> TYPE: DNA
<213> ORGANISM: brassica napus

<400> SEQUENCE: 352
caacgattcc gacgact                                              17

<210> SEQ ID NO 353
<211> LENGTH: 17
<212> TYPE: DNA
<213> ORGANISM: brassica napus

<400> SEQUENCE: 353
aacgattccg acgactc                                              17

<210> SEQ ID NO 354
<211> LENGTH: 17
<212> TYPE: DNA
<213> ORGANISM: brassica napus

<400> SEQUENCE: 354
acgattccga cgactcc                                              17

<210> SEQ ID NO 355
<211> LENGTH: 18
<212> TYPE: DNA
<213> ORGANISM: brassica napus

<400> SEQUENCE: 355
gcaaagcaac gattccga                                             18

<210> SEQ ID NO 356
<211> LENGTH: 18
<212> TYPE: DNA
<213> ORGANISM: brassica napus

<400> SEQUENCE: 356
cgattccgac gactcctc                                             18

<210> SEQ ID NO 357
<211> LENGTH: 18
<212> TYPE: DNA
<213> ORGANISM: brassica napus

<400> SEQUENCE: 357
gattccgacg actcctcc                                             18

<210> SEQ ID NO 358
<211> LENGTH: 18
<212> TYPE: DNA
<213> ORGANISM: brassica napus

<400> SEQUENCE: 358
attccgacga ctcctcct                                             18

<210> SEQ ID NO 359
<211> LENGTH: 18
<212> TYPE: DNA
<213> ORGANISM: brassica napus

<400> SEQUENCE: 359

-continued

```
tccgacgact cctcctcc                                            18

<210> SEQ ID NO 360
<211> LENGTH: 18
<212> TYPE: DNA
<213> ORGANISM: brassica napus

<400> SEQUENCE: 360
ccgacgactc ctcctccg                                            18

<210> SEQ ID NO 361
<211> LENGTH: 18
<212> TYPE: DNA
<213> ORGANISM: brassica napus

<400> SEQUENCE: 361
cgacgactcc tcctccgc                                            18

<210> SEQ ID NO 362
<211> LENGTH: 18
<212> TYPE: DNA
<213> ORGANISM: brassica napus

<400> SEQUENCE: 362
gacgactcct cctccgcc                                            18

<210> SEQ ID NO 363
<211> LENGTH: 18
<212> TYPE: DNA
<213> ORGANISM: brassica napus

<400> SEQUENCE: 363
ttccgacgac tcctcctc                                            18

<210> SEQ ID NO 364
<211> LENGTH: 18
<212> TYPE: DNA
<213> ORGANISM: brassica napus

<400> SEQUENCE: 364
caaagcaacg attccgac                                            18

<210> SEQ ID NO 365
<211> LENGTH: 18
<212> TYPE: DNA
<213> ORGANISM: brassica napus

<400> SEQUENCE: 365
aaagcaacga ttccgacg                                            18

<210> SEQ ID NO 366
<211> LENGTH: 18
<212> TYPE: DNA
<213> ORGANISM: brassica napus

<400> SEQUENCE: 366
aagcaacgat tccgacga                                            18

<210> SEQ ID NO 367
<211> LENGTH: 18
<212> TYPE: DNA
<213> ORGANISM: brassica napus

<400> SEQUENCE: 367
```

-continued

```
agcaacgatt ccgacgac                                              18

<210> SEQ ID NO 368
<211> LENGTH: 18
<212> TYPE: DNA
<213> ORGANISM: brassica napus

<400> SEQUENCE: 368
gcaacgattc cgacgact                                              18

<210> SEQ ID NO 369
<211> LENGTH: 18
<212> TYPE: DNA
<213> ORGANISM: brassica napus

<400> SEQUENCE: 369
caacgattcc gacgactc                                              18

<210> SEQ ID NO 370
<211> LENGTH: 18
<212> TYPE: DNA
<213> ORGANISM: brassica napus

<400> SEQUENCE: 370
aacgattccg acgactcc                                              18

<210> SEQ ID NO 371
<211> LENGTH: 18
<212> TYPE: DNA
<213> ORGANISM: brassica napus

<400> SEQUENCE: 371
acgattccga cgactcct                                              18

<210> SEQ ID NO 372
<211> LENGTH: 13
<212> TYPE: DNA
<213> ORGANISM: brassica napus

<400> SEQUENCE: 372
acaccctact ttg                                                   13

<210> SEQ ID NO 373
<211> LENGTH: 13
<212> TYPE: DNA
<213> ORGANISM: brassica napus

<400> SEQUENCE: 373
tttgtgaaaa gtc                                                   13

<210> SEQ ID NO 374
<211> LENGTH: 13
<212> TYPE: DNA
<213> ORGANISM: brassica napus

<400> SEQUENCE: 374
ttgtgaaaag tcg                                                   13

<210> SEQ ID NO 375
<211> LENGTH: 13
<212> TYPE: DNA
<213> ORGANISM: brassica napus
```

-continued

```
<400> SEQUENCE: 375
tgtgaaaagt cgc                                              13

<210> SEQ ID NO 376
<211> LENGTH: 13
<212> TYPE: DNA
<213> ORGANISM: brassica napus

<400> SEQUENCE: 376
gtgaaaagtc gct                                              13

<210> SEQ ID NO 377
<211> LENGTH: 13
<212> TYPE: DNA
<213> ORGANISM: brassica napus

<400> SEQUENCE: 377
tgaaaagtcg ctg                                              13

<210> SEQ ID NO 378
<211> LENGTH: 13
<212> TYPE: DNA
<213> ORGANISM: brassica napus

<400> SEQUENCE: 378
gaaaagtcgc tga                                              13

<210> SEQ ID NO 379
<211> LENGTH: 13
<212> TYPE: DNA
<213> ORGANISM: brassica napus

<400> SEQUENCE: 379
aaaagtcgct gat                                              13

<210> SEQ ID NO 380
<211> LENGTH: 13
<212> TYPE: DNA
<213> ORGANISM: brassica napus

<400> SEQUENCE: 380
aaagtcgctg atc                                              13

<210> SEQ ID NO 381
<211> LENGTH: 13
<212> TYPE: DNA
<213> ORGANISM: brassica napus

<400> SEQUENCE: 381
aagtcgctga tct                                              13

<210> SEQ ID NO 382
<211> LENGTH: 13
<212> TYPE: DNA
<213> ORGANISM: brassica napus

<400> SEQUENCE: 382
agtcgctgat ctt                                              13

<210> SEQ ID NO 383
<211> LENGTH: 13
<212> TYPE: DNA
<213> ORGANISM: brassica napus
```

-continued

```
<400> SEQUENCE: 383
caccctactt tgt                                                    13

<210> SEQ ID NO 384
<211> LENGTH: 13
<212> TYPE: DNA
<213> ORGANISM: brassica napus

<400> SEQUENCE: 384
gtcgctgatc tta                                                    13

<210> SEQ ID NO 385
<211> LENGTH: 13
<212> TYPE: DNA
<213> ORGANISM: brassica napus

<400> SEQUENCE: 385
tcgctgatct tat                                                    13

<210> SEQ ID NO 386
<211> LENGTH: 13
<212> TYPE: DNA
<213> ORGANISM: brassica napus

<400> SEQUENCE: 386
cgctgatctt att                                                    13

<210> SEQ ID NO 387
<211> LENGTH: 13
<212> TYPE: DNA
<213> ORGANISM: brassica napus

<400> SEQUENCE: 387
accctacttt gtg                                                    13

<210> SEQ ID NO 388
<211> LENGTH: 13
<212> TYPE: DNA
<213> ORGANISM: brassica napus

<400> SEQUENCE: 388
ccctactttg tga                                                    13

<210> SEQ ID NO 389
<211> LENGTH: 13
<212> TYPE: DNA
<213> ORGANISM: brassica napus

<400> SEQUENCE: 389
cctactttgt gaa                                                    13

<210> SEQ ID NO 390
<211> LENGTH: 13
<212> TYPE: DNA
<213> ORGANISM: brassica napus

<400> SEQUENCE: 390
ctactttgtg aaa                                                    13

<210> SEQ ID NO 391
<211> LENGTH: 13
<212> TYPE: DNA
```

-continued

```
<213> ORGANISM: brassica napus

<400> SEQUENCE: 391
tactttgtga aaa                                                          13

<210> SEQ ID NO 392
<211> LENGTH: 13
<212> TYPE: DNA
<213> ORGANISM: brassica napus

<400> SEQUENCE: 392
actttgtgaa aag                                                          13

<210> SEQ ID NO 393
<211> LENGTH: 13
<212> TYPE: DNA
<213> ORGANISM: brassica napus

<400> SEQUENCE: 393
ctttgtgaaa agt                                                          13

<210> SEQ ID NO 394
<211> LENGTH: 14
<212> TYPE: DNA
<213> ORGANISM: brassica napus

<400> SEQUENCE: 394
acaccctact ttgt                                                         14

<210> SEQ ID NO 395
<211> LENGTH: 14
<212> TYPE: DNA
<213> ORGANISM: brassica napus

<400> SEQUENCE: 395
tttgtgaaaa gtcg                                                         14

<210> SEQ ID NO 396
<211> LENGTH: 14
<212> TYPE: DNA
<213> ORGANISM: brassica napus

<400> SEQUENCE: 396
ttgtgaaaag tcgc                                                         14

<210> SEQ ID NO 397
<211> LENGTH: 14
<212> TYPE: DNA
<213> ORGANISM: brassica napus

<400> SEQUENCE: 397
tgtgaaaagt cgct                                                         14

<210> SEQ ID NO 398
<211> LENGTH: 14
<212> TYPE: DNA
<213> ORGANISM: brassica napus

<400> SEQUENCE: 398
gtgaaaagtc gctg                                                         14

<210> SEQ ID NO 399
<211> LENGTH: 14
```

<212> TYPE: DNA
<213> ORGANISM: brassica napus

<400> SEQUENCE: 399
tgaaaagtcg ctga                                                         14

<210> SEQ ID NO 400
<211> LENGTH: 14
<212> TYPE: DNA
<213> ORGANISM: brassica napus

<400> SEQUENCE: 400
gaaaagtcgc tgat                                                         14

<210> SEQ ID NO 401
<211> LENGTH: 14
<212> TYPE: DNA
<213> ORGANISM: brassica napus

<400> SEQUENCE: 401
aaaagtcgct gatc                                                         14

<210> SEQ ID NO 402
<211> LENGTH: 14
<212> TYPE: DNA
<213> ORGANISM: brassica napus

<400> SEQUENCE: 402
aaagtcgctg atct                                                         14

<210> SEQ ID NO 403
<211> LENGTH: 14
<212> TYPE: DNA
<213> ORGANISM: brassica napus

<400> SEQUENCE: 403
aagtcgctga tctt                                                         14

<210> SEQ ID NO 404
<211> LENGTH: 14
<212> TYPE: DNA
<213> ORGANISM: brassica napus

<400> SEQUENCE: 404
agtcgctgat ctta                                                         14

<210> SEQ ID NO 405
<211> LENGTH: 14
<212> TYPE: DNA
<213> ORGANISM: brassica napus

<400> SEQUENCE: 405
caccctactt tgtg                                                         14

<210> SEQ ID NO 406
<211> LENGTH: 14
<212> TYPE: DNA
<213> ORGANISM: brassica napus

<400> SEQUENCE: 406
gtcgctgatc ttat                                                         14

<210> SEQ ID NO 407

```
<211> LENGTH: 14
<212> TYPE: DNA
<213> ORGANISM: brassica napus

<400> SEQUENCE: 407
tcgctgatct tatt                                                        14

<210> SEQ ID NO 408
<211> LENGTH: 14
<212> TYPE: DNA
<213> ORGANISM: brassica napus

<400> SEQUENCE: 408
accctacttt gtga                                                        14

<210> SEQ ID NO 409
<211> LENGTH: 14
<212> TYPE: DNA
<213> ORGANISM: brassica napus

<400> SEQUENCE: 409
ccctactttg tgaa                                                        14

<210> SEQ ID NO 410
<211> LENGTH: 14
<212> TYPE: DNA
<213> ORGANISM: brassica napus

<400> SEQUENCE: 410
cctactttgt gaaa                                                        14

<210> SEQ ID NO 411
<211> LENGTH: 14
<212> TYPE: DNA
<213> ORGANISM: brassica napus

<400> SEQUENCE: 411
ctactttgtg aaaa                                                        14

<210> SEQ ID NO 412
<211> LENGTH: 14
<212> TYPE: DNA
<213> ORGANISM: brassica napus

<400> SEQUENCE: 412
tactttgtga aaag                                                        14

<210> SEQ ID NO 413
<211> LENGTH: 14
<212> TYPE: DNA
<213> ORGANISM: brassica napus

<400> SEQUENCE: 413
actttgtgaa aagt                                                        14

<210> SEQ ID NO 414
<211> LENGTH: 14
<212> TYPE: DNA
<213> ORGANISM: brassica napus

<400> SEQUENCE: 414
ctttgtgaaa agtc                                                        14
```

-continued

```
<210> SEQ ID NO 415
<211> LENGTH: 15
<212> TYPE: DNA
<213> ORGANISM: brassica napus

<400> SEQUENCE: 415
acaccctact ttgtg                                                        15

<210> SEQ ID NO 416
<211> LENGTH: 15
<212> TYPE: DNA
<213> ORGANISM: brassica napus

<400> SEQUENCE: 416
tttgtgaaaa gtcgc                                                        15

<210> SEQ ID NO 417
<211> LENGTH: 15
<212> TYPE: DNA
<213> ORGANISM: brassica napus

<400> SEQUENCE: 417
ttgtgaaaag tcgct                                                        15

<210> SEQ ID NO 418
<211> LENGTH: 15
<212> TYPE: DNA
<213> ORGANISM: brassica napus

<400> SEQUENCE: 418
tgtgaaaagt cgctg                                                        15

<210> SEQ ID NO 419
<211> LENGTH: 15
<212> TYPE: DNA
<213> ORGANISM: brassica napus

<400> SEQUENCE: 419
gtgaaaagtc gctga                                                        15

<210> SEQ ID NO 420
<211> LENGTH: 15
<212> TYPE: DNA
<213> ORGANISM: brassica napus

<400> SEQUENCE: 420
tgaaaagtcg ctgat                                                        15

<210> SEQ ID NO 421
<211> LENGTH: 15
<212> TYPE: DNA
<213> ORGANISM: brassica napus

<400> SEQUENCE: 421
gaaaagtcgc tgatc                                                        15

<210> SEQ ID NO 422
<211> LENGTH: 15
<212> TYPE: DNA
<213> ORGANISM: brassica napus

<400> SEQUENCE: 422
aaaagtcgct gatct                                                        15
```

-continued

```
<210> SEQ ID NO 423
<211> LENGTH: 15
<212> TYPE: DNA
<213> ORGANISM: brassica napus

<400> SEQUENCE: 423
aaagtcgctg atctt                                                    15

<210> SEQ ID NO 424
<211> LENGTH: 15
<212> TYPE: DNA
<213> ORGANISM: brassica napus

<400> SEQUENCE: 424
aagtcgctga tctta                                                    15

<210> SEQ ID NO 425
<211> LENGTH: 15
<212> TYPE: DNA
<213> ORGANISM: brassica napus

<400> SEQUENCE: 425
agtcgctgat cttat                                                    15

<210> SEQ ID NO 426
<211> LENGTH: 15
<212> TYPE: DNA
<213> ORGANISM: brassica napus

<400> SEQUENCE: 426
caccctactt tgtga                                                    15

<210> SEQ ID NO 427
<211> LENGTH: 15
<212> TYPE: DNA
<213> ORGANISM: brassica napus

<400> SEQUENCE: 427
gtcgctgatc ttatt                                                    15

<210> SEQ ID NO 428
<211> LENGTH: 15
<212> TYPE: DNA
<213> ORGANISM: brassica napus

<400> SEQUENCE: 428
accctacttt gtgaa                                                    15

<210> SEQ ID NO 429
<211> LENGTH: 15
<212> TYPE: DNA
<213> ORGANISM: brassica napus

<400> SEQUENCE: 429
ccctactttg tgaaa                                                    15

<210> SEQ ID NO 430
<211> LENGTH: 15
<212> TYPE: DNA
<213> ORGANISM: brassica napus

<400> SEQUENCE: 430
cctactttgt gaaaa                                                    15
```

<210> SEQ ID NO 431
<211> LENGTH: 15
<212> TYPE: DNA
<213> ORGANISM: brassica napus

<400> SEQUENCE: 431
ctactttgtg aaaag                                                15

<210> SEQ ID NO 432
<211> LENGTH: 15
<212> TYPE: DNA
<213> ORGANISM: brassica napus

<400> SEQUENCE: 432
tactttgtga aaagt                                                15

<210> SEQ ID NO 433
<211> LENGTH: 15
<212> TYPE: DNA
<213> ORGANISM: brassica napus

<400> SEQUENCE: 433
actttgtgaa aagtc                                                15

<210> SEQ ID NO 434
<211> LENGTH: 15
<212> TYPE: DNA
<213> ORGANISM: brassica napus

<400> SEQUENCE: 434
ctttgtgaaa agtcg                                                15

<210> SEQ ID NO 435
<211> LENGTH: 16
<212> TYPE: DNA
<213> ORGANISM: brassica napus

<400> SEQUENCE: 435
acaccctact ttgtga                                               16

<210> SEQ ID NO 436
<211> LENGTH: 16
<212> TYPE: DNA
<213> ORGANISM: brassica napus

<400> SEQUENCE: 436
tttgtgaaaa gtcgct                                               16

<210> SEQ ID NO 437
<211> LENGTH: 16
<212> TYPE: DNA
<213> ORGANISM: brassica napus

<400> SEQUENCE: 437
ttgtgaaaag tcgctg                                               16

<210> SEQ ID NO 438
<211> LENGTH: 16
<212> TYPE: DNA
<213> ORGANISM: brassica napus

<400> SEQUENCE: 438

-continued

```
tgtgaaaagt cgctga                                            16

<210> SEQ ID NO 439
<211> LENGTH: 16
<212> TYPE: DNA
<213> ORGANISM: brassica napus

<400> SEQUENCE: 439
gtgaaaagtc gctgat                                            16

<210> SEQ ID NO 440
<211> LENGTH: 16
<212> TYPE: DNA
<213> ORGANISM: brassica napus

<400> SEQUENCE: 440
tgaaaagtcg ctgatc                                            16

<210> SEQ ID NO 441
<211> LENGTH: 16
<212> TYPE: DNA
<213> ORGANISM: brassica napus

<400> SEQUENCE: 441
gaaaagtcgc tgatct                                            16

<210> SEQ ID NO 442
<211> LENGTH: 16
<212> TYPE: DNA
<213> ORGANISM: brassica napus

<400> SEQUENCE: 442
aaaagtcgct gatctt                                            16

<210> SEQ ID NO 443
<211> LENGTH: 16
<212> TYPE: DNA
<213> ORGANISM: brassica napus

<400> SEQUENCE: 443
aaagtcgctg atctta                                            16

<210> SEQ ID NO 444
<211> LENGTH: 16
<212> TYPE: DNA
<213> ORGANISM: brassica napus

<400> SEQUENCE: 444
aagtcgctga tcttat                                            16

<210> SEQ ID NO 445
<211> LENGTH: 16
<212> TYPE: DNA
<213> ORGANISM: brassica napus

<400> SEQUENCE: 445
agtcgctgat cttatt                                            16

<210> SEQ ID NO 446
<211> LENGTH: 16
<212> TYPE: DNA
<213> ORGANISM: brassica napus

<400> SEQUENCE: 446
```

-continued

```
caccctactt tgtgaa                                              16

<210> SEQ ID NO 447
<211> LENGTH: 16
<212> TYPE: DNA
<213> ORGANISM: brassica napus

<400> SEQUENCE: 447
accctacttt gtgaaa                                              16

<210> SEQ ID NO 448
<211> LENGTH: 16
<212> TYPE: DNA
<213> ORGANISM: brassica napus

<400> SEQUENCE: 448
ccctactttg tgaaaa                                              16

<210> SEQ ID NO 449
<211> LENGTH: 16
<212> TYPE: DNA
<213> ORGANISM: brassica napus

<400> SEQUENCE: 449
cctactttgt gaaaag                                              16

<210> SEQ ID NO 450
<211> LENGTH: 16
<212> TYPE: DNA
<213> ORGANISM: brassica napus

<400> SEQUENCE: 450
ctactttgtg aaaagt                                              16

<210> SEQ ID NO 451
<211> LENGTH: 16
<212> TYPE: DNA
<213> ORGANISM: brassica napus

<400> SEQUENCE: 451
tactttgtga aaagtc                                              16

<210> SEQ ID NO 452
<211> LENGTH: 16
<212> TYPE: DNA
<213> ORGANISM: brassica napus

<400> SEQUENCE: 452
actttgtgaa aagtcg                                              16

<210> SEQ ID NO 453
<211> LENGTH: 16
<212> TYPE: DNA
<213> ORGANISM: brassica napus

<400> SEQUENCE: 453
ctttgtgaaa agtcgc                                              16

<210> SEQ ID NO 454
<211> LENGTH: 17
<212> TYPE: DNA
<213> ORGANISM: brassica napus
```

-continued

```
<400> SEQUENCE: 454
acaccctact ttgtgaa                                                17

<210> SEQ ID NO 455
<211> LENGTH: 17
<212> TYPE: DNA
<213> ORGANISM: brassica napus

<400> SEQUENCE: 455
tttgtgaaaa gtcgctg                                                17

<210> SEQ ID NO 456
<211> LENGTH: 17
<212> TYPE: DNA
<213> ORGANISM: brassica napus

<400> SEQUENCE: 456
ttgtgaaaag tcgctga                                                17

<210> SEQ ID NO 457
<211> LENGTH: 17
<212> TYPE: DNA
<213> ORGANISM: brassica napus

<400> SEQUENCE: 457
tgtgaaaagt cgctgat                                                17

<210> SEQ ID NO 458
<211> LENGTH: 17
<212> TYPE: DNA
<213> ORGANISM: brassica napus

<400> SEQUENCE: 458
gtgaaaagtc gctgatc                                                17

<210> SEQ ID NO 459
<211> LENGTH: 17
<212> TYPE: DNA
<213> ORGANISM: brassica napus

<400> SEQUENCE: 459
tgaaaagtcg ctgatct                                                17

<210> SEQ ID NO 460
<211> LENGTH: 17
<212> TYPE: DNA
<213> ORGANISM: brassica napus

<400> SEQUENCE: 460
gaaaagtcgc tgatctt                                                17

<210> SEQ ID NO 461
<211> LENGTH: 17
<212> TYPE: DNA
<213> ORGANISM: brassica napus

<400> SEQUENCE: 461
aaaagtcgct gatctta                                                17

<210> SEQ ID NO 462
<211> LENGTH: 17
<212> TYPE: DNA
<213> ORGANISM: brassica napus
```

```
<400> SEQUENCE: 462
aaagtcgctg atcttat                                              17

<210> SEQ ID NO 463
<211> LENGTH: 17
<212> TYPE: DNA
<213> ORGANISM: brassica napus

<400> SEQUENCE: 463
aagtcgctga tcttatt                                             17

<210> SEQ ID NO 464
<211> LENGTH: 17
<212> TYPE: DNA
<213> ORGANISM: brassica napus

<400> SEQUENCE: 464
caccctactt tgtgaaa                                             17

<210> SEQ ID NO 465
<211> LENGTH: 17
<212> TYPE: DNA
<213> ORGANISM: brassica napus

<400> SEQUENCE: 465
accctacttt gtgaaaa                                             17

<210> SEQ ID NO 466
<211> LENGTH: 17
<212> TYPE: DNA
<213> ORGANISM: brassica napus

<400> SEQUENCE: 466
ccctactttg tgaaaag                                             17

<210> SEQ ID NO 467
<211> LENGTH: 17
<212> TYPE: DNA
<213> ORGANISM: brassica napus

<400> SEQUENCE: 467
cctactttgt gaaaagt                                             17

<210> SEQ ID NO 468
<211> LENGTH: 17
<212> TYPE: DNA
<213> ORGANISM: brassica napus

<400> SEQUENCE: 468
ctactttgtg aaaagtc                                             17

<210> SEQ ID NO 469
<211> LENGTH: 17
<212> TYPE: DNA
<213> ORGANISM: brassica napus

<400> SEQUENCE: 469
tactttgtga aaagtcg                                             17

<210> SEQ ID NO 470
<211> LENGTH: 17
<212> TYPE: DNA
```

-continued

<213> ORGANISM: brassica napus

<400> SEQUENCE: 470
actttgtgaa aagtcgc                                                                          17

<210> SEQ ID NO 471
<211> LENGTH: 17
<212> TYPE: DNA
<213> ORGANISM: brassica napus

<400> SEQUENCE: 471
ctttgtgaaa agtcgct                                                                          17

<210> SEQ ID NO 472
<211> LENGTH: 18
<212> TYPE: DNA
<213> ORGANISM: brassica napus

<400> SEQUENCE: 472
acaccctact ttgtgaaa                                                                         18

<210> SEQ ID NO 473
<211> LENGTH: 18
<212> TYPE: DNA
<213> ORGANISM: brassica napus

<400> SEQUENCE: 473
tttgtgaaaa gtcgctga                                                                         18

<210> SEQ ID NO 474
<211> LENGTH: 18
<212> TYPE: DNA
<213> ORGANISM: brassica napus

<400> SEQUENCE: 474
ttgtgaaaag tcgctgat                                                                         18

<210> SEQ ID NO 475
<211> LENGTH: 18
<212> TYPE: DNA
<213> ORGANISM: brassica napus

<400> SEQUENCE: 475
tgtgaaaagt cgctgatc                                                                         18

<210> SEQ ID NO 476
<211> LENGTH: 18
<212> TYPE: DNA
<213> ORGANISM: brassica napus

<400> SEQUENCE: 476
tgaaaagtcg ctgatctt                                                                         18

<210> SEQ ID NO 477
<211> LENGTH: 18
<212> TYPE: DNA
<213> ORGANISM: brassica napus

<400> SEQUENCE: 477
gaaaagtcgc tgatctta                                                                         18

<210> SEQ ID NO 478
<211> LENGTH: 18

-continued

```
<212> TYPE: DNA
<213> ORGANISM: brassica napus

<400> SEQUENCE: 478
aaaagtcgct gatcttat                                          18

<210> SEQ ID NO 479
<211> LENGTH: 18
<212> TYPE: DNA
<213> ORGANISM: brassica napus

<400> SEQUENCE: 479
aaagtcgctg atcttatt                                          18

<210> SEQ ID NO 480
<211> LENGTH: 18
<212> TYPE: DNA
<213> ORGANISM: brassica napus

<400> SEQUENCE: 480
gtgaaaagtc gctgatct                                          18

<210> SEQ ID NO 481
<211> LENGTH: 18
<212> TYPE: DNA
<213> ORGANISM: brassica napus

<400> SEQUENCE: 481
caccctactt tgtgaaaa                                          18

<210> SEQ ID NO 482
<211> LENGTH: 18
<212> TYPE: DNA
<213> ORGANISM: brassica napus

<400> SEQUENCE: 482
accctacttt gtgaaaag                                          18

<210> SEQ ID NO 483
<211> LENGTH: 18
<212> TYPE: DNA
<213> ORGANISM: brassica napus

<400> SEQUENCE: 483
ccctactttg tgaaaagt                                          18

<210> SEQ ID NO 484
<211> LENGTH: 18
<212> TYPE: DNA
<213> ORGANISM: brassica napus

<400> SEQUENCE: 484
cctactttgt gaaaagtc                                          18

<210> SEQ ID NO 485
<211> LENGTH: 18
<212> TYPE: DNA
<213> ORGANISM: brassica napus

<400> SEQUENCE: 485
ctactttgtg aaaagtcg                                          18

<210> SEQ ID NO 486
```

-continued

<211> LENGTH: 18
<212> TYPE: DNA
<213> ORGANISM: brassica napus

<400> SEQUENCE: 486
tactttgtga aaagtcgc                                                    18

<210> SEQ ID NO 487
<211> LENGTH: 18
<212> TYPE: DNA
<213> ORGANISM: brassica napus

<400> SEQUENCE: 487
actttgtgaa aagtcgct                                                    18

<210> SEQ ID NO 488
<211> LENGTH: 18
<212> TYPE: DNA
<213> ORGANISM: brassica napus

<400> SEQUENCE: 488
ctttgtgaaa agtcgctg                                                    18

<210> SEQ ID NO 489
<211> LENGTH: 15
<212> TYPE: DNA
<213> ORGANISM: brassica napus

<400> SEQUENCE: 489
ttttaactat agtgg                                                       15

<210> SEQ ID NO 490
<211> LENGTH: 16
<212> TYPE: DNA
<213> ORGANISM: brassica napus

<400> SEQUENCE: 490
ttttaactat agtggc                                                      16

<210> SEQ ID NO 491
<211> LENGTH: 17
<212> TYPE: DNA
<213> ORGANISM: brassica napus

<400> SEQUENCE: 491
ttttaactat agtggcc                                                     17

<210> SEQ ID NO 492
<211> LENGTH: 18
<212> TYPE: DNA
<213> ORGANISM: brassica napus

<400> SEQUENCE: 492
ttttaactat agtggcct                                                    18

<210> SEQ ID NO 493
<211> LENGTH: 19
<212> TYPE: DNA
<213> ORGANISM: brassica napus

<400> SEQUENCE: 493
ttttaactat agtggcctt                                                   19

-continued

```
<210> SEQ ID NO 494
<211> LENGTH: 20
<212> TYPE: DNA
<213> ORGANISM: brassica napus

<400> SEQUENCE: 494
ttttaactat agtggccttc                                           20

<210> SEQ ID NO 495
<211> LENGTH: 21
<212> TYPE: DNA
<213> ORGANISM: brassica napus

<400> SEQUENCE: 495
ttttaactat agtggccttc a                                         21

<210> SEQ ID NO 496
<211> LENGTH: 22
<212> TYPE: DNA
<213> ORGANISM: brassica napus

<400> SEQUENCE: 496
ttttaactat agtggccttc ac                                        22

<210> SEQ ID NO 497
<211> LENGTH: 23
<212> TYPE: DNA
<213> ORGANISM: brassica napus

<400> SEQUENCE: 497
ttttaactat agtggccttc acg                                       23

<210> SEQ ID NO 498
<211> LENGTH: 15
<212> TYPE: DNA
<213> ORGANISM: brassica napus

<400> SEQUENCE: 498
tagtggcctt cacgc                                                15

<210> SEQ ID NO 499
<211> LENGTH: 16
<212> TYPE: DNA
<213> ORGANISM: brassica napus

<400> SEQUENCE: 499
tagtggcctt cacgct                                               16

<210> SEQ ID NO 500
<211> LENGTH: 17
<212> TYPE: DNA
<213> ORGANISM: brassica napus

<400> SEQUENCE: 500
tagtggcctt cacgctc                                              17

<210> SEQ ID NO 501
<211> LENGTH: 18
<212> TYPE: DNA
<213> ORGANISM: brassica napus

<400> SEQUENCE: 501
tagtggcctt cacgctcc                                             18
```

-continued

```
<210> SEQ ID NO 502
<211> LENGTH: 19
<212> TYPE: DNA
<213> ORGANISM: brassica napus

<400> SEQUENCE: 502
tagtggcctt cacgctccg                                          19

<210> SEQ ID NO 503
<211> LENGTH: 20
<212> TYPE: DNA
<213> ORGANISM: brassica napus

<400> SEQUENCE: 503
tagtggcctt cacgctccga                                         20

<210> SEQ ID NO 504
<211> LENGTH: 21
<212> TYPE: DNA
<213> ORGANISM: brassica napus

<400> SEQUENCE: 504
tagtggcctt cacgctccga t                                       21

<210> SEQ ID NO 505
<211> LENGTH: 22
<212> TYPE: DNA
<213> ORGANISM: brassica napus

<400> SEQUENCE: 505
tagtggcctt cacgctccga tg                                      22

<210> SEQ ID NO 506
<211> LENGTH: 23
<212> TYPE: DNA
<213> ORGANISM: brassica napus

<400> SEQUENCE: 506
tagtggcctt cacgctccga tgt                                     23

<210> SEQ ID NO 507
<211> LENGTH: 15
<212> TYPE: DNA
<213> ORGANISM: brassica napus

<400> SEQUENCE: 507
tgggtctttc aactg                                              15

<210> SEQ ID NO 508
<211> LENGTH: 16
<212> TYPE: DNA
<213> ORGANISM: brassica napus

<400> SEQUENCE: 508
tgggtctttc aactga                                             16

<210> SEQ ID NO 509
<211> LENGTH: 17
<212> TYPE: DNA
<213> ORGANISM: brassica napus

<400> SEQUENCE: 509
tgggtctttc aactgag                                            17
```

-continued

```
<210> SEQ ID NO 510
<211> LENGTH: 18
<212> TYPE: DNA
<213> ORGANISM: brassica napus

<400> SEQUENCE: 510
tgggtctttc aactgagc                                                      18

<210> SEQ ID NO 511
<211> LENGTH: 19
<212> TYPE: DNA
<213> ORGANISM: brassica napus

<400> SEQUENCE: 511
tgggtctttc aactgagct                                                     19

<210> SEQ ID NO 512
<211> LENGTH: 20
<212> TYPE: DNA
<213> ORGANISM: brassica napus

<400> SEQUENCE: 512
tgggtctttc aactgagctc                                                    20

<210> SEQ ID NO 513
<211> LENGTH: 21
<212> TYPE: DNA
<213> ORGANISM: brassica napus

<400> SEQUENCE: 513
tgggtctttc aactgagctc a                                                  21

<210> SEQ ID NO 514
<211> LENGTH: 22
<212> TYPE: DNA
<213> ORGANISM: brassica napus

<400> SEQUENCE: 514
tgggtctttc aactgagctc aa                                                 22

<210> SEQ ID NO 515
<211> LENGTH: 23
<212> TYPE: DNA
<213> ORGANISM: brassica napus

<400> SEQUENCE: 515
tgggtctttc aactgagctc aat                                                23

<210> SEQ ID NO 516
<211> LENGTH: 15
<212> TYPE: DNA
<213> ORGANISM: brassica napus

<400> SEQUENCE: 516
gggtctttca actga                                                         15

<210> SEQ ID NO 517
<211> LENGTH: 16
<212> TYPE: DNA
<213> ORGANISM: brassica napus

<400> SEQUENCE: 517
```

```
gggtctttca actgag                                                    16

<210> SEQ ID NO 518
<211> LENGTH: 17
<212> TYPE: DNA
<213> ORGANISM: brassica napus

<400> SEQUENCE: 518
gggtctttca actgagc                                                   17

<210> SEQ ID NO 519
<211> LENGTH: 18
<212> TYPE: DNA
<213> ORGANISM: brassica napus

<400> SEQUENCE: 519
gggtctttca actgagct                                                  18

<210> SEQ ID NO 520
<211> LENGTH: 19
<212> TYPE: DNA
<213> ORGANISM: brassica napus

<400> SEQUENCE: 520
gggtctttca actgagctc                                                 19

<210> SEQ ID NO 521
<211> LENGTH: 20
<212> TYPE: DNA
<213> ORGANISM: brassica napus

<400> SEQUENCE: 521
gggtctttca actgagctca                                                20

<210> SEQ ID NO 522
<211> LENGTH: 21
<212> TYPE: DNA
<213> ORGANISM: brassica napus

<400> SEQUENCE: 522
gggtctttca actgagctca a                                              21

<210> SEQ ID NO 523
<211> LENGTH: 22
<212> TYPE: DNA
<213> ORGANISM: brassica napus

<400> SEQUENCE: 523
gggtctttca actgagctca at                                             22

<210> SEQ ID NO 524
<211> LENGTH: 23
<212> TYPE: DNA
<213> ORGANISM: brassica napus

<400> SEQUENCE: 524
gggtctttca actgagctca ata                                            23

<210> SEQ ID NO 525
<211> LENGTH: 15
<212> TYPE: DNA
<213> ORGANISM: brassica napus

<400> SEQUENCE: 525
```

-continued ggtctttcaa ctgag                                                                        15

<210> SEQ ID NO 526
<211> LENGTH: 16
<212> TYPE: DNA
<213> ORGANISM: brassica napus

<400> SEQUENCE: 526
ggtctttcaa ctgagc                                                                       16

<210> SEQ ID NO 527
<211> LENGTH: 17
<212> TYPE: DNA
<213> ORGANISM: brassica napus

<400> SEQUENCE: 527
ggtctttcaa ctgagct                                                                      17

<210> SEQ ID NO 528
<211> LENGTH: 18
<212> TYPE: DNA
<213> ORGANISM: brassica napus

<400> SEQUENCE: 528
ggtctttcaa ctgagctc                                                                     18

<210> SEQ ID NO 529
<211> LENGTH: 19
<212> TYPE: DNA
<213> ORGANISM: brassica napus

<400> SEQUENCE: 529
ggtctttcaa ctgagctca                                                                    19

<210> SEQ ID NO 530
<211> LENGTH: 20
<212> TYPE: DNA
<213> ORGANISM: brassica napus

<400> SEQUENCE: 530
ggtctttcaa ctgagctcaa                                                                   20

<210> SEQ ID NO 531
<211> LENGTH: 21
<212> TYPE: DNA
<213> ORGANISM: brassica napus

<400> SEQUENCE: 531
ggtctttcaa ctgagctcaa t                                                                 21

<210> SEQ ID NO 532
<211> LENGTH: 22
<212> TYPE: DNA
<213> ORGANISM: brassica napus

<400> SEQUENCE: 532
ggtctttcaa ctgagctcaa ta                                                                22

<210> SEQ ID NO 533
<211> LENGTH: 23
<212> TYPE: DNA
<213> ORGANISM: brassica napus -continued

```
<400> SEQUENCE: 533
ggtctttcaa ctgagctcaa tat                                    23

<210> SEQ ID NO 534
<211> LENGTH: 15
<212> TYPE: DNA
<213> ORGANISM: brassica napus

<400> SEQUENCE: 534
gtctttcaac tgagc                                             15

<210> SEQ ID NO 535
<211> LENGTH: 16
<212> TYPE: DNA
<213> ORGANISM: brassica napus

<400> SEQUENCE: 535
gtctttcaac tgagct                                            16

<210> SEQ ID NO 536
<211> LENGTH: 17
<212> TYPE: DNA
<213> ORGANISM: brassica napus

<400> SEQUENCE: 536
gtctttcaac tgagctc                                           17

<210> SEQ ID NO 537
<211> LENGTH: 18
<212> TYPE: DNA
<213> ORGANISM: brassica napus

<400> SEQUENCE: 537
gtctttcaac tgagctca                                          18

<210> SEQ ID NO 538
<211> LENGTH: 19
<212> TYPE: DNA
<213> ORGANISM: brassica napus

<400> SEQUENCE: 538
gtctttcaac tgagctcaa                                         19

<210> SEQ ID NO 539
<211> LENGTH: 20
<212> TYPE: DNA
<213> ORGANISM: brassica napus

<400> SEQUENCE: 539
gtctttcaac tgagctcaat                                        20

<210> SEQ ID NO 540
<211> LENGTH: 21
<212> TYPE: DNA
<213> ORGANISM: brassica napus

<400> SEQUENCE: 540
gtctttcaac tgagctcaat a                                      21

<210> SEQ ID NO 541
<211> LENGTH: 22
<212> TYPE: DNA
<213> ORGANISM: brassica napus
```

-continued

<400> SEQUENCE: 541
gtctttcaac tgagctcaat at                                                            22

<210> SEQ ID NO 542
<211> LENGTH: 23
<212> TYPE: DNA
<213> ORGANISM: brassica napus

<400> SEQUENCE: 542
gtctttcaac tgagctcaat ata                                                           23

<210> SEQ ID NO 543
<211> LENGTH: 15
<212> TYPE: DNA
<213> ORGANISM: brassica napus

<400> SEQUENCE: 543
tctttcaact gagct                                                                    15

<210> SEQ ID NO 544
<211> LENGTH: 16
<212> TYPE: DNA
<213> ORGANISM: brassica napus

<400> SEQUENCE: 544
tctttcaact gagctc                                                                   16

<210> SEQ ID NO 545
<211> LENGTH: 17
<212> TYPE: DNA
<213> ORGANISM: brassica napus

<400> SEQUENCE: 545
tctttcaact gagctca                                                                  17

<210> SEQ ID NO 546
<211> LENGTH: 18
<212> TYPE: DNA
<213> ORGANISM: brassica napus

<400> SEQUENCE: 546
tctttcaact gagctcaa                                                                 18

<210> SEQ ID NO 547
<211> LENGTH: 19
<212> TYPE: DNA
<213> ORGANISM: brassica napus

<400> SEQUENCE: 547
tctttcaact gagctcaat                                                                19

<210> SEQ ID NO 548
<211> LENGTH: 20
<212> TYPE: DNA
<213> ORGANISM: brassica napus

<400> SEQUENCE: 548
tctttcaact gagctcaata                                                               20

<210> SEQ ID NO 549
<211> LENGTH: 21
<212> TYPE: DNA

-continued

<213> ORGANISM: brassica napus

<400> SEQUENCE: 549
tctttcaact gagctcaata t                                          21

<210> SEQ ID NO 550
<211> LENGTH: 22
<212> TYPE: DNA
<213> ORGANISM: brassica napus

<400> SEQUENCE: 550
tctttcaact gagctcaata ta                                         22

<210> SEQ ID NO 551
<211> LENGTH: 23
<212> TYPE: DNA
<213> ORGANISM: brassica napus

<400> SEQUENCE: 551
tctttcaact gagctcaata tac                                        23

<210> SEQ ID NO 552
<211> LENGTH: 15
<212> TYPE: DNA
<213> ORGANISM: brassica napus

<400> SEQUENCE: 552
ctttcaactg agctc                                                 15

<210> SEQ ID NO 553
<211> LENGTH: 16
<212> TYPE: DNA
<213> ORGANISM: brassica napus

<400> SEQUENCE: 553
ctttcaactg agctca                                                16

<210> SEQ ID NO 554
<211> LENGTH: 17
<212> TYPE: DNA
<213> ORGANISM: brassica napus

<400> SEQUENCE: 554
ctttcaactg agctcaa                                               17

<210> SEQ ID NO 555
<211> LENGTH: 18
<212> TYPE: DNA
<213> ORGANISM: brassica napus

<400> SEQUENCE: 555
ctttcaactg agctcaat                                              18

<210> SEQ ID NO 556
<211> LENGTH: 19
<212> TYPE: DNA
<213> ORGANISM: brassica napus

<400> SEQUENCE: 556
ctttcaactg agctcaata                                             19

<210> SEQ ID NO 557
<211> LENGTH: 20

-continued

```
<212> TYPE: DNA
<213> ORGANISM: brassica napus

<400> SEQUENCE: 557
ctttcaactg agctcaatat                                          20

<210> SEQ ID NO 558
<211> LENGTH: 21
<212> TYPE: DNA
<213> ORGANISM: brassica napus

<400> SEQUENCE: 558
ctttcaactg agctcaatat a                                        21

<210> SEQ ID NO 559
<211> LENGTH: 22
<212> TYPE: DNA
<213> ORGANISM: brassica napus

<400> SEQUENCE: 559
ctttcaactg agctcaatat ac                                       22

<210> SEQ ID NO 560
<211> LENGTH: 23
<212> TYPE: DNA
<213> ORGANISM: brassica napus

<400> SEQUENCE: 560
ctttcaactg agctcaatat aca                                      23

<210> SEQ ID NO 561
<211> LENGTH: 15
<212> TYPE: DNA
<213> ORGANISM: brassica napus

<400> SEQUENCE: 561
tttcaactga gctca                                               15

<210> SEQ ID NO 562
<211> LENGTH: 16
<212> TYPE: DNA
<213> ORGANISM: brassica napus

<400> SEQUENCE: 562
tttcaactga gctcaa                                              16

<210> SEQ ID NO 563
<211> LENGTH: 17
<212> TYPE: DNA
<213> ORGANISM: brassica napus

<400> SEQUENCE: 563
tttcaactga gctcaat                                             17

<210> SEQ ID NO 564
<211> LENGTH: 18
<212> TYPE: DNA
<213> ORGANISM: brassica napus

<400> SEQUENCE: 564
tttcaactga gctcaata                                            18

<210> SEQ ID NO 565
```

-continued

```
<211> LENGTH: 19
<212> TYPE: DNA
<213> ORGANISM: brassica napus

<400> SEQUENCE: 565
tttcaactga gctcaatat                                                    19

<210> SEQ ID NO 566
<211> LENGTH: 20
<212> TYPE: DNA
<213> ORGANISM: brassica napus

<400> SEQUENCE: 566
tttcaactga gctcaatata                                                   20

<210> SEQ ID NO 567
<211> LENGTH: 21
<212> TYPE: DNA
<213> ORGANISM: brassica napus

<400> SEQUENCE: 567
tttcaactga gctcaatata c                                                 21

<210> SEQ ID NO 568
<211> LENGTH: 22
<212> TYPE: DNA
<213> ORGANISM: brassica napus

<400> SEQUENCE: 568
tttcaactga gctcaatata ca                                                22

<210> SEQ ID NO 569
<211> LENGTH: 23
<212> TYPE: DNA
<213> ORGANISM: brassica napus

<400> SEQUENCE: 569
tttcaactga gctcaatata cac                                               23

<210> SEQ ID NO 570
<211> LENGTH: 15
<212> TYPE: DNA
<213> ORGANISM: brassica napus

<400> SEQUENCE: 570
ttcaactgag ctcaa                                                        15

<210> SEQ ID NO 571
<211> LENGTH: 16
<212> TYPE: DNA
<213> ORGANISM: brassica napus

<400> SEQUENCE: 571
ttcaactgag ctcaat                                                       16

<210> SEQ ID NO 572
<211> LENGTH: 17
<212> TYPE: DNA
<213> ORGANISM: brassica napus

<400> SEQUENCE: 572
ttcaactgag ctcaata                                                      17
```

US 12,698,539 B2

225

226

-continued

```
<210> SEQ ID NO 573
<211> LENGTH: 18
<212> TYPE: DNA
<213> ORGANISM: brassica napus

<400> SEQUENCE: 573
ttcaactgag ctcaatat                                              18

<210> SEQ ID NO 574
<211> LENGTH: 19
<212> TYPE: DNA
<213> ORGANISM: brassica napus

<400> SEQUENCE: 574
ttcaactgag ctcaatata                                             19

<210> SEQ ID NO 575
<211> LENGTH: 20
<212> TYPE: DNA
<213> ORGANISM: brassica napus

<400> SEQUENCE: 575
ttcaactgag ctcaatatac                                            20

<210> SEQ ID NO 576
<211> LENGTH: 21
<212> TYPE: DNA
<213> ORGANISM: brassica napus

<400> SEQUENCE: 576
ttcaactgag ctcaatatac a                                          21

<210> SEQ ID NO 577
<211> LENGTH: 22
<212> TYPE: DNA
<213> ORGANISM: brassica napus

<400> SEQUENCE: 577
ttcaactgag ctcaatatac ac                                         22

<210> SEQ ID NO 578
<211> LENGTH: 23
<212> TYPE: DNA
<213> ORGANISM: brassica napus

<400> SEQUENCE: 578
ttcaactgag ctcaatatac aca                                        23

<210> SEQ ID NO 579
<211> LENGTH: 15
<212> TYPE: DNA
<213> ORGANISM: brassica napus

<400> SEQUENCE: 579
tcaactgagc tcaat                                                 15

<210> SEQ ID NO 580
<211> LENGTH: 16
<212> TYPE: DNA
<213> ORGANISM: brassica napus

<400> SEQUENCE: 580
tcaactgagc tcaata                                                16
```

-continued

```
<210> SEQ ID NO 581
<211> LENGTH: 17
<212> TYPE: DNA
<213> ORGANISM: brassica napus

<400> SEQUENCE: 581
tcaactgagc tcaatat                                              17

<210> SEQ ID NO 582
<211> LENGTH: 18
<212> TYPE: DNA
<213> ORGANISM: brassica napus

<400> SEQUENCE: 582
tcaactgagc tcaatata                                             18

<210> SEQ ID NO 583
<211> LENGTH: 19
<212> TYPE: DNA
<213> ORGANISM: brassica napus

<400> SEQUENCE: 583
tcaactgagc tcaatatac                                            19

<210> SEQ ID NO 584
<211> LENGTH: 20
<212> TYPE: DNA
<213> ORGANISM: brassica napus

<400> SEQUENCE: 584
tcaactgagc tcaatataca                                           20

<210> SEQ ID NO 585
<211> LENGTH: 21
<212> TYPE: DNA
<213> ORGANISM: brassica napus

<400> SEQUENCE: 585
tcaactgagc tcaatataca c                                         21

<210> SEQ ID NO 586
<211> LENGTH: 22
<212> TYPE: DNA
<213> ORGANISM: brassica napus

<400> SEQUENCE: 586
tcaactgagc tcaatataca ca                                        22

<210> SEQ ID NO 587
<211> LENGTH: 23
<212> TYPE: DNA
<213> ORGANISM: brassica napus

<400> SEQUENCE: 587
tcaactgagc tcaatataca caa                                       23

<210> SEQ ID NO 588
<211> LENGTH: 15
<212> TYPE: DNA
<213> ORGANISM: brassica napus

<400> SEQUENCE: 588
caactgagct caata                                                15
```

<210> SEQ ID NO 589
<211> LENGTH: 16
<212> TYPE: DNA
<213> ORGANISM: brassica napus

<400> SEQUENCE: 589
caactgagct caatat                                                   16

<210> SEQ ID NO 590
<211> LENGTH: 17
<212> TYPE: DNA
<213> ORGANISM: brassica napus

<400> SEQUENCE: 590
caactgagct caatata                                                  17

<210> SEQ ID NO 591
<211> LENGTH: 18
<212> TYPE: DNA
<213> ORGANISM: brassica napus

<400> SEQUENCE: 591
caactgagct caatatac                                                 18

<210> SEQ ID NO 592
<211> LENGTH: 19
<212> TYPE: DNA
<213> ORGANISM: brassica napus

<400> SEQUENCE: 592
caactgagct caatataca                                                19

<210> SEQ ID NO 593
<211> LENGTH: 20
<212> TYPE: DNA
<213> ORGANISM: brassica napus

<400> SEQUENCE: 593
caactgagct caatatacac                                               20

<210> SEQ ID NO 594
<211> LENGTH: 21
<212> TYPE: DNA
<213> ORGANISM: brassica napus

<400> SEQUENCE: 594
caactgagct caatatacac a                                             21

<210> SEQ ID NO 595
<211> LENGTH: 22
<212> TYPE: DNA
<213> ORGANISM: brassica napus

<400> SEQUENCE: 595
caactgagct caatatacac aa                                            22

<210> SEQ ID NO 596
<211> LENGTH: 23
<212> TYPE: DNA
<213> ORGANISM: brassica napus

<400> SEQUENCE: 596

-continued

```
caactgagct caatatacac aag                                                    23

<210> SEQ ID NO 597
<211> LENGTH: 15
<212> TYPE: DNA
<213> ORGANISM: brassica napus

<400> SEQUENCE: 597
agtggccttc acgct                                                             15

<210> SEQ ID NO 598
<211> LENGTH: 16
<212> TYPE: DNA
<213> ORGANISM: brassica napus

<400> SEQUENCE: 598
agtggccttc acgctc                                                            16

<210> SEQ ID NO 599
<211> LENGTH: 17
<212> TYPE: DNA
<213> ORGANISM: brassica napus

<400> SEQUENCE: 599
agtggccttc acgctcc                                                           17

<210> SEQ ID NO 600
<211> LENGTH: 18
<212> TYPE: DNA
<213> ORGANISM: brassica napus

<400> SEQUENCE: 600
agtggccttc acgctccg                                                          18

<210> SEQ ID NO 601
<211> LENGTH: 19
<212> TYPE: DNA
<213> ORGANISM: brassica napus

<400> SEQUENCE: 601
agtggccttc acgctccga                                                         19

<210> SEQ ID NO 602
<211> LENGTH: 20
<212> TYPE: DNA
<213> ORGANISM: brassica napus

<400> SEQUENCE: 602
agtggccttc acgctccgat                                                        20

<210> SEQ ID NO 603
<211> LENGTH: 21
<212> TYPE: DNA
<213> ORGANISM: brassica napus

<400> SEQUENCE: 603
agtggccttc acgctccgat g                                                      21

<210> SEQ ID NO 604
<211> LENGTH: 22
<212> TYPE: DNA
<213> ORGANISM: brassica napus

<400> SEQUENCE: 604
```

-continued

```
agtggccttc acgctccgat gt                                             22

<210> SEQ ID NO 605
<211> LENGTH: 23
<212> TYPE: DNA
<213> ORGANISM: brassica napus

<400> SEQUENCE: 605
agtggccttc acgctccgat gtc                                            23

<210> SEQ ID NO 606
<211> LENGTH: 15
<212> TYPE: DNA
<213> ORGANISM: brassica napus

<400> SEQUENCE: 606
aactgagctc aatat                                                     15

<210> SEQ ID NO 607
<211> LENGTH: 16
<212> TYPE: DNA
<213> ORGANISM: brassica napus

<400> SEQUENCE: 607
aactgagctc aatata                                                    16

<210> SEQ ID NO 608
<211> LENGTH: 17
<212> TYPE: DNA
<213> ORGANISM: brassica napus

<400> SEQUENCE: 608
aactgagctc aatatac                                                   17

<210> SEQ ID NO 609
<211> LENGTH: 18
<212> TYPE: DNA
<213> ORGANISM: brassica napus

<400> SEQUENCE: 609
aactgagctc aatataca                                                  18

<210> SEQ ID NO 610
<211> LENGTH: 19
<212> TYPE: DNA
<213> ORGANISM: brassica napus

<400> SEQUENCE: 610
aactgagctc aatatacac                                                 19

<210> SEQ ID NO 611
<211> LENGTH: 20
<212> TYPE: DNA
<213> ORGANISM: brassica napus

<400> SEQUENCE: 611
aactgagctc aatatacaca                                                20

<210> SEQ ID NO 612
<211> LENGTH: 21
<212> TYPE: DNA
<213> ORGANISM: brassica napus
```

-continued

```
<400> SEQUENCE: 612
aactgagctc aatatacaca a                                          21

<210> SEQ ID NO 613
<211> LENGTH: 22
<212> TYPE: DNA
<213> ORGANISM: brassica napus

<400> SEQUENCE: 613
aactgagctc aatatacaca ag                                         22

<210> SEQ ID NO 614
<211> LENGTH: 23
<212> TYPE: DNA
<213> ORGANISM: brassica napus

<400> SEQUENCE: 614
aactgagctc aatatacaca aga                                        23

<210> SEQ ID NO 615
<211> LENGTH: 15
<212> TYPE: DNA
<213> ORGANISM: brassica napus

<400> SEQUENCE: 615
actgagctca atata                                                 15

<210> SEQ ID NO 616
<211> LENGTH: 16
<212> TYPE: DNA
<213> ORGANISM: brassica napus

<400> SEQUENCE: 616
actgagctca atatac                                                16

<210> SEQ ID NO 617
<211> LENGTH: 17
<212> TYPE: DNA
<213> ORGANISM: brassica napus

<400> SEQUENCE: 617
actgagctca atataca                                               17

<210> SEQ ID NO 618
<211> LENGTH: 18
<212> TYPE: DNA
<213> ORGANISM: brassica napus

<400> SEQUENCE: 618
actgagctca atatacac                                              18

<210> SEQ ID NO 619
<211> LENGTH: 19
<212> TYPE: DNA
<213> ORGANISM: brassica napus

<400> SEQUENCE: 619
actgagctca atatacaca                                             19

<210> SEQ ID NO 620
<211> LENGTH: 20
<212> TYPE: DNA
<213> ORGANISM: brassica napus
```

```
<400> SEQUENCE: 620
actgagctca atatacacaa                                                    20

<210> SEQ ID NO 621
<211> LENGTH: 21
<212> TYPE: DNA
<213> ORGANISM: brassica napus

<400> SEQUENCE: 621
actgagctca atatacacaa g                                                  21

<210> SEQ ID NO 622
<211> LENGTH: 22
<212> TYPE: DNA
<213> ORGANISM: brassica napus

<400> SEQUENCE: 622
actgagctca atatacacaa ga                                                 22

<210> SEQ ID NO 623
<211> LENGTH: 23
<212> TYPE: DNA
<213> ORGANISM: brassica napus

<400> SEQUENCE: 623
actgagctca atatacacaa gaa                                                23

<210> SEQ ID NO 624
<211> LENGTH: 15
<212> TYPE: DNA
<213> ORGANISM: brassica napus

<400> SEQUENCE: 624
ctgagctcaa tatac                                                         15

<210> SEQ ID NO 625
<211> LENGTH: 16
<212> TYPE: DNA
<213> ORGANISM: brassica napus

<400> SEQUENCE: 625
ctgagctcaa tataca                                                        16

<210> SEQ ID NO 626
<211> LENGTH: 17
<212> TYPE: DNA
<213> ORGANISM: brassica napus

<400> SEQUENCE: 626
ctgagctcaa tatacac                                                       17

<210> SEQ ID NO 627
<211> LENGTH: 18
<212> TYPE: DNA
<213> ORGANISM: brassica napus

<400> SEQUENCE: 627
ctgagctcaa tatacaca                                                      18

<210> SEQ ID NO 628
<211> LENGTH: 19
<212> TYPE: DNA
```

-continued

```
<213> ORGANISM: brassica napus

<400> SEQUENCE: 628
ctgagctcaa tatacacaa                                                    19

<210> SEQ ID NO 629
<211> LENGTH: 20
<212> TYPE: DNA
<213> ORGANISM: brassica napus

<400> SEQUENCE: 629
ctgagctcaa tatacacaag                                                   20

<210> SEQ ID NO 630
<211> LENGTH: 21
<212> TYPE: DNA
<213> ORGANISM: brassica napus

<400> SEQUENCE: 630
ctgagctcaa tatacacaag a                                                 21

<210> SEQ ID NO 631
<211> LENGTH: 22
<212> TYPE: DNA
<213> ORGANISM: brassica napus

<400> SEQUENCE: 631
ctgagctcaa tatacacaag aa                                                22

<210> SEQ ID NO 632
<211> LENGTH: 23
<212> TYPE: DNA
<213> ORGANISM: brassica napus

<400> SEQUENCE: 632
ctgagctcaa tatacacaag aaa                                               23

<210> SEQ ID NO 633
<211> LENGTH: 15
<212> TYPE: DNA
<213> ORGANISM: brassica napus

<400> SEQUENCE: 633
tgagctcaat ataca                                                        15

<210> SEQ ID NO 634
<211> LENGTH: 16
<212> TYPE: DNA
<213> ORGANISM: brassica napus

<400> SEQUENCE: 634
tgagctcaat atacac                                                       16

<210> SEQ ID NO 635
<211> LENGTH: 17
<212> TYPE: DNA
<213> ORGANISM: brassica napus

<400> SEQUENCE: 635
tgagctcaat atacaca                                                      17

<210> SEQ ID NO 636
<211> LENGTH: 18
```

<212> TYPE: DNA
<213> ORGANISM: brassica napus

<400> SEQUENCE: 636
tgagctcaat atacacaa                                                                          18

<210> SEQ ID NO 637
<211> LENGTH: 19
<212> TYPE: DNA
<213> ORGANISM: brassica napus

<400> SEQUENCE: 637
tgagctcaat atacacaag                                                                         19

<210> SEQ ID NO 638
<211> LENGTH: 20
<212> TYPE: DNA
<213> ORGANISM: brassica napus

<400> SEQUENCE: 638
tgagctcaat atacacaaga                                                                        20

<210> SEQ ID NO 639
<211> LENGTH: 21
<212> TYPE: DNA
<213> ORGANISM: brassica napus

<400> SEQUENCE: 639
tgagctcaat atacacaaga a                                                                      21

<210> SEQ ID NO 640
<211> LENGTH: 22
<212> TYPE: DNA
<213> ORGANISM: brassica napus

<400> SEQUENCE: 640
tgagctcaat atacacaaga aa                                                                     22

<210> SEQ ID NO 641
<211> LENGTH: 23
<212> TYPE: DNA
<213> ORGANISM: brassica napus

<400> SEQUENCE: 641
tgagctcaat atacacaaga aac                                                                    23

<210> SEQ ID NO 642
<211> LENGTH: 15
<212> TYPE: DNA
<213> ORGANISM: brassica napus

<400> SEQUENCE: 642
gagctcaata tacac                                                                             15

<210> SEQ ID NO 643
<211> LENGTH: 16
<212> TYPE: DNA
<213> ORGANISM: brassica napus

<400> SEQUENCE: 643
gagctcaata tacaca                                                                            16

<210> SEQ ID NO 644

```
<211> LENGTH: 17
<212> TYPE: DNA
<213> ORGANISM: brassica napus

<400> SEQUENCE: 644
gagctcaata tacacaa                                                17

<210> SEQ ID NO 645
<211> LENGTH: 18
<212> TYPE: DNA
<213> ORGANISM: brassica napus

<400> SEQUENCE: 645
gagctcaata tacacaag                                               18

<210> SEQ ID NO 646
<211> LENGTH: 19
<212> TYPE: DNA
<213> ORGANISM: brassica napus

<400> SEQUENCE: 646
gagctcaata tacacaaga                                              19

<210> SEQ ID NO 647
<211> LENGTH: 20
<212> TYPE: DNA
<213> ORGANISM: brassica napus

<400> SEQUENCE: 647
gagctcaata tacacaagaa                                             20

<210> SEQ ID NO 648
<211> LENGTH: 21
<212> TYPE: DNA
<213> ORGANISM: brassica napus

<400> SEQUENCE: 648
gagctcaata tacacaagaa a                                           21

<210> SEQ ID NO 649
<211> LENGTH: 22
<212> TYPE: DNA
<213> ORGANISM: brassica napus

<400> SEQUENCE: 649
gagctcaata tacacaagaa ac                                          22

<210> SEQ ID NO 650
<211> LENGTH: 23
<212> TYPE: DNA
<213> ORGANISM: brassica napus

<400> SEQUENCE: 650
gagctcaata tacacaagaa aca                                         23

<210> SEQ ID NO 651
<211> LENGTH: 15
<212> TYPE: DNA
<213> ORGANISM: brassica napus

<400> SEQUENCE: 651
agctcaatat acaca                                                  15
```

-continued

```
<210> SEQ ID NO 652
<211> LENGTH: 16
<212> TYPE: DNA
<213> ORGANISM: brassica napus

<400> SEQUENCE: 652
agctcaatat acacaa                                               16

<210> SEQ ID NO 653
<211> LENGTH: 17
<212> TYPE: DNA
<213> ORGANISM: brassica napus

<400> SEQUENCE: 653
agctcaatat acacaag                                              17

<210> SEQ ID NO 654
<211> LENGTH: 18
<212> TYPE: DNA
<213> ORGANISM: brassica napus

<400> SEQUENCE: 654
agctcaatat acacaaga                                             18

<210> SEQ ID NO 655
<211> LENGTH: 19
<212> TYPE: DNA
<213> ORGANISM: brassica napus

<400> SEQUENCE: 655
agctcaatat acacaagaa                                            19

<210> SEQ ID NO 656
<211> LENGTH: 20
<212> TYPE: DNA
<213> ORGANISM: brassica napus

<400> SEQUENCE: 656
agctcaatat acacaagaaa                                           20

<210> SEQ ID NO 657
<211> LENGTH: 21
<212> TYPE: DNA
<213> ORGANISM: brassica napus

<400> SEQUENCE: 657
agctcaatat acacaagaaa c                                         21

<210> SEQ ID NO 658
<211> LENGTH: 22
<212> TYPE: DNA
<213> ORGANISM: brassica napus

<400> SEQUENCE: 658
agctcaatat acacaagaaa ca                                        22

<210> SEQ ID NO 659
<211> LENGTH: 23
<212> TYPE: DNA
<213> ORGANISM: brassica napus

<400> SEQUENCE: 659
agctcaatat acacaagaaa cac                                       23
```

-continued

```
<210> SEQ ID NO 660
<211> LENGTH: 15
<212> TYPE: DNA
<213> ORGANISM: brassica napus

<400> SEQUENCE: 660
gctcaatata cacaa                                                    15

<210> SEQ ID NO 661
<211> LENGTH: 16
<212> TYPE: DNA
<213> ORGANISM: brassica napus

<400> SEQUENCE: 661
gctcaatata cacaag                                                   16

<210> SEQ ID NO 662
<211> LENGTH: 17
<212> TYPE: DNA
<213> ORGANISM: brassica napus

<400> SEQUENCE: 662
gctcaatata cacaaga                                                  17

<210> SEQ ID NO 663
<211> LENGTH: 18
<212> TYPE: DNA
<213> ORGANISM: brassica napus

<400> SEQUENCE: 663
gctcaatata cacaagaa                                                 18

<210> SEQ ID NO 664
<211> LENGTH: 19
<212> TYPE: DNA
<213> ORGANISM: brassica napus

<400> SEQUENCE: 664
gctcaatata cacaagaaa                                                19

<210> SEQ ID NO 665
<211> LENGTH: 20
<212> TYPE: DNA
<213> ORGANISM: brassica napus

<400> SEQUENCE: 665
gctcaatata cacaagaaac                                               20

<210> SEQ ID NO 666
<211> LENGTH: 21
<212> TYPE: DNA
<213> ORGANISM: brassica napus

<400> SEQUENCE: 666
gctcaatata cacaagaaac a                                             21

<210> SEQ ID NO 667
<211> LENGTH: 22
<212> TYPE: DNA
<213> ORGANISM: brassica napus

<400> SEQUENCE: 667
gctcaatata cacaagaaac ac                                            22
```

-continued

```
<210> SEQ ID NO 668
<211> LENGTH: 23
<212> TYPE: DNA
<213> ORGANISM: brassica napus

<400> SEQUENCE: 668
gctcaatata cacaagaaac acc                                          23

<210> SEQ ID NO 669
<211> LENGTH: 15
<212> TYPE: DNA
<213> ORGANISM: brassica napus

<400> SEQUENCE: 669
ctcaatatac acaag                                                   15

<210> SEQ ID NO 670
<211> LENGTH: 16
<212> TYPE: DNA
<213> ORGANISM: brassica napus

<400> SEQUENCE: 670
ctcaatatac acaaga                                                  16

<210> SEQ ID NO 671
<211> LENGTH: 17
<212> TYPE: DNA
<213> ORGANISM: brassica napus

<400> SEQUENCE: 671
ctcaatatac acaagaa                                                 17

<210> SEQ ID NO 672
<211> LENGTH: 18
<212> TYPE: DNA
<213> ORGANISM: brassica napus

<400> SEQUENCE: 672
ctcaatatac acaagaaa                                                18

<210> SEQ ID NO 673
<211> LENGTH: 19
<212> TYPE: DNA
<213> ORGANISM: brassica napus

<400> SEQUENCE: 673
ctcaatatac acaagaaac                                               19

<210> SEQ ID NO 674
<211> LENGTH: 20
<212> TYPE: DNA
<213> ORGANISM: brassica napus

<400> SEQUENCE: 674
ctcaatatac acaagaaaca                                              20

<210> SEQ ID NO 675
<211> LENGTH: 21
<212> TYPE: DNA
<213> ORGANISM: brassica napus

<400> SEQUENCE: 675
```

-continued

```
ctcaatatac acaagaaaca c                                                21

<210> SEQ ID NO 676
<211> LENGTH: 22
<212> TYPE: DNA
<213> ORGANISM: brassica napus

<400> SEQUENCE: 676
ctcaatatac acaagaaaca cc                                               22

<210> SEQ ID NO 677
<211> LENGTH: 23
<212> TYPE: DNA
<213> ORGANISM: brassica napus

<400> SEQUENCE: 677
ctcaatatac acaagaaaca cct                                              23

<210> SEQ ID NO 678
<211> LENGTH: 15
<212> TYPE: DNA
<213> ORGANISM: brassica napus

<400> SEQUENCE: 678
tcaatataca caaga                                                       15

<210> SEQ ID NO 679
<211> LENGTH: 16
<212> TYPE: DNA
<213> ORGANISM: brassica napus

<400> SEQUENCE: 679
tcaatataca caagaa                                                      16

<210> SEQ ID NO 680
<211> LENGTH: 17
<212> TYPE: DNA
<213> ORGANISM: brassica napus

<400> SEQUENCE: 680
tcaatataca caagaaa                                                     17

<210> SEQ ID NO 681
<211> LENGTH: 18
<212> TYPE: DNA
<213> ORGANISM: brassica napus

<400> SEQUENCE: 681
tcaatataca caagaaac                                                    18

<210> SEQ ID NO 682
<211> LENGTH: 19
<212> TYPE: DNA
<213> ORGANISM: brassica napus

<400> SEQUENCE: 682
tcaatataca caagaaaca                                                   19

<210> SEQ ID NO 683
<211> LENGTH: 20
<212> TYPE: DNA
<213> ORGANISM: brassica napus

<400> SEQUENCE: 683
```

-continued tcaatataca caagaaacac                                          20

<210> SEQ ID NO 684
<211> LENGTH: 21
<212> TYPE: DNA
<213> ORGANISM: brassica napus

<400> SEQUENCE: 684
tcaatataca caagaaacac c                                        21

<210> SEQ ID NO 685
<211> LENGTH: 22
<212> TYPE: DNA
<213> ORGANISM: brassica napus

<400> SEQUENCE: 685
tcaatataca caagaaacac ct                                       22

<210> SEQ ID NO 686
<211> LENGTH: 23
<212> TYPE: DNA
<213> ORGANISM: brassica napus

<400> SEQUENCE: 686
tcaatataca caagaaacac ctt                                      23

<210> SEQ ID NO 687
<211> LENGTH: 15
<212> TYPE: DNA
<213> ORGANISM: brassica napus

<400> SEQUENCE: 687
caatatacac aagaa                                               15

<210> SEQ ID NO 688
<211> LENGTH: 16
<212> TYPE: DNA
<213> ORGANISM: brassica napus

<400> SEQUENCE: 688
caatatacac aagaaa                                              16

<210> SEQ ID NO 689
<211> LENGTH: 17
<212> TYPE: DNA
<213> ORGANISM: brassica napus

<400> SEQUENCE: 689
caatatacac aagaaac                                             17

<210> SEQ ID NO 690
<211> LENGTH: 18
<212> TYPE: DNA
<213> ORGANISM: brassica napus

<400> SEQUENCE: 690
caatatacac aagaaaca                                            18

<210> SEQ ID NO 691
<211> LENGTH: 19
<212> TYPE: DNA
<213> ORGANISM: brassica napus -continued

```
<400> SEQUENCE: 691
caatatacac aagaaacac                                             19

<210> SEQ ID NO 692
<211> LENGTH: 20
<212> TYPE: DNA
<213> ORGANISM: brassica napus

<400> SEQUENCE: 692
caatatacac aagaaacacc                                            20

<210> SEQ ID NO 693
<211> LENGTH: 21
<212> TYPE: DNA
<213> ORGANISM: brassica napus

<400> SEQUENCE: 693
caatatacac aagaaacacc t                                          21

<210> SEQ ID NO 694
<211> LENGTH: 22
<212> TYPE: DNA
<213> ORGANISM: brassica napus

<400> SEQUENCE: 694
caatatacac aagaaacacc tt                                         22

<210> SEQ ID NO 695
<211> LENGTH: 23
<212> TYPE: DNA
<213> ORGANISM: brassica napus

<400> SEQUENCE: 695
caatatacac aagaaacacc tta                                        23

<210> SEQ ID NO 696
<211> LENGTH: 15
<212> TYPE: DNA
<213> ORGANISM: brassica napus

<400> SEQUENCE: 696
gtggccttca cgctc                                                 15

<210> SEQ ID NO 697
<211> LENGTH: 16
<212> TYPE: DNA
<213> ORGANISM: brassica napus

<400> SEQUENCE: 697
gtggccttca cgctcc                                                16

<210> SEQ ID NO 698
<211> LENGTH: 17
<212> TYPE: DNA
<213> ORGANISM: brassica napus

<400> SEQUENCE: 698
gtggccttca cgctccg                                               17

<210> SEQ ID NO 699
<211> LENGTH: 18
<212> TYPE: DNA
<213> ORGANISM: brassica napus
```

-continued

```
<400> SEQUENCE: 699
gtggccttca cgctccga                                            18

<210> SEQ ID NO 700
<211> LENGTH: 19
<212> TYPE: DNA
<213> ORGANISM: brassica napus

<400> SEQUENCE: 700
gtggccttca cgctccgat                                           19

<210> SEQ ID NO 701
<211> LENGTH: 20
<212> TYPE: DNA
<213> ORGANISM: brassica napus

<400> SEQUENCE: 701
gtggccttca cgctccgatg                                          20

<210> SEQ ID NO 702
<211> LENGTH: 21
<212> TYPE: DNA
<213> ORGANISM: brassica napus

<400> SEQUENCE: 702
gtggccttca cgctccgatg t                                        21

<210> SEQ ID NO 703
<211> LENGTH: 22
<212> TYPE: DNA
<213> ORGANISM: brassica napus

<400> SEQUENCE: 703
gtggccttca cgctccgatg tc                                       22

<210> SEQ ID NO 704
<211> LENGTH: 23
<212> TYPE: DNA
<213> ORGANISM: brassica napus

<400> SEQUENCE: 704
gtggccttca cgctccgatg tct                                      23

<210> SEQ ID NO 705
<211> LENGTH: 15
<212> TYPE: DNA
<213> ORGANISM: brassica napus

<400> SEQUENCE: 705
aatatacaca agaaa                                               15

<210> SEQ ID NO 706
<211> LENGTH: 16
<212> TYPE: DNA
<213> ORGANISM: brassica napus

<400> SEQUENCE: 706
aatatacaca agaaac                                              16

<210> SEQ ID NO 707
<211> LENGTH: 17
<212> TYPE: DNA
```

-continued

<213> ORGANISM: brassica napus

<400> SEQUENCE: 707
aatatacaca agaaaca                                          17

<210> SEQ ID NO 708
<211> LENGTH: 18
<212> TYPE: DNA
<213> ORGANISM: brassica napus

<400> SEQUENCE: 708
aatatacaca agaaacac                                         18

<210> SEQ ID NO 709
<211> LENGTH: 19
<212> TYPE: DNA
<213> ORGANISM: brassica napus

<400> SEQUENCE: 709
aatatacaca agaaacacc                                        19

<210> SEQ ID NO 710
<211> LENGTH: 20
<212> TYPE: DNA
<213> ORGANISM: brassica napus

<400> SEQUENCE: 710
aatatacaca agaaacacct                                       20

<210> SEQ ID NO 711
<211> LENGTH: 21
<212> TYPE: DNA
<213> ORGANISM: brassica napus

<400> SEQUENCE: 711
aatatacaca agaaacacct t                                     21

<210> SEQ ID NO 712
<211> LENGTH: 22
<212> TYPE: DNA
<213> ORGANISM: brassica napus

<400> SEQUENCE: 712
aatatacaca agaaacacct ta                                    22

<210> SEQ ID NO 713
<211> LENGTH: 23
<212> TYPE: DNA
<213> ORGANISM: brassica napus

<400> SEQUENCE: 713
aatatacaca agaaacacct tac                                   23

<210> SEQ ID NO 714
<211> LENGTH: 15
<212> TYPE: DNA
<213> ORGANISM: brassica napus

<400> SEQUENCE: 714
atatacacaa gaaac                                            15

<210> SEQ ID NO 715
<211> LENGTH: 16

-continued

```
<212> TYPE: DNA
<213> ORGANISM: brassica napus

<400> SEQUENCE: 715
atatacacaa gaaaca                                                    16

<210> SEQ ID NO 716
<211> LENGTH: 17
<212> TYPE: DNA
<213> ORGANISM: brassica napus

<400> SEQUENCE: 716
atatacacaa gaaacac                                                   17

<210> SEQ ID NO 717
<211> LENGTH: 18
<212> TYPE: DNA
<213> ORGANISM: brassica napus

<400> SEQUENCE: 717
atatacacaa gaaacacc                                                  18

<210> SEQ ID NO 718
<211> LENGTH: 19
<212> TYPE: DNA
<213> ORGANISM: brassica napus

<400> SEQUENCE: 718
atatacacaa gaaacacct                                                 19

<210> SEQ ID NO 719
<211> LENGTH: 20
<212> TYPE: DNA
<213> ORGANISM: brassica napus

<400> SEQUENCE: 719
atatacacaa gaaacacctt                                                20

<210> SEQ ID NO 720
<211> LENGTH: 21
<212> TYPE: DNA
<213> ORGANISM: brassica napus

<400> SEQUENCE: 720
atatacacaa gaaacacctt a                                              21

<210> SEQ ID NO 721
<211> LENGTH: 22
<212> TYPE: DNA
<213> ORGANISM: brassica napus

<400> SEQUENCE: 721
atatacacaa gaaacacctt ac                                             22

<210> SEQ ID NO 722
<211> LENGTH: 23
<212> TYPE: DNA
<213> ORGANISM: brassica napus

<400> SEQUENCE: 722
atatacacaa gaaacacctt act                                            23

<210> SEQ ID NO 723
```

-continued

```
<211> LENGTH: 15
<212> TYPE: DNA
<213> ORGANISM: brassica napus

<400> SEQUENCE: 723
tatacacaag aaaca                                                       15

<210> SEQ ID NO 724
<211> LENGTH: 16
<212> TYPE: DNA
<213> ORGANISM: brassica napus

<400> SEQUENCE: 724
tatacacaag aaacac                                                      16

<210> SEQ ID NO 725
<211> LENGTH: 17
<212> TYPE: DNA
<213> ORGANISM: brassica napus

<400> SEQUENCE: 725
tatacacaag aaacacc                                                     17

<210> SEQ ID NO 726
<211> LENGTH: 18
<212> TYPE: DNA
<213> ORGANISM: brassica napus

<400> SEQUENCE: 726
tatacacaag aaacacct                                                    18

<210> SEQ ID NO 727
<211> LENGTH: 19
<212> TYPE: DNA
<213> ORGANISM: brassica napus

<400> SEQUENCE: 727
tatacacaag aaacacctt                                                   19

<210> SEQ ID NO 728
<211> LENGTH: 20
<212> TYPE: DNA
<213> ORGANISM: brassica napus

<400> SEQUENCE: 728
tatacacaag aaacacctta                                                  20

<210> SEQ ID NO 729
<211> LENGTH: 21
<212> TYPE: DNA
<213> ORGANISM: brassica napus

<400> SEQUENCE: 729
tatacacaag aaacacctta c                                                21

<210> SEQ ID NO 730
<211> LENGTH: 22
<212> TYPE: DNA
<213> ORGANISM: brassica napus

<400> SEQUENCE: 730
tatacacaag aaacacctta ct                                               22
```

-continued

```
<210> SEQ ID NO 731
<211> LENGTH: 23
<212> TYPE: DNA
<213> ORGANISM: brassica napus

<400> SEQUENCE: 731
tatacacaag aaacaccttta ctt                                         23

<210> SEQ ID NO 732
<211> LENGTH: 15
<212> TYPE: DNA
<213> ORGANISM: brassica napus

<400> SEQUENCE: 732
atacacaaga aacac                                                   15

<210> SEQ ID NO 733
<211> LENGTH: 16
<212> TYPE: DNA
<213> ORGANISM: brassica napus

<400> SEQUENCE: 733
atacacaaga aacacc                                                  16

<210> SEQ ID NO 734
<211> LENGTH: 17
<212> TYPE: DNA
<213> ORGANISM: brassica napus

<400> SEQUENCE: 734
atacacaaga aacacct                                                 17

<210> SEQ ID NO 735
<211> LENGTH: 18
<212> TYPE: DNA
<213> ORGANISM: brassica napus

<400> SEQUENCE: 735
atacacaaga aacacctt                                                18

<210> SEQ ID NO 736
<211> LENGTH: 19
<212> TYPE: DNA
<213> ORGANISM: brassica napus

<400> SEQUENCE: 736
atacacaaga aacaccttta                                              19

<210> SEQ ID NO 737
<211> LENGTH: 20
<212> TYPE: DNA
<213> ORGANISM: brassica napus

<400> SEQUENCE: 737
atacacaaga aacaccttac                                              20

<210> SEQ ID NO 738
<211> LENGTH: 21
<212> TYPE: DNA
<213> ORGANISM: brassica napus

<400> SEQUENCE: 738
atacacaaga aacaccttac t                                            21
```

-continued

```
<210> SEQ ID NO 739
<211> LENGTH: 22
<212> TYPE: DNA
<213> ORGANISM: brassica napus

<400> SEQUENCE: 739
atacacaaga aacaccttac tt                                              22

<210> SEQ ID NO 740
<211> LENGTH: 23
<212> TYPE: DNA
<213> ORGANISM: brassica napus

<400> SEQUENCE: 740
atacacaaga aacaccttac ttt                                             23

<210> SEQ ID NO 741
<211> LENGTH: 15
<212> TYPE: DNA
<213> ORGANISM: brassica napus

<400> SEQUENCE: 741
tacacaagaa acacc                                                      15

<210> SEQ ID NO 742
<211> LENGTH: 16
<212> TYPE: DNA
<213> ORGANISM: brassica napus

<400> SEQUENCE: 742
tacacaagaa acacct                                                     16

<210> SEQ ID NO 743
<211> LENGTH: 17
<212> TYPE: DNA
<213> ORGANISM: brassica napus

<400> SEQUENCE: 743
tacacaagaa acacctt                                                    17

<210> SEQ ID NO 744
<211> LENGTH: 18
<212> TYPE: DNA
<213> ORGANISM: brassica napus

<400> SEQUENCE: 744
tacacaagaa acacctta                                                   18

<210> SEQ ID NO 745
<211> LENGTH: 19
<212> TYPE: DNA
<213> ORGANISM: brassica napus

<400> SEQUENCE: 745
tacacaagaa acaccttac                                                  19

<210> SEQ ID NO 746
<211> LENGTH: 20
<212> TYPE: DNA
<213> ORGANISM: brassica napus

<400> SEQUENCE: 746
tacacaagaa acaccttact                                                 20
```

-continued

```
<210> SEQ ID NO 747
<211> LENGTH: 21
<212> TYPE: DNA
<213> ORGANISM: brassica napus

<400> SEQUENCE: 747
tacacaagaa acaccttact t                                          21

<210> SEQ ID NO 748
<211> LENGTH: 22
<212> TYPE: DNA
<213> ORGANISM: brassica napus

<400> SEQUENCE: 748
tacacaagaa acaccttact tt                                         22

<210> SEQ ID NO 749
<211> LENGTH: 23
<212> TYPE: DNA
<213> ORGANISM: brassica napus

<400> SEQUENCE: 749
tacacaagaa acaccttact ttg                                        23

<210> SEQ ID NO 750
<211> LENGTH: 15
<212> TYPE: DNA
<213> ORGANISM: brassica napus

<400> SEQUENCE: 750
acacaagaaa cacct                                                 15

<210> SEQ ID NO 751
<211> LENGTH: 16
<212> TYPE: DNA
<213> ORGANISM: brassica napus

<400> SEQUENCE: 751
acacaagaaa cacctt                                                16

<210> SEQ ID NO 752
<211> LENGTH: 17
<212> TYPE: DNA
<213> ORGANISM: brassica napus

<400> SEQUENCE: 752
acacaagaaa cacctta                                               17

<210> SEQ ID NO 753
<211> LENGTH: 18
<212> TYPE: DNA
<213> ORGANISM: brassica napus

<400> SEQUENCE: 753
acacaagaaa caccttac                                              18

<210> SEQ ID NO 754
<211> LENGTH: 19
<212> TYPE: DNA
<213> ORGANISM: brassica napus

<400> SEQUENCE: 754
```

-continued

```
acacaagaaa caccttact                                          19

<210> SEQ ID NO 755
<211> LENGTH: 20
<212> TYPE: DNA
<213> ORGANISM: brassica napus

<400> SEQUENCE: 755
acacaagaaa caccttactt                                         20

<210> SEQ ID NO 756
<211> LENGTH: 21
<212> TYPE: DNA
<213> ORGANISM: brassica napus

<400> SEQUENCE: 756
acacaagaaa caccttactt t                                       21

<210> SEQ ID NO 757
<211> LENGTH: 22
<212> TYPE: DNA
<213> ORGANISM: brassica napus

<400> SEQUENCE: 757
acacaagaaa caccttactt tg                                      22

<210> SEQ ID NO 758
<211> LENGTH: 23
<212> TYPE: DNA
<213> ORGANISM: brassica napus

<400> SEQUENCE: 758
acacaagaaa caccttactt tgt                                     23

<210> SEQ ID NO 759
<211> LENGTH: 15
<212> TYPE: DNA
<213> ORGANISM: brassica napus

<400> SEQUENCE: 759
cacaagaaac acctt                                              15

<210> SEQ ID NO 760
<211> LENGTH: 16
<212> TYPE: DNA
<213> ORGANISM: brassica napus

<400> SEQUENCE: 760
cacaagaaac acctta                                             16

<210> SEQ ID NO 761
<211> LENGTH: 17
<212> TYPE: DNA
<213> ORGANISM: brassica napus

<400> SEQUENCE: 761
cacaagaaac accttac                                            17

<210> SEQ ID NO 762
<211> LENGTH: 18
<212> TYPE: DNA
<213> ORGANISM: brassica napus

<400> SEQUENCE: 762
```

-continued

```
cacaagaaac accttact                                            18

<210> SEQ ID NO 763
<211> LENGTH: 19
<212> TYPE: DNA
<213> ORGANISM: brassica napus

<400> SEQUENCE: 763
cacaagaaac accttactt                                           19

<210> SEQ ID NO 764
<211> LENGTH: 20
<212> TYPE: DNA
<213> ORGANISM: brassica napus

<400> SEQUENCE: 764
cacaagaaac accttacttt                                          20

<210> SEQ ID NO 765
<211> LENGTH: 21
<212> TYPE: DNA
<213> ORGANISM: brassica napus

<400> SEQUENCE: 765
cacaagaaac accttacttt g                                        21

<210> SEQ ID NO 766
<211> LENGTH: 22
<212> TYPE: DNA
<213> ORGANISM: brassica napus

<400> SEQUENCE: 766
cacaagaaac accttacttt gt                                       22

<210> SEQ ID NO 767
<211> LENGTH: 23
<212> TYPE: DNA
<213> ORGANISM: brassica napus

<400> SEQUENCE: 767
cacaagaaac accttacttt gtt                                      23

<210> SEQ ID NO 768
<211> LENGTH: 15
<212> TYPE: DNA
<213> ORGANISM: brassica napus

<400> SEQUENCE: 768
acaagaaaca cctta                                               15

<210> SEQ ID NO 769
<211> LENGTH: 16
<212> TYPE: DNA
<213> ORGANISM: brassica napus

<400> SEQUENCE: 769
acaagaaaca ccttac                                              16

<210> SEQ ID NO 770
<211> LENGTH: 17
<212> TYPE: DNA
<213> ORGANISM: brassica napus
```

```
<400> SEQUENCE: 770
acaagaaaca ccttact                                              17

<210> SEQ ID NO 771
<211> LENGTH: 18
<212> TYPE: DNA
<213> ORGANISM: brassica napus

<400> SEQUENCE: 771
acaagaaaca ccttactt                                             18

<210> SEQ ID NO 772
<211> LENGTH: 19
<212> TYPE: DNA
<213> ORGANISM: brassica napus

<400> SEQUENCE: 772
acaagaaaca ccttacttt                                            19

<210> SEQ ID NO 773
<211> LENGTH: 20
<212> TYPE: DNA
<213> ORGANISM: brassica napus

<400> SEQUENCE: 773
acaagaaaca ccttactttg                                           20

<210> SEQ ID NO 774
<211> LENGTH: 21
<212> TYPE: DNA
<213> ORGANISM: brassica napus

<400> SEQUENCE: 774
acaagaaaca ccttactttg t                                         21

<210> SEQ ID NO 775
<211> LENGTH: 22
<212> TYPE: DNA
<213> ORGANISM: brassica napus

<400> SEQUENCE: 775
acaagaaaca ccttactttg tt                                        22

<210> SEQ ID NO 776
<211> LENGTH: 23
<212> TYPE: DNA
<213> ORGANISM: brassica napus

<400> SEQUENCE: 776
acaagaaaca ccttactttg tta                                       23

<210> SEQ ID NO 777
<211> LENGTH: 15
<212> TYPE: DNA
<213> ORGANISM: brassica napus

<400> SEQUENCE: 777
caagaaacac cttac                                                15

<210> SEQ ID NO 778
<211> LENGTH: 16
<212> TYPE: DNA
<213> ORGANISM: brassica napus
```

-continued

```
<400> SEQUENCE: 778
caagaaacac cttact                                              16

<210> SEQ ID NO 779
<211> LENGTH: 17
<212> TYPE: DNA
<213> ORGANISM: brassica napus

<400> SEQUENCE: 779
caagaaacac cttactt                                             17

<210> SEQ ID NO 780
<211> LENGTH: 18
<212> TYPE: DNA
<213> ORGANISM: brassica napus

<400> SEQUENCE: 780
caagaaacac cttacttt                                            18

<210> SEQ ID NO 781
<211> LENGTH: 19
<212> TYPE: DNA
<213> ORGANISM: brassica napus

<400> SEQUENCE: 781
caagaaacac cttactttg                                           19

<210> SEQ ID NO 782
<211> LENGTH: 20
<212> TYPE: DNA
<213> ORGANISM: brassica napus

<400> SEQUENCE: 782
caagaaacac cttactttgt                                          20

<210> SEQ ID NO 783
<211> LENGTH: 21
<212> TYPE: DNA
<213> ORGANISM: brassica napus

<400> SEQUENCE: 783
caagaaacac cttactttgt t                                        21

<210> SEQ ID NO 784
<211> LENGTH: 22
<212> TYPE: DNA
<213> ORGANISM: brassica napus

<400> SEQUENCE: 784
caagaaacac cttactttgt ta                                       22

<210> SEQ ID NO 785
<211> LENGTH: 23
<212> TYPE: DNA
<213> ORGANISM: brassica napus

<400> SEQUENCE: 785
caagaaacac cttactttgt taa                                      23

<210> SEQ ID NO 786
<211> LENGTH: 15
<212> TYPE: DNA
```

<213> ORGANISM: brassica napus

<400> SEQUENCE: 786
aagaaacacc ttact                                                    15

<210> SEQ ID NO 787
<211> LENGTH: 16
<212> TYPE: DNA
<213> ORGANISM: brassica napus

<400> SEQUENCE: 787
aagaaacacc ttactt                                                   16

<210> SEQ ID NO 788
<211> LENGTH: 17
<212> TYPE: DNA
<213> ORGANISM: brassica napus

<400> SEQUENCE: 788
aagaaacacc ttacttt                                                  17

<210> SEQ ID NO 789
<211> LENGTH: 18
<212> TYPE: DNA
<213> ORGANISM: brassica napus

<400> SEQUENCE: 789
aagaaacacc ttactttg                                                 18

<210> SEQ ID NO 790
<211> LENGTH: 19
<212> TYPE: DNA
<213> ORGANISM: brassica napus

<400> SEQUENCE: 790
aagaaacacc ttactttgt                                                19

<210> SEQ ID NO 791
<211> LENGTH: 20
<212> TYPE: DNA
<213> ORGANISM: brassica napus

<400> SEQUENCE: 791
aagaaacacc ttactttgtt                                               20

<210> SEQ ID NO 792
<211> LENGTH: 21
<212> TYPE: DNA
<213> ORGANISM: brassica napus

<400> SEQUENCE: 792
aagaaacacc ttactttgtt a                                             21

<210> SEQ ID NO 793
<211> LENGTH: 22
<212> TYPE: DNA
<213> ORGANISM: brassica napus

<400> SEQUENCE: 793
aagaaacacc ttactttgtt aa                                            22

<210> SEQ ID NO 794
<211> LENGTH: 23

-continued

```
<212> TYPE: DNA
<213> ORGANISM: brassica napus

<400> SEQUENCE: 794
aagaaacacc ttactttgtt aaa                                       23

<210> SEQ ID NO 795
<211> LENGTH: 15
<212> TYPE: DNA
<213> ORGANISM: brassica napus

<400> SEQUENCE: 795
tggccttcac gctcc                                                15

<210> SEQ ID NO 796
<211> LENGTH: 16
<212> TYPE: DNA
<213> ORGANISM: brassica napus

<400> SEQUENCE: 796
tggccttcac gctccg                                               16

<210> SEQ ID NO 797
<211> LENGTH: 17
<212> TYPE: DNA
<213> ORGANISM: brassica napus

<400> SEQUENCE: 797
tggccttcac gctccga                                              17

<210> SEQ ID NO 798
<211> LENGTH: 18
<212> TYPE: DNA
<213> ORGANISM: brassica napus

<400> SEQUENCE: 798
tggccttcac gctccgat                                             18

<210> SEQ ID NO 799
<211> LENGTH: 19
<212> TYPE: DNA
<213> ORGANISM: brassica napus

<400> SEQUENCE: 799
tggccttcac gctccgatg                                            19

<210> SEQ ID NO 800
<211> LENGTH: 20
<212> TYPE: DNA
<213> ORGANISM: brassica napus

<400> SEQUENCE: 800
tggccttcac gctccgatgt                                           20

<210> SEQ ID NO 801
<211> LENGTH: 21
<212> TYPE: DNA
<213> ORGANISM: brassica napus

<400> SEQUENCE: 801
tggccttcac gctccgatgt c                                         21

<210> SEQ ID NO 802
```

```
<211> LENGTH: 22
<212> TYPE: DNA
<213> ORGANISM: brassica napus

<400> SEQUENCE: 802
tggccttcac gctccgatgt ct                                              22

<210> SEQ ID NO 803
<211> LENGTH: 23
<212> TYPE: DNA
<213> ORGANISM: brassica napus

<400> SEQUENCE: 803
tggccttcac gctccgatgt ctt                                             23

<210> SEQ ID NO 804
<211> LENGTH: 15
<212> TYPE: DNA
<213> ORGANISM: brassica napus

<400> SEQUENCE: 804
agaaacacct tactt                                                      15

<210> SEQ ID NO 805
<211> LENGTH: 16
<212> TYPE: DNA
<213> ORGANISM: brassica napus

<400> SEQUENCE: 805
agaaacacct tacttt                                                     16

<210> SEQ ID NO 806
<211> LENGTH: 17
<212> TYPE: DNA
<213> ORGANISM: brassica napus

<400> SEQUENCE: 806
agaaacacct tactttg                                                    17

<210> SEQ ID NO 807
<211> LENGTH: 18
<212> TYPE: DNA
<213> ORGANISM: brassica napus

<400> SEQUENCE: 807
agaaacacct tactttgt                                                   18

<210> SEQ ID NO 808
<211> LENGTH: 19
<212> TYPE: DNA
<213> ORGANISM: brassica napus

<400> SEQUENCE: 808
agaaacacct tactttgtt                                                  19

<210> SEQ ID NO 809
<211> LENGTH: 20
<212> TYPE: DNA
<213> ORGANISM: brassica napus

<400> SEQUENCE: 809
agaaacacct tactttgtta                                                 20
```

-continued

```
<210> SEQ ID NO 810
<211> LENGTH: 21
<212> TYPE: DNA
<213> ORGANISM: brassica napus

<400> SEQUENCE: 810
agaaacacct tactttgtta a                                          21

<210> SEQ ID NO 811
<211> LENGTH: 22
<212> TYPE: DNA
<213> ORGANISM: brassica napus

<400> SEQUENCE: 811
agaaacacct tactttgtta aa                                         22

<210> SEQ ID NO 812
<211> LENGTH: 23
<212> TYPE: DNA
<213> ORGANISM: brassica napus

<400> SEQUENCE: 812
agaaacacct tactttgtta aat                                        23

<210> SEQ ID NO 813
<211> LENGTH: 15
<212> TYPE: DNA
<213> ORGANISM: brassica napus

<400> SEQUENCE: 813
gaaacacctt acttt                                                 15

<210> SEQ ID NO 814
<211> LENGTH: 16
<212> TYPE: DNA
<213> ORGANISM: brassica napus

<400> SEQUENCE: 814
gaaacacctt actttg                                                16

<210> SEQ ID NO 815
<211> LENGTH: 17
<212> TYPE: DNA
<213> ORGANISM: brassica napus

<400> SEQUENCE: 815
gaaacacctt actttgt                                               17

<210> SEQ ID NO 816
<211> LENGTH: 18
<212> TYPE: DNA
<213> ORGANISM: brassica napus

<400> SEQUENCE: 816
gaaacacctt actttgtt                                              18

<210> SEQ ID NO 817
<211> LENGTH: 19
<212> TYPE: DNA
<213> ORGANISM: brassica napus

<400> SEQUENCE: 817
gaaacacctt actttgtta                                             19
```

-continued

```
<210> SEQ ID NO 818
<211> LENGTH: 20
<212> TYPE: DNA
<213> ORGANISM: brassica napus

<400> SEQUENCE: 818
gaaacacctt actttgttaa                                                    20

<210> SEQ ID NO 819
<211> LENGTH: 21
<212> TYPE: DNA
<213> ORGANISM: brassica napus

<400> SEQUENCE: 819
gaaacacctt actttgttaa a                                                  21

<210> SEQ ID NO 820
<211> LENGTH: 22
<212> TYPE: DNA
<213> ORGANISM: brassica napus

<400> SEQUENCE: 820
gaaacacctt actttgttaa at                                                 22

<210> SEQ ID NO 821
<211> LENGTH: 23
<212> TYPE: DNA
<213> ORGANISM: brassica napus

<400> SEQUENCE: 821
gaaacacctt actttgttaa att                                                23

<210> SEQ ID NO 822
<211> LENGTH: 15
<212> TYPE: DNA
<213> ORGANISM: brassica napus

<400> SEQUENCE: 822 aaacaccttta ctttg                                                        15

<210> SEQ ID NO 823
<211> LENGTH: 16
<212> TYPE: DNA
<213> ORGANISM: brassica napus

<400> SEQUENCE: 823 aaacaccttta ctttgt                                                       16

<210> SEQ ID NO 824
<211> LENGTH: 17
<212> TYPE: DNA
<213> ORGANISM: brassica napus

<400> SEQUENCE: 824 aaacaccttta ctttgtt                                                      17

<210> SEQ ID NO 825
<211> LENGTH: 18
<212> TYPE: DNA
<213> ORGANISM: brassica napus

<400> SEQUENCE: 825 aaacaccttta ctttgtta                                                     18
```

-continued

<210> SEQ ID NO 826
<211> LENGTH: 19
<212> TYPE: DNA
<213> ORGANISM: brassica napus

<400> SEQUENCE: 826
aaacacctta ctttgttaa                                                    19

<210> SEQ ID NO 827
<211> LENGTH: 20
<212> TYPE: DNA
<213> ORGANISM: brassica napus

<400> SEQUENCE: 827
aaacacctta ctttgttaaa                                                   20

<210> SEQ ID NO 828
<211> LENGTH: 21
<212> TYPE: DNA
<213> ORGANISM: brassica napus

<400> SEQUENCE: 828
aaacacctta ctttgttaaa t                                                 21

<210> SEQ ID NO 829
<211> LENGTH: 22
<212> TYPE: DNA
<213> ORGANISM: brassica napus

<400> SEQUENCE: 829
aaacacctta ctttgttaaa tt                                                22

<210> SEQ ID NO 830
<211> LENGTH: 23
<212> TYPE: DNA
<213> ORGANISM: brassica napus

<400> SEQUENCE: 830
aaacacctta ctttgttaaa ttt                                               23

<210> SEQ ID NO 831
<211> LENGTH: 15
<212> TYPE: DNA
<213> ORGANISM: brassica napus

<400> SEQUENCE: 831
aacaccttac tttgt                                                        15

<210> SEQ ID NO 832
<211> LENGTH: 16
<212> TYPE: DNA
<213> ORGANISM: brassica napus

<400> SEQUENCE: 832
aacaccttac tttgtt                                                       16

<210> SEQ ID NO 833
<211> LENGTH: 17
<212> TYPE: DNA
<213> ORGANISM: brassica napus

<400> SEQUENCE: 833

-continued

```
aacaccttac tttgtta                                           17

<210> SEQ ID NO 834
<211> LENGTH: 18
<212> TYPE: DNA
<213> ORGANISM: brassica napus

<400> SEQUENCE: 834
aacaccttac tttgttaa                                          18

<210> SEQ ID NO 835
<211> LENGTH: 19
<212> TYPE: DNA
<213> ORGANISM: brassica napus

<400> SEQUENCE: 835
aacaccttac tttgttaaa                                         19

<210> SEQ ID NO 836
<211> LENGTH: 20
<212> TYPE: DNA
<213> ORGANISM: brassica napus

<400> SEQUENCE: 836
aacaccttac tttgttaaat                                        20

<210> SEQ ID NO 837
<211> LENGTH: 21
<212> TYPE: DNA
<213> ORGANISM: brassica napus

<400> SEQUENCE: 837
aacaccttac tttgttaaat t                                      21

<210> SEQ ID NO 838
<211> LENGTH: 22
<212> TYPE: DNA
<213> ORGANISM: brassica napus

<400> SEQUENCE: 838
aacaccttac tttgttaaat tt                                     22

<210> SEQ ID NO 839
<211> LENGTH: 23
<212> TYPE: DNA
<213> ORGANISM: brassica napus

<400> SEQUENCE: 839
aacaccttac tttgttaaat tta                                    23

<210> SEQ ID NO 840
<211> LENGTH: 15
<212> TYPE: DNA
<213> ORGANISM: brassica napus

<400> SEQUENCE: 840
acaccttact ttgtt                                             15

<210> SEQ ID NO 841
<211> LENGTH: 16
<212> TYPE: DNA
<213> ORGANISM: brassica napus

<400> SEQUENCE: 841
```

-continued

```
acaccttact ttgtta                                                  16

<210> SEQ ID NO 842
<211> LENGTH: 17
<212> TYPE: DNA
<213> ORGANISM: brassica napus

<400> SEQUENCE: 842
acaccttact ttgttaa                                                 17

<210> SEQ ID NO 843
<211> LENGTH: 18
<212> TYPE: DNA
<213> ORGANISM: brassica napus

<400> SEQUENCE: 843
acaccttact ttgttaaa                                                18

<210> SEQ ID NO 844
<211> LENGTH: 19
<212> TYPE: DNA
<213> ORGANISM: brassica napus

<400> SEQUENCE: 844
acaccttact ttgttaaat                                               19

<210> SEQ ID NO 845
<211> LENGTH: 20
<212> TYPE: DNA
<213> ORGANISM: brassica napus

<400> SEQUENCE: 845
acaccttact ttgttaaatt                                              20

<210> SEQ ID NO 846
<211> LENGTH: 21
<212> TYPE: DNA
<213> ORGANISM: brassica napus

<400> SEQUENCE: 846
acaccttact ttgttaaatt t                                            21

<210> SEQ ID NO 847
<211> LENGTH: 22
<212> TYPE: DNA
<213> ORGANISM: brassica napus

<400> SEQUENCE: 847
acaccttact ttgttaaatt ta                                           22

<210> SEQ ID NO 848
<211> LENGTH: 23
<212> TYPE: DNA
<213> ORGANISM: brassica napus

<400> SEQUENCE: 848
acaccttact ttgttaaatt taa                                          23

<210> SEQ ID NO 849
<211> LENGTH: 15
<212> TYPE: DNA
<213> ORGANISM: brassica napus
```

-continued

```
<400> SEQUENCE: 849
caccttactt tgtta                                              15

<210> SEQ ID NO 850
<211> LENGTH: 16
<212> TYPE: DNA
<213> ORGANISM: brassica napus

<400> SEQUENCE: 850
caccttactt tgttaa                                             16

<210> SEQ ID NO 851
<211> LENGTH: 17
<212> TYPE: DNA
<213> ORGANISM: brassica napus

<400> SEQUENCE: 851
caccttactt tgttaaa                                            17

<210> SEQ ID NO 852
<211> LENGTH: 18
<212> TYPE: DNA
<213> ORGANISM: brassica napus

<400> SEQUENCE: 852
caccttactt tgttaaat                                           18

<210> SEQ ID NO 853
<211> LENGTH: 19
<212> TYPE: DNA
<213> ORGANISM: brassica napus

<400> SEQUENCE: 853
caccttactt tgttaaatt                                          19

<210> SEQ ID NO 854
<211> LENGTH: 20
<212> TYPE: DNA
<213> ORGANISM: brassica napus

<400> SEQUENCE: 854
caccttactt tgttaaattt                                         20

<210> SEQ ID NO 855
<211> LENGTH: 21
<212> TYPE: DNA
<213> ORGANISM: brassica napus

<400> SEQUENCE: 855
caccttactt tgttaaattt a                                       21

<210> SEQ ID NO 856
<211> LENGTH: 22
<212> TYPE: DNA
<213> ORGANISM: brassica napus

<400> SEQUENCE: 856
caccttactt tgttaaattt aa                                      22

<210> SEQ ID NO 857
<211> LENGTH: 23
<212> TYPE: DNA
<213> ORGANISM: brassica napus
```

-continued

```
<400> SEQUENCE: 857
caccttactt tgttaaattt aaa                                        23

<210> SEQ ID NO 858
<211> LENGTH: 15
<212> TYPE: DNA
<213> ORGANISM: brassica napus

<400> SEQUENCE: 858
accttacttt gttaa                                                 15

<210> SEQ ID NO 859
<211> LENGTH: 16
<212> TYPE: DNA
<213> ORGANISM: brassica napus

<400> SEQUENCE: 859
accttacttt gttaaa                                                16

<210> SEQ ID NO 860
<211> LENGTH: 17
<212> TYPE: DNA
<213> ORGANISM: brassica napus

<400> SEQUENCE: 860
accttacttt gttaaat                                               17

<210> SEQ ID NO 861
<211> LENGTH: 18
<212> TYPE: DNA
<213> ORGANISM: brassica napus

<400> SEQUENCE: 861
accttacttt gttaaatt                                              18

<210> SEQ ID NO 862
<211> LENGTH: 19
<212> TYPE: DNA
<213> ORGANISM: brassica napus

<400> SEQUENCE: 862
accttacttt gttaaattt                                             19

<210> SEQ ID NO 863
<211> LENGTH: 20
<212> TYPE: DNA
<213> ORGANISM: brassica napus

<400> SEQUENCE: 863
accttacttt gttaaattta                                            20

<210> SEQ ID NO 864
<211> LENGTH: 21
<212> TYPE: DNA
<213> ORGANISM: brassica napus

<400> SEQUENCE: 864
accttacttt gttaaattta a                                          21

<210> SEQ ID NO 865
<211> LENGTH: 22
<212> TYPE: DNA
```

-continued

<213> ORGANISM: brassica napus

<400> SEQUENCE: 865
accttacttt gttaaattta aa                                          22

<210> SEQ ID NO 866
<211> LENGTH: 23
<212> TYPE: DNA
<213> ORGANISM: brassica napus

<400> SEQUENCE: 866
accttacttt gttaaattta aaa                                         23

<210> SEQ ID NO 867
<211> LENGTH: 15
<212> TYPE: DNA
<213> ORGANISM: brassica napus

<400> SEQUENCE: 867
ccttactttg ttaaa                                                  15

<210> SEQ ID NO 868
<211> LENGTH: 16
<212> TYPE: DNA
<213> ORGANISM: brassica napus

<400> SEQUENCE: 868
ccttactttg ttaaat                                                 16

<210> SEQ ID NO 869
<211> LENGTH: 17
<212> TYPE: DNA
<213> ORGANISM: brassica napus

<400> SEQUENCE: 869
ccttactttg ttaaatt                                                17

<210> SEQ ID NO 870
<211> LENGTH: 18
<212> TYPE: DNA
<213> ORGANISM: brassica napus

<400> SEQUENCE: 870
ccttactttg ttaaattt                                               18

<210> SEQ ID NO 871
<211> LENGTH: 19
<212> TYPE: DNA
<213> ORGANISM: brassica napus

<400> SEQUENCE: 871
ccttactttg ttaaattta                                              19

<210> SEQ ID NO 872
<211> LENGTH: 20
<212> TYPE: DNA
<213> ORGANISM: brassica napus

<400> SEQUENCE: 872
ccttactttg ttaaatttaa                                             20

<210> SEQ ID NO 873
<211> LENGTH: 21

-continued

```
<212> TYPE: DNA
<213> ORGANISM: brassica napus

<400> SEQUENCE: 873
ccttactttg ttaaatttaa a                                              21

<210> SEQ ID NO 874
<211> LENGTH: 22
<212> TYPE: DNA
<213> ORGANISM: brassica napus

<400> SEQUENCE: 874
ccttactttg ttaaatttaa aa                                             22

<210> SEQ ID NO 875
<211> LENGTH: 23
<212> TYPE: DNA
<213> ORGANISM: brassica napus

<400> SEQUENCE: 875
ccttactttg ttaaatttaa aat                                            23

<210> SEQ ID NO 876
<211> LENGTH: 15
<212> TYPE: DNA
<213> ORGANISM: brassica napus

<400> SEQUENCE: 876
cttactttgt taaat                                                     15

<210> SEQ ID NO 877
<211> LENGTH: 16
<212> TYPE: DNA
<213> ORGANISM: brassica napus

<400> SEQUENCE: 877
cttactttgt taaatt                                                    16

<210> SEQ ID NO 878
<211> LENGTH: 17
<212> TYPE: DNA
<213> ORGANISM: brassica napus

<400> SEQUENCE: 878
cttactttgt taaattt                                                   17

<210> SEQ ID NO 879
<211> LENGTH: 18
<212> TYPE: DNA
<213> ORGANISM: brassica napus

<400> SEQUENCE: 879
cttactttgt taaattta                                                  18

<210> SEQ ID NO 880
<211> LENGTH: 19
<212> TYPE: DNA
<213> ORGANISM: brassica napus

<400> SEQUENCE: 880
cttactttgt taaatttaa                                                 19

<210> SEQ ID NO 881
```

<211> LENGTH: 20
<212> TYPE: DNA
<213> ORGANISM: brassica napus

<400> SEQUENCE: 881
cttactttgt taaatttaaa                                                      20

<210> SEQ ID NO 882
<211> LENGTH: 21
<212> TYPE: DNA
<213> ORGANISM: brassica napus

<400> SEQUENCE: 882
cttactttgt taaatttaaa a                                                    21

<210> SEQ ID NO 883
<211> LENGTH: 22
<212> TYPE: DNA
<213> ORGANISM: brassica napus

<400> SEQUENCE: 883
cttactttgt taaatttaaa at                                                   22

<210> SEQ ID NO 884
<211> LENGTH: 23
<212> TYPE: DNA
<213> ORGANISM: brassica napus

<400> SEQUENCE: 884
cttactttgt taaatttaaa ata                                                  23

<210> SEQ ID NO 885
<211> LENGTH: 15
<212> TYPE: DNA
<213> ORGANISM: brassica napus

<400> SEQUENCE: 885
ttactttgtt aaatt                                                          15

<210> SEQ ID NO 886
<211> LENGTH: 16
<212> TYPE: DNA
<213> ORGANISM: brassica napus

<400> SEQUENCE: 886
ttactttgtt aaattt                                                         16

<210> SEQ ID NO 887
<211> LENGTH: 17
<212> TYPE: DNA
<213> ORGANISM: brassica napus

<400> SEQUENCE: 887
ttactttgtt aaattta                                                        17

<210> SEQ ID NO 888
<211> LENGTH: 18
<212> TYPE: DNA
<213> ORGANISM: brassica napus

<400> SEQUENCE: 888
ttactttgtt aaatttaa                                                       18

-continued

```
<210> SEQ ID NO 889
<211> LENGTH: 19
<212> TYPE: DNA
<213> ORGANISM: brassica napus

<400> SEQUENCE: 889
ttactttgtt aaatttaaa                                                              19

<210> SEQ ID NO 890
<211> LENGTH: 20
<212> TYPE: DNA
<213> ORGANISM: brassica napus

<400> SEQUENCE: 890
ttactttgtt aaatttaaaa                                                             20

<210> SEQ ID NO 891
<211> LENGTH: 21
<212> TYPE: DNA
<213> ORGANISM: brassica napus

<400> SEQUENCE: 891
ttactttgtt aaatttaaaa t                                                           21

<210> SEQ ID NO 892
<211> LENGTH: 22
<212> TYPE: DNA
<213> ORGANISM: brassica napus

<400> SEQUENCE: 892
ttactttgtt aaatttaaaa ta                                                          22

<210> SEQ ID NO 893
<211> LENGTH: 23
<212> TYPE: DNA
<213> ORGANISM: brassica napus

<400> SEQUENCE: 893
ttactttgtt aaatttaaaa tag                                                         23

<210> SEQ ID NO 894
<211> LENGTH: 15
<212> TYPE: DNA
<213> ORGANISM: brassica napus

<400> SEQUENCE: 894
ggccttcacg ctccg                                                                  15

<210> SEQ ID NO 895
<211> LENGTH: 16
<212> TYPE: DNA
<213> ORGANISM: brassica napus

<400> SEQUENCE: 895
ggccttcacg ctccga                                                                 16

<210> SEQ ID NO 896
<211> LENGTH: 17
<212> TYPE: DNA
<213> ORGANISM: brassica napus

<400> SEQUENCE: 896
ggccttcacg ctccgat                                                                17
```

-continued

```
<210> SEQ ID NO 897
<211> LENGTH: 18
<212> TYPE: DNA
<213> ORGANISM: brassica napus

<400> SEQUENCE: 897
ggccttcacg ctccgatg                                             18

<210> SEQ ID NO 898
<211> LENGTH: 19
<212> TYPE: DNA
<213> ORGANISM: brassica napus

<400> SEQUENCE: 898
ggccttcacg ctccgatgt                                            19

<210> SEQ ID NO 899
<211> LENGTH: 20
<212> TYPE: DNA
<213> ORGANISM: brassica napus

<400> SEQUENCE: 899
ggccttcacg ctccgatgtc                                           20

<210> SEQ ID NO 900
<211> LENGTH: 21
<212> TYPE: DNA
<213> ORGANISM: brassica napus

<400> SEQUENCE: 900
ggccttcacg ctccgatgtc t                                         21

<210> SEQ ID NO 901
<211> LENGTH: 22
<212> TYPE: DNA
<213> ORGANISM: brassica napus

<400> SEQUENCE: 901
ggccttcacg ctccgatgtc tt                                        22

<210> SEQ ID NO 902
<211> LENGTH: 23
<212> TYPE: DNA
<213> ORGANISM: brassica napus

<400> SEQUENCE: 902
ggccttcacg ctccgatgtc ttc                                       23

<210> SEQ ID NO 903
<211> LENGTH: 15
<212> TYPE: DNA
<213> ORGANISM: brassica napus

<400> SEQUENCE: 903
gccttcacgc tccga                                                15

<210> SEQ ID NO 904
<211> LENGTH: 16
<212> TYPE: DNA
<213> ORGANISM: brassica napus

<400> SEQUENCE: 904
gccttcacgc tccgat                                               16
```

-continued

```
<210> SEQ ID NO 905
<211> LENGTH: 17
<212> TYPE: DNA
<213> ORGANISM: brassica napus

<400> SEQUENCE: 905
gccttcacgc tccgatg                                              17

<210> SEQ ID NO 906
<211> LENGTH: 18
<212> TYPE: DNA
<213> ORGANISM: brassica napus

<400> SEQUENCE: 906
gccttcacgc tccgatgt                                             18

<210> SEQ ID NO 907
<211> LENGTH: 19
<212> TYPE: DNA
<213> ORGANISM: brassica napus

<400> SEQUENCE: 907
gccttcacgc tccgatgtc                                            19

<210> SEQ ID NO 908
<211> LENGTH: 20
<212> TYPE: DNA
<213> ORGANISM: brassica napus

<400> SEQUENCE: 908
gccttcacgc tccgatgtct                                           20

<210> SEQ ID NO 909
<211> LENGTH: 21
<212> TYPE: DNA
<213> ORGANISM: brassica napus

<400> SEQUENCE: 909
gccttcacgc tccgatgtct t                                         21

<210> SEQ ID NO 910
<211> LENGTH: 22
<212> TYPE: DNA
<213> ORGANISM: brassica napus

<400> SEQUENCE: 910
gccttcacgc tccgatgtct tc                                        22

<210> SEQ ID NO 911
<211> LENGTH: 23
<212> TYPE: DNA
<213> ORGANISM: brassica napus

<400> SEQUENCE: 911
gccttcacgc tccgatgtct tct                                       23

<210> SEQ ID NO 912
<211> LENGTH: 15
<212> TYPE: DNA
<213> ORGANISM: brassica napus

<400> SEQUENCE: 912
```

-continued

```
ccttcacgct ccgat                                                    15

<210> SEQ ID NO 913
<211> LENGTH: 16
<212> TYPE: DNA
<213> ORGANISM: brassica napus

<400> SEQUENCE: 913
ccttcacgct ccgatg                                                   16

<210> SEQ ID NO 914
<211> LENGTH: 17
<212> TYPE: DNA
<213> ORGANISM: brassica napus

<400> SEQUENCE: 914
ccttcacgct ccgatgt                                                  17

<210> SEQ ID NO 915
<211> LENGTH: 18
<212> TYPE: DNA
<213> ORGANISM: brassica napus

<400> SEQUENCE: 915
ccttcacgct ccgatgtc                                                 18

<210> SEQ ID NO 916
<211> LENGTH: 19
<212> TYPE: DNA
<213> ORGANISM: brassica napus

<400> SEQUENCE: 916
ccttcacgct ccgatgtct                                                19

<210> SEQ ID NO 917
<211> LENGTH: 20
<212> TYPE: DNA
<213> ORGANISM: brassica napus

<400> SEQUENCE: 917
ccttcacgct ccgatgtctt                                               20

<210> SEQ ID NO 918
<211> LENGTH: 21
<212> TYPE: DNA
<213> ORGANISM: brassica napus

<400> SEQUENCE: 918
ccttcacgct ccgatgtctt c                                             21

<210> SEQ ID NO 919
<211> LENGTH: 22
<212> TYPE: DNA
<213> ORGANISM: brassica napus

<400> SEQUENCE: 919
ccttcacgct ccgatgtctt ct                                            22

<210> SEQ ID NO 920
<211> LENGTH: 23
<212> TYPE: DNA
<213> ORGANISM: brassica napus

<400> SEQUENCE: 920
```

-continued

```
ccttcacgct ccgatgtctt ctg                                    23

<210> SEQ ID NO 921
<211> LENGTH: 15
<212> TYPE: DNA
<213> ORGANISM: brassica napus

<400> SEQUENCE: 921
cttcacgctc cgatg                                             15

<210> SEQ ID NO 922
<211> LENGTH: 16
<212> TYPE: DNA
<213> ORGANISM: brassica napus

<400> SEQUENCE: 922
cttcacgctc cgatgt                                            16

<210> SEQ ID NO 923
<211> LENGTH: 17
<212> TYPE: DNA
<213> ORGANISM: brassica napus

<400> SEQUENCE: 923
cttcacgctc cgatgtc                                           17

<210> SEQ ID NO 924
<211> LENGTH: 18
<212> TYPE: DNA
<213> ORGANISM: brassica napus

<400> SEQUENCE: 924
cttcacgctc cgatgtct                                          18

<210> SEQ ID NO 925
<211> LENGTH: 19
<212> TYPE: DNA
<213> ORGANISM: brassica napus

<400> SEQUENCE: 925
cttcacgctc cgatgtctt                                         19

<210> SEQ ID NO 926
<211> LENGTH: 20
<212> TYPE: DNA
<213> ORGANISM: brassica napus

<400> SEQUENCE: 926
cttcacgctc cgatgtcttc                                        20

<210> SEQ ID NO 927
<211> LENGTH: 21
<212> TYPE: DNA
<213> ORGANISM: brassica napus

<400> SEQUENCE: 927
cttcacgctc cgatgtcttc t                                      21

<210> SEQ ID NO 928
<211> LENGTH: 22
<212> TYPE: DNA
<213> ORGANISM: brassica napus
```

-continued

```
<400> SEQUENCE: 928
cttcacgctc cgatgtcttc tg                                          22

<210> SEQ ID NO 929
<211> LENGTH: 23
<212> TYPE: DNA
<213> ORGANISM: brassica napus

<400> SEQUENCE: 929
cttcacgctc cgatgtcttc tgt                                         23

<210> SEQ ID NO 930
<211> LENGTH: 15
<212> TYPE: DNA
<213> ORGANISM: brassica napus

<400> SEQUENCE: 930
ttcacgctcc gatgt                                                  15

<210> SEQ ID NO 931
<211> LENGTH: 16
<212> TYPE: DNA
<213> ORGANISM: brassica napus

<400> SEQUENCE: 931
ttcacgctcc gatgtc                                                 16

<210> SEQ ID NO 932
<211> LENGTH: 17
<212> TYPE: DNA
<213> ORGANISM: brassica napus

<400> SEQUENCE: 932
ttcacgctcc gatgtct                                                17

<210> SEQ ID NO 933
<211> LENGTH: 18
<212> TYPE: DNA
<213> ORGANISM: brassica napus

<400> SEQUENCE: 933
ttcacgctcc gatgtctt                                               18

<210> SEQ ID NO 934
<211> LENGTH: 19
<212> TYPE: DNA
<213> ORGANISM: brassica napus

<400> SEQUENCE: 934
ttcacgctcc gatgtcttc                                              19

<210> SEQ ID NO 935
<211> LENGTH: 20
<212> TYPE: DNA
<213> ORGANISM: brassica napus

<400> SEQUENCE: 935
ttcacgctcc gatgtcttct                                             20

<210> SEQ ID NO 936
<211> LENGTH: 21
<212> TYPE: DNA
<213> ORGANISM: brassica napus
```

<400> SEQUENCE: 936
ttcacgctcc gatgtcttct g                                              21

<210> SEQ ID NO 937
<211> LENGTH: 22
<212> TYPE: DNA
<213> ORGANISM: brassica napus

<400> SEQUENCE: 937
ttcacgctcc gatgtcttct gt                                             22

<210> SEQ ID NO 938
<211> LENGTH: 23
<212> TYPE: DNA
<213> ORGANISM: brassica napus

<400> SEQUENCE: 938
ttcacgctcc gatgtcttct gtg                                            23

<210> SEQ ID NO 939
<211> LENGTH: 15
<212> TYPE: DNA
<213> ORGANISM: brassica napus

<400> SEQUENCE: 939
tcacgctccg atgtc                                                     15

<210> SEQ ID NO 940
<211> LENGTH: 16
<212> TYPE: DNA
<213> ORGANISM: brassica napus

<400> SEQUENCE: 940
tcacgctccg atgtct                                                    16

<210> SEQ ID NO 941
<211> LENGTH: 17
<212> TYPE: DNA
<213> ORGANISM: brassica napus

<400> SEQUENCE: 941
tcacgctccg atgtctt                                                   17

<210> SEQ ID NO 942
<211> LENGTH: 18
<212> TYPE: DNA
<213> ORGANISM: brassica napus

<400> SEQUENCE: 942
tcacgctccg atgtcttc                                                  18

<210> SEQ ID NO 943
<211> LENGTH: 19
<212> TYPE: DNA
<213> ORGANISM: brassica napus

<400> SEQUENCE: 943
tcacgctccg atgtcttct                                                 19

<210> SEQ ID NO 944
<211> LENGTH: 20
<212> TYPE: DNA

-continued

<213> ORGANISM: brassica napus

<400> SEQUENCE: 944
tcacgctccg atgtcttctg                                                    20

<210> SEQ ID NO 945
<211> LENGTH: 21
<212> TYPE: DNA
<213> ORGANISM: brassica napus

<400> SEQUENCE: 945
tcacgctccg atgtcttctg t                                                  21

<210> SEQ ID NO 946
<211> LENGTH: 22
<212> TYPE: DNA
<213> ORGANISM: brassica napus

<400> SEQUENCE: 946
tcacgctccg atgtcttctg tg                                                 22

<210> SEQ ID NO 947
<211> LENGTH: 23
<212> TYPE: DNA
<213> ORGANISM: brassica napus

<400> SEQUENCE: 947
tcacgctccg atgtcttctg tgt                                                23

<210> SEQ ID NO 948
<211> LENGTH: 15
<212> TYPE: DNA
<213> ORGANISM: brassica napus

<400> SEQUENCE: 948
tttaactata gtggc                                                         15

<210> SEQ ID NO 949
<211> LENGTH: 16
<212> TYPE: DNA
<213> ORGANISM: brassica napus

<400> SEQUENCE: 949
tttaactata gtggcc                                                        16

<210> SEQ ID NO 950
<211> LENGTH: 17
<212> TYPE: DNA
<213> ORGANISM: brassica napus

<400> SEQUENCE: 950
tttaactata gtggcct                                                       17

<210> SEQ ID NO 951
<211> LENGTH: 18
<212> TYPE: DNA
<213> ORGANISM: brassica napus

<400> SEQUENCE: 951
tttaactata gtggcctt                                                      18

<210> SEQ ID NO 952
<211> LENGTH: 19

-continued

```
<212> TYPE: DNA
<213> ORGANISM: brassica napus

<400> SEQUENCE: 952
tttaactata gtggccttc                                              19

<210> SEQ ID NO 953
<211> LENGTH: 20
<212> TYPE: DNA
<213> ORGANISM: brassica napus

<400> SEQUENCE: 953
tttaactata gtggccttca                                             20

<210> SEQ ID NO 954
<211> LENGTH: 21
<212> TYPE: DNA
<213> ORGANISM: brassica napus

<400> SEQUENCE: 954
tttaactata gtggccttca c                                           21

<210> SEQ ID NO 955
<211> LENGTH: 22
<212> TYPE: DNA
<213> ORGANISM: brassica napus

<400> SEQUENCE: 955
tttaactata gtggccttca cg                                          22

<210> SEQ ID NO 956
<211> LENGTH: 23
<212> TYPE: DNA
<213> ORGANISM: brassica napus

<400> SEQUENCE: 956
tttaactata gtggccttca cgc                                         23

<210> SEQ ID NO 957
<211> LENGTH: 15
<212> TYPE: DNA
<213> ORGANISM: brassica napus

<400> SEQUENCE: 957
cacgctccga tgtct                                                  15

<210> SEQ ID NO 958
<211> LENGTH: 16
<212> TYPE: DNA
<213> ORGANISM: brassica napus

<400> SEQUENCE: 958
cacgctccga tgtctt                                                 16

<210> SEQ ID NO 959
<211> LENGTH: 17
<212> TYPE: DNA
<213> ORGANISM: brassica napus

<400> SEQUENCE: 959
cacgctccga tgtcttc                                                17

<210> SEQ ID NO 960
```

```
<211> LENGTH: 18
<212> TYPE: DNA
<213> ORGANISM: brassica napus

<400> SEQUENCE: 960
cacgctccga tgtcttct                                                      18

<210> SEQ ID NO 961
<211> LENGTH: 19
<212> TYPE: DNA
<213> ORGANISM: brassica napus

<400> SEQUENCE: 961
cacgctccga tgtcttctg                                                     19

<210> SEQ ID NO 962
<211> LENGTH: 20
<212> TYPE: DNA
<213> ORGANISM: brassica napus

<400> SEQUENCE: 962
cacgctccga tgtcttctgt                                                    20

<210> SEQ ID NO 963
<211> LENGTH: 21
<212> TYPE: DNA
<213> ORGANISM: brassica napus

<400> SEQUENCE: 963
cacgctccga tgtcttctgt g                                                  21

<210> SEQ ID NO 964
<211> LENGTH: 22
<212> TYPE: DNA
<213> ORGANISM: brassica napus

<400> SEQUENCE: 964
cacgctccga tgtcttctgt gt                                                 22

<210> SEQ ID NO 965
<211> LENGTH: 23
<212> TYPE: DNA
<213> ORGANISM: brassica napus

<400> SEQUENCE: 965
cacgctccga tgtcttctgt gtg                                                23

<210> SEQ ID NO 966
<211> LENGTH: 15
<212> TYPE: DNA
<213> ORGANISM: brassica napus

<400> SEQUENCE: 966
acgctccgat gtctt                                                         15

<210> SEQ ID NO 967
<211> LENGTH: 16
<212> TYPE: DNA
<213> ORGANISM: brassica napus

<400> SEQUENCE: 967
acgctccgat gtcttc                                                        16
```

-continued

```
<210> SEQ ID NO 968
<211> LENGTH: 17
<212> TYPE: DNA
<213> ORGANISM: brassica napus

<400> SEQUENCE: 968
acgctccgat gtcttct                                              17

<210> SEQ ID NO 969
<211> LENGTH: 18
<212> TYPE: DNA
<213> ORGANISM: brassica napus

<400> SEQUENCE: 969
acgctccgat gtcttctg                                             18

<210> SEQ ID NO 970
<211> LENGTH: 19
<212> TYPE: DNA
<213> ORGANISM: brassica napus

<400> SEQUENCE: 970
acgctccgat gtcttctgt                                            19

<210> SEQ ID NO 971
<211> LENGTH: 20
<212> TYPE: DNA
<213> ORGANISM: brassica napus

<400> SEQUENCE: 971
acgctccgat gtcttctgtg                                           20

<210> SEQ ID NO 972
<211> LENGTH: 21
<212> TYPE: DNA
<213> ORGANISM: brassica napus

<400> SEQUENCE: 972
acgctccgat gtcttctgtg t                                         21

<210> SEQ ID NO 973
<211> LENGTH: 22
<212> TYPE: DNA
<213> ORGANISM: brassica napus

<400> SEQUENCE: 973
acgctccgat gtcttctgtg tg                                        22

<210> SEQ ID NO 974
<211> LENGTH: 23
<212> TYPE: DNA
<213> ORGANISM: brassica napus

<400> SEQUENCE: 974
acgctccgat gtcttctgtg tgg                                       23

<210> SEQ ID NO 975
<211> LENGTH: 15
<212> TYPE: DNA
<213> ORGANISM: brassica napus

<400> SEQUENCE: 975
cgctccgatg tcttc                                                15
```

-continued

```
<210> SEQ ID NO 976
<211> LENGTH: 16
<212> TYPE: DNA
<213> ORGANISM: brassica napus

<400> SEQUENCE: 976
cgctccgatg tcttct                                              16

<210> SEQ ID NO 977
<211> LENGTH: 17
<212> TYPE: DNA
<213> ORGANISM: brassica napus

<400> SEQUENCE: 977
cgctccgatg tcttctg                                             17

<210> SEQ ID NO 978
<211> LENGTH: 18
<212> TYPE: DNA
<213> ORGANISM: brassica napus

<400> SEQUENCE: 978
cgctccgatg tcttctgt                                            18

<210> SEQ ID NO 979
<211> LENGTH: 19
<212> TYPE: DNA
<213> ORGANISM: brassica napus

<400> SEQUENCE: 979
cgctccgatg tcttctgtg                                           19

<210> SEQ ID NO 980
<211> LENGTH: 20
<212> TYPE: DNA
<213> ORGANISM: brassica napus

<400> SEQUENCE: 980
cgctccgatg tcttctgtgt                                          20

<210> SEQ ID NO 981
<211> LENGTH: 21
<212> TYPE: DNA
<213> ORGANISM: brassica napus

<400> SEQUENCE: 981
cgctccgatg tcttctgtgt g                                        21

<210> SEQ ID NO 982
<211> LENGTH: 22
<212> TYPE: DNA
<213> ORGANISM: brassica napus

<400> SEQUENCE: 982
cgctccgatg tcttctgtgt gg                                       22

<210> SEQ ID NO 983
<211> LENGTH: 23
<212> TYPE: DNA
<213> ORGANISM: brassica napus

<400> SEQUENCE: 983
cgctccgatg tcttctgtgt ggg                                      23
```

```
<210> SEQ ID NO 984
<211> LENGTH: 15
<212> TYPE: DNA
<213> ORGANISM: brassica napus

<400> SEQUENCE: 984
gctccgatgt cttct                                                    15

<210> SEQ ID NO 985
<211> LENGTH: 16
<212> TYPE: DNA
<213> ORGANISM: brassica napus

<400> SEQUENCE: 985
gctccgatgt cttctg                                                   16

<210> SEQ ID NO 986
<211> LENGTH: 17
<212> TYPE: DNA
<213> ORGANISM: brassica napus

<400> SEQUENCE: 986
gctccgatgt cttctgt                                                  17

<210> SEQ ID NO 987
<211> LENGTH: 18
<212> TYPE: DNA
<213> ORGANISM: brassica napus

<400> SEQUENCE: 987
gctccgatgt cttctgtg                                                 18

<210> SEQ ID NO 988
<211> LENGTH: 19
<212> TYPE: DNA
<213> ORGANISM: brassica napus

<400> SEQUENCE: 988
gctccgatgt cttctgtgt                                                19

<210> SEQ ID NO 989
<211> LENGTH: 20
<212> TYPE: DNA
<213> ORGANISM: brassica napus

<400> SEQUENCE: 989
gctccgatgt cttctgtgtg                                               20

<210> SEQ ID NO 990
<211> LENGTH: 21
<212> TYPE: DNA
<213> ORGANISM: brassica napus

<400> SEQUENCE: 990
gctccgatgt cttctgtgtg g                                             21

<210> SEQ ID NO 991
<211> LENGTH: 22
<212> TYPE: DNA
<213> ORGANISM: brassica napus

<400> SEQUENCE: 991
```

-continued

```
gctccgatgt cttctgtgtg gg                                        22

<210> SEQ ID NO 992
<211> LENGTH: 23
<212> TYPE: DNA
<213> ORGANISM: brassica napus

<400> SEQUENCE: 992
gctccgatgt cttctgtgtg ggc                                       23

<210> SEQ ID NO 993
<211> LENGTH: 15
<212> TYPE: DNA
<213> ORGANISM: brassica napus

<400> SEQUENCE: 993
ctccgatgtc ttctg                                                15

<210> SEQ ID NO 994
<211> LENGTH: 16
<212> TYPE: DNA
<213> ORGANISM: brassica napus

<400> SEQUENCE: 994
ctccgatgtc ttctgt                                               16

<210> SEQ ID NO 995
<211> LENGTH: 17
<212> TYPE: DNA
<213> ORGANISM: brassica napus

<400> SEQUENCE: 995
ctccgatgtc ttctgtg                                              17

<210> SEQ ID NO 996
<211> LENGTH: 18
<212> TYPE: DNA
<213> ORGANISM: brassica napus

<400> SEQUENCE: 996
ctccgatgtc ttctgtgt                                             18

<210> SEQ ID NO 997
<211> LENGTH: 19
<212> TYPE: DNA
<213> ORGANISM: brassica napus

<400> SEQUENCE: 997
ctccgatgtc ttctgtgtg                                            19

<210> SEQ ID NO 998
<211> LENGTH: 20
<212> TYPE: DNA
<213> ORGANISM: brassica napus

<400> SEQUENCE: 998
ctccgatgtc ttctgtgtgg                                           20

<210> SEQ ID NO 999
<211> LENGTH: 21
<212> TYPE: DNA
<213> ORGANISM: brassica napus

<400> SEQUENCE: 999
```

-continued

```
ctccgatgtc ttctgtgtgg g                                          21

<210> SEQ ID NO 1000
<211> LENGTH: 22
<212> TYPE: DNA
<213> ORGANISM: brassica napus

<400> SEQUENCE: 1000
ctccgatgtc ttctgtgtgg gc                                         22

<210> SEQ ID NO 1001
<211> LENGTH: 23
<212> TYPE: DNA
<213> ORGANISM: brassica napus

<400> SEQUENCE: 1001
ctccgatgtc ttctgtgtgg gct                                        23

<210> SEQ ID NO 1002
<211> LENGTH: 15
<212> TYPE: DNA
<213> ORGANISM: brassica napus

<400> SEQUENCE: 1002
tccgatgtct tctgt                                                 15

<210> SEQ ID NO 1003
<211> LENGTH: 16
<212> TYPE: DNA
<213> ORGANISM: brassica napus

<400> SEQUENCE: 1003
tccgatgtct tctgtg                                                16

<210> SEQ ID NO 1004
<211> LENGTH: 17
<212> TYPE: DNA
<213> ORGANISM: brassica napus

<400> SEQUENCE: 1004
tccgatgtct tctgtgt                                               17

<210> SEQ ID NO 1005
<211> LENGTH: 18
<212> TYPE: DNA
<213> ORGANISM: brassica napus

<400> SEQUENCE: 1005
tccgatgtct tctgtgtg                                              18

<210> SEQ ID NO 1006
<211> LENGTH: 19
<212> TYPE: DNA
<213> ORGANISM: brassica napus

<400> SEQUENCE: 1006
tccgatgtct tctgtgtgg                                             19

<210> SEQ ID NO 1007
<211> LENGTH: 20
<212> TYPE: DNA
<213> ORGANISM: brassica napus
```

-continued

```
<400> SEQUENCE: 1007
tccgatgtct tctgtgtggg                                                20

<210> SEQ ID NO 1008
<211> LENGTH: 21
<212> TYPE: DNA
<213> ORGANISM: brassica napus

<400> SEQUENCE: 1008
tccgatgtct tctgtgtggg c                                              21

<210> SEQ ID NO 1009
<211> LENGTH: 22
<212> TYPE: DNA
<213> ORGANISM: brassica napus

<400> SEQUENCE: 1009
tccgatgtct tctgtgtggg ct                                             22

<210> SEQ ID NO 1010
<211> LENGTH: 23
<212> TYPE: DNA
<213> ORGANISM: brassica napus

<400> SEQUENCE: 1010
tccgatgtct tctgtgtggg ctt                                            23

<210> SEQ ID NO 1011
<211> LENGTH: 15
<212> TYPE: DNA
<213> ORGANISM: brassica napus

<400> SEQUENCE: 1011
ccgatgtctt ctgtg                                                     15

<210> SEQ ID NO 1012
<211> LENGTH: 16
<212> TYPE: DNA
<213> ORGANISM: brassica napus

<400> SEQUENCE: 1012
ccgatgtctt ctgtgt                                                    16

<210> SEQ ID NO 1013
<211> LENGTH: 17
<212> TYPE: DNA
<213> ORGANISM: brassica napus

<400> SEQUENCE: 1013
ccgatgtctt ctgtgtg                                                   17

<210> SEQ ID NO 1014
<211> LENGTH: 18
<212> TYPE: DNA
<213> ORGANISM: brassica napus

<400> SEQUENCE: 1014
ccgatgtctt ctgtgtgg                                                  18

<210> SEQ ID NO 1015
<211> LENGTH: 19
<212> TYPE: DNA
<213> ORGANISM: brassica napus
```

-continued

```
<400> SEQUENCE: 1015
ccgatgtctt ctgtgtggg                                               19

<210> SEQ ID NO 1016
<211> LENGTH: 20
<212> TYPE: DNA
<213> ORGANISM: brassica napus

<400> SEQUENCE: 1016
ccgatgtctt ctgtgtgggc                                              20

<210> SEQ ID NO 1017
<211> LENGTH: 21
<212> TYPE: DNA
<213> ORGANISM: brassica napus

<400> SEQUENCE: 1017
ccgatgtctt ctgtgtgggc t                                            21

<210> SEQ ID NO 1018
<211> LENGTH: 22
<212> TYPE: DNA
<213> ORGANISM: brassica napus

<400> SEQUENCE: 1018
ccgatgtctt ctgtgtgggc tt                                           22

<210> SEQ ID NO 1019
<211> LENGTH: 23
<212> TYPE: DNA
<213> ORGANISM: brassica napus

<400> SEQUENCE: 1019
ccgatgtctt ctgtgtgggc ttt                                          23

<210> SEQ ID NO 1020
<211> LENGTH: 15
<212> TYPE: DNA
<213> ORGANISM: brassica napus

<400> SEQUENCE: 1020
cgatgtcttc tgtgt                                                   15

<210> SEQ ID NO 1021
<211> LENGTH: 16
<212> TYPE: DNA
<213> ORGANISM: brassica napus

<400> SEQUENCE: 1021
cgatgtcttc tgtgtg                                                  16

<210> SEQ ID NO 1022
<211> LENGTH: 17
<212> TYPE: DNA
<213> ORGANISM: brassica napus

<400> SEQUENCE: 1022
cgatgtcttc tgtgtgg                                                 17

<210> SEQ ID NO 1023
<211> LENGTH: 18
<212> TYPE: DNA
```

```
<213> ORGANISM: brassica napus

<400> SEQUENCE: 1023
cgatgtcttc tgtgtgggg                                        18

<210> SEQ ID NO 1024
<211> LENGTH: 19
<212> TYPE: DNA
<213> ORGANISM: brassica napus

<400> SEQUENCE: 1024
cgatgtcttc tgtgtgggc                                        19

<210> SEQ ID NO 1025
<211> LENGTH: 20
<212> TYPE: DNA
<213> ORGANISM: brassica napus

<400> SEQUENCE: 1025
cgatgtcttc tgtgtgggct                                       20

<210> SEQ ID NO 1026
<211> LENGTH: 21
<212> TYPE: DNA
<213> ORGANISM: brassica napus

<400> SEQUENCE: 1026
cgatgtcttc tgtgtgggct t                                     21

<210> SEQ ID NO 1027
<211> LENGTH: 22
<212> TYPE: DNA
<213> ORGANISM: brassica napus

<400> SEQUENCE: 1027
cgatgtcttc tgtgtgggct tt                                    22

<210> SEQ ID NO 1028
<211> LENGTH: 23
<212> TYPE: DNA
<213> ORGANISM: brassica napus

<400> SEQUENCE: 1028
cgatgtcttc tgtgtgggct tta                                   23

<210> SEQ ID NO 1029
<211> LENGTH: 15
<212> TYPE: DNA
<213> ORGANISM: brassica napus

<400> SEQUENCE: 1029
gatgtcttct gtgtg                                            15

<210> SEQ ID NO 1030
<211> LENGTH: 16
<212> TYPE: DNA
<213> ORGANISM: brassica napus

<400> SEQUENCE: 1030
gatgtcttct gtgtgg                                           16

<210> SEQ ID NO 1031
<211> LENGTH: 17
```

```
<212> TYPE: DNA
<213> ORGANISM: brassica napus

<400> SEQUENCE: 1031
gatgtcttct gtgtggg                                                    17

<210> SEQ ID NO 1032
<211> LENGTH: 18
<212> TYPE: DNA
<213> ORGANISM: brassica napus

<400> SEQUENCE: 1032
gatgtcttct gtgtgggc                                                   18

<210> SEQ ID NO 1033
<211> LENGTH: 19
<212> TYPE: DNA
<213> ORGANISM: brassica napus

<400> SEQUENCE: 1033
gatgtcttct gtgtgggct                                                  19

<210> SEQ ID NO 1034
<211> LENGTH: 20
<212> TYPE: DNA
<213> ORGANISM: brassica napus

<400> SEQUENCE: 1034
gatgtcttct gtgtgggctt                                                 20

<210> SEQ ID NO 1035
<211> LENGTH: 21
<212> TYPE: DNA
<213> ORGANISM: brassica napus

<400> SEQUENCE: 1035
gatgtcttct gtgtgggctt t                                               21

<210> SEQ ID NO 1036
<211> LENGTH: 22
<212> TYPE: DNA
<213> ORGANISM: brassica napus

<400> SEQUENCE: 1036
gatgtcttct gtgtgggctt ta                                              22

<210> SEQ ID NO 1037
<211> LENGTH: 23
<212> TYPE: DNA
<213> ORGANISM: brassica napus

<400> SEQUENCE: 1037
gatgtcttct gtgtgggctt tat                                             23

<210> SEQ ID NO 1038
<211> LENGTH: 15
<212> TYPE: DNA
<213> ORGANISM: brassica napus

<400> SEQUENCE: 1038
atgtcttctg tgtgg                                                      15

<210> SEQ ID NO 1039
```

-continued

```
<211> LENGTH: 16
<212> TYPE: DNA
<213> ORGANISM: brassica napus

<400> SEQUENCE: 1039
atgtcttctg tgtggg                                                       16

<210> SEQ ID NO 1040
<211> LENGTH: 17
<212> TYPE: DNA
<213> ORGANISM: brassica napus

<400> SEQUENCE: 1040
atgtcttctg tgtgggc                                                      17

<210> SEQ ID NO 1041
<211> LENGTH: 18
<212> TYPE: DNA
<213> ORGANISM: brassica napus

<400> SEQUENCE: 1041
atgtcttctg tgtgggct                                                     18

<210> SEQ ID NO 1042
<211> LENGTH: 19
<212> TYPE: DNA
<213> ORGANISM: brassica napus

<400> SEQUENCE: 1042
atgtcttctg tgtgggctt                                                    19

<210> SEQ ID NO 1043
<211> LENGTH: 20
<212> TYPE: DNA
<213> ORGANISM: brassica napus

<400> SEQUENCE: 1043
atgtcttctg tgtgggcttt                                                   20

<210> SEQ ID NO 1044
<211> LENGTH: 21
<212> TYPE: DNA
<213> ORGANISM: brassica napus

<400> SEQUENCE: 1044
atgtcttctg tgtgggcttt a                                                 21

<210> SEQ ID NO 1045
<211> LENGTH: 22
<212> TYPE: DNA
<213> ORGANISM: brassica napus

<400> SEQUENCE: 1045
atgtcttctg tgtgggcttt at                                                22

<210> SEQ ID NO 1046
<211> LENGTH: 23
<212> TYPE: DNA
<213> ORGANISM: brassica napus

<400> SEQUENCE: 1046
atgtcttctg tgtgggcttt atg                                               23
```

-continued

```
<210> SEQ ID NO 1047
<211> LENGTH: 15
<212> TYPE: DNA
<213> ORGANISM: brassica napus

<400> SEQUENCE: 1047
ttaactatag tggcc                                                    15

<210> SEQ ID NO 1048
<211> LENGTH: 16
<212> TYPE: DNA
<213> ORGANISM: brassica napus

<400> SEQUENCE: 1048
ttaactatag tggcct                                                   16

<210> SEQ ID NO 1049
<211> LENGTH: 17
<212> TYPE: DNA
<213> ORGANISM: brassica napus

<400> SEQUENCE: 1049
ttaactatag tggcctt                                                  17

<210> SEQ ID NO 1050
<211> LENGTH: 18
<212> TYPE: DNA
<213> ORGANISM: brassica napus

<400> SEQUENCE: 1050
ttaactatag tggccttc                                                 18

<210> SEQ ID NO 1051
<211> LENGTH: 19
<212> TYPE: DNA
<213> ORGANISM: brassica napus

<400> SEQUENCE: 1051
ttaactatag tggccttca                                                19

<210> SEQ ID NO 1052
<211> LENGTH: 20
<212> TYPE: DNA
<213> ORGANISM: brassica napus

<400> SEQUENCE: 1052
ttaactatag tggccttcac                                               20

<210> SEQ ID NO 1053
<211> LENGTH: 21
<212> TYPE: DNA
<213> ORGANISM: brassica napus

<400> SEQUENCE: 1053
ttaactatag tggccttcac g                                             21

<210> SEQ ID NO 1054
<211> LENGTH: 22
<212> TYPE: DNA
<213> ORGANISM: brassica napus

<400> SEQUENCE: 1054
ttaactatag tggccttcac gc                                            22
```

-continued

```
<210> SEQ ID NO 1055
<211> LENGTH: 23
<212> TYPE: DNA
<213> ORGANISM: brassica napus

<400> SEQUENCE: 1055
ttaactatag tggccttcac gct                                           23

<210> SEQ ID NO 1056
<211> LENGTH: 15
<212> TYPE: DNA
<213> ORGANISM: brassica napus

<400> SEQUENCE: 1056
tgtcttctgt gtggg                                                    15

<210> SEQ ID NO 1057
<211> LENGTH: 16
<212> TYPE: DNA
<213> ORGANISM: brassica napus

<400> SEQUENCE: 1057
tgtcttctgt gtgggc                                                   16

<210> SEQ ID NO 1058
<211> LENGTH: 17
<212> TYPE: DNA
<213> ORGANISM: brassica napus

<400> SEQUENCE: 1058
tgtcttctgt gtgggct                                                  17

<210> SEQ ID NO 1059
<211> LENGTH: 18
<212> TYPE: DNA
<213> ORGANISM: brassica napus

<400> SEQUENCE: 1059
tgtcttctgt gtgggctt                                                 18

<210> SEQ ID NO 1060
<211> LENGTH: 19
<212> TYPE: DNA
<213> ORGANISM: brassica napus

<400> SEQUENCE: 1060
tgtcttctgt gtgggcttt                                                19

<210> SEQ ID NO 1061
<211> LENGTH: 20
<212> TYPE: DNA
<213> ORGANISM: brassica napus

<400> SEQUENCE: 1061
tgtcttctgt gtgggcttta                                               20

<210> SEQ ID NO 1062
<211> LENGTH: 21
<212> TYPE: DNA
<213> ORGANISM: brassica napus

<400> SEQUENCE: 1062
tgtcttctgt gtgggcttta t                                             21
```

-continued

```
<210> SEQ ID NO 1063
<211> LENGTH: 22
<212> TYPE: DNA
<213> ORGANISM: brassica napus

<400> SEQUENCE: 1063
tgtcttctgt gtgggcttta tg                                          22

<210> SEQ ID NO 1064
<211> LENGTH: 23
<212> TYPE: DNA
<213> ORGANISM: brassica napus

<400> SEQUENCE: 1064
tgtcttctgt gtgggcttta tga                                         23

<210> SEQ ID NO 1065
<211> LENGTH: 15
<212> TYPE: DNA
<213> ORGANISM: brassica napus

<400> SEQUENCE: 1065
gtcttctgtg tgggc                                                  15

<210> SEQ ID NO 1066
<211> LENGTH: 16
<212> TYPE: DNA
<213> ORGANISM: brassica napus

<400> SEQUENCE: 1066
gtcttctgtg tgggct                                                 16

<210> SEQ ID NO 1067
<211> LENGTH: 17
<212> TYPE: DNA
<213> ORGANISM: brassica napus

<400> SEQUENCE: 1067
gtcttctgtg tgggctt                                                17

<210> SEQ ID NO 1068
<211> LENGTH: 18
<212> TYPE: DNA
<213> ORGANISM: brassica napus

<400> SEQUENCE: 1068
gtcttctgtg tgggcttt                                               18

<210> SEQ ID NO 1069
<211> LENGTH: 19
<212> TYPE: DNA
<213> ORGANISM: brassica napus

<400> SEQUENCE: 1069
gtcttctgtg tgggcttta                                              19

<210> SEQ ID NO 1070
<211> LENGTH: 20
<212> TYPE: DNA
<213> ORGANISM: brassica napus

<400> SEQUENCE: 1070
```

-continued

```
gtcttctgtg tgggctttat                                        20

<210> SEQ ID NO 1071
<211> LENGTH: 21
<212> TYPE: DNA
<213> ORGANISM: brassica napus

<400> SEQUENCE: 1071
gtcttctgtg tgggctttat g                                      21

<210> SEQ ID NO 1072
<211> LENGTH: 22
<212> TYPE: DNA
<213> ORGANISM: brassica napus

<400> SEQUENCE: 1072
gtcttctgtg tgggctttat ga                                     22

<210> SEQ ID NO 1073
<211> LENGTH: 23
<212> TYPE: DNA
<213> ORGANISM: brassica napus

<400> SEQUENCE: 1073
gtcttctgtg tgggctttat gat                                    23

<210> SEQ ID NO 1074
<211> LENGTH: 15
<212> TYPE: DNA
<213> ORGANISM: brassica napus

<400> SEQUENCE: 1074
tcttctgtgt gggct                                             15

<210> SEQ ID NO 1075
<211> LENGTH: 16
<212> TYPE: DNA
<213> ORGANISM: brassica napus

<400> SEQUENCE: 1075
tcttctgtgt gggctt                                            16

<210> SEQ ID NO 1076
<211> LENGTH: 17
<212> TYPE: DNA
<213> ORGANISM: brassica napus

<400> SEQUENCE: 1076
tcttctgtgt gggcttt                                           17

<210> SEQ ID NO 1077
<211> LENGTH: 18
<212> TYPE: DNA
<213> ORGANISM: brassica napus

<400> SEQUENCE: 1077
tcttctgtgt gggcttta                                          18

<210> SEQ ID NO 1078
<211> LENGTH: 19
<212> TYPE: DNA
<213> ORGANISM: brassica napus

<400> SEQUENCE: 1078
```

-continued

```
tcttctgtgt gggctttat                                      19

<210> SEQ ID NO 1079
<211> LENGTH: 20
<212> TYPE: DNA
<213> ORGANISM: brassica napus

<400> SEQUENCE: 1079
tcttctgtgt gggctttatg                                     20

<210> SEQ ID NO 1080
<211> LENGTH: 21
<212> TYPE: DNA
<213> ORGANISM: brassica napus

<400> SEQUENCE: 1080
tcttctgtgt gggctttatg a                                   21

<210> SEQ ID NO 1081
<211> LENGTH: 22
<212> TYPE: DNA
<213> ORGANISM: brassica napus

<400> SEQUENCE: 1081
tcttctgtgt gggctttatg at                                  22

<210> SEQ ID NO 1082
<211> LENGTH: 23
<212> TYPE: DNA
<213> ORGANISM: brassica napus

<400> SEQUENCE: 1082
tcttctgtgt gggctttatg ata                                 23

<210> SEQ ID NO 1083
<211> LENGTH: 15
<212> TYPE: DNA
<213> ORGANISM: brassica napus

<400> SEQUENCE: 1083
cttctgtgtg ggctt                                          15

<210> SEQ ID NO 1084
<211> LENGTH: 16
<212> TYPE: DNA
<213> ORGANISM: brassica napus

<400> SEQUENCE: 1084
cttctgtgtg ggcttt                                         16

<210> SEQ ID NO 1085
<211> LENGTH: 17
<212> TYPE: DNA
<213> ORGANISM: brassica napus

<400> SEQUENCE: 1085
cttctgtgtg ggcttta                                        17

<210> SEQ ID NO 1086
<211> LENGTH: 18
<212> TYPE: DNA
<213> ORGANISM: brassica napus
```

-continued

```
<400> SEQUENCE: 1086
cttctgtgtg ggctttat                                              18

<210> SEQ ID NO 1087
<211> LENGTH: 19
<212> TYPE: DNA
<213> ORGANISM: brassica napus

<400> SEQUENCE: 1087
cttctgtgtg ggctttatg                                             19

<210> SEQ ID NO 1088
<211> LENGTH: 20
<212> TYPE: DNA
<213> ORGANISM: brassica napus

<400> SEQUENCE: 1088
cttctgtgtg ggctttatga                                            20

<210> SEQ ID NO 1089
<211> LENGTH: 21
<212> TYPE: DNA
<213> ORGANISM: brassica napus

<400> SEQUENCE: 1089
cttctgtgtg ggctttatga t                                          21

<210> SEQ ID NO 1090
<211> LENGTH: 22
<212> TYPE: DNA
<213> ORGANISM: brassica napus

<400> SEQUENCE: 1090
cttctgtgtg ggctttatga ta                                         22

<210> SEQ ID NO 1091
<211> LENGTH: 23
<212> TYPE: DNA
<213> ORGANISM: brassica napus

<400> SEQUENCE: 1091
cttctgtgtg ggctttatga taa                                        23

<210> SEQ ID NO 1092
<211> LENGTH: 15
<212> TYPE: DNA
<213> ORGANISM: brassica napus

<400> SEQUENCE: 1092
ttctgtgtgg gcttt                                                 15

<210> SEQ ID NO 1093
<211> LENGTH: 16
<212> TYPE: DNA
<213> ORGANISM: brassica napus

<400> SEQUENCE: 1093
ttctgtgtgg gcttta                                                16

<210> SEQ ID NO 1094
<211> LENGTH: 17
<212> TYPE: DNA
<213> ORGANISM: brassica napus
```

```
<400> SEQUENCE: 1094
ttctgtgtgg gctttat                                              17

<210> SEQ ID NO 1095
<211> LENGTH: 18
<212> TYPE: DNA
<213> ORGANISM: brassica napus

<400> SEQUENCE: 1095
ttctgtgtgg gctttatg                                             18

<210> SEQ ID NO 1096
<211> LENGTH: 19
<212> TYPE: DNA
<213> ORGANISM: brassica napus

<400> SEQUENCE: 1096
ttctgtgtgg gctttatga                                            19

<210> SEQ ID NO 1097
<211> LENGTH: 20
<212> TYPE: DNA
<213> ORGANISM: brassica napus

<400> SEQUENCE: 1097
ttctgtgtgg gctttatgat                                           20

<210> SEQ ID NO 1098
<211> LENGTH: 21
<212> TYPE: DNA
<213> ORGANISM: brassica napus

<400> SEQUENCE: 1098
ttctgtgtgg gctttatgat a                                         21

<210> SEQ ID NO 1099
<211> LENGTH: 22
<212> TYPE: DNA
<213> ORGANISM: brassica napus

<400> SEQUENCE: 1099
ttctgtgtgg gctttatgat aa                                        22

<210> SEQ ID NO 1100
<211> LENGTH: 23
<212> TYPE: DNA
<213> ORGANISM: brassica napus

<400> SEQUENCE: 1100
ttctgtgtgg gctttatgat aaa                                       23

<210> SEQ ID NO 1101
<211> LENGTH: 15
<212> TYPE: DNA
<213> ORGANISM: brassica napus

<400> SEQUENCE: 1101
tctgtgtggg cttta                                                15

<210> SEQ ID NO 1102
<211> LENGTH: 16
<212> TYPE: DNA
```

-continued

```
<213> ORGANISM: brassica napus

<400> SEQUENCE: 1102
tctgtgtggg cttat                                          16

<210> SEQ ID NO 1103
<211> LENGTH: 17
<212> TYPE: DNA
<213> ORGANISM: brassica napus

<400> SEQUENCE: 1103
tctgtgtggg cttatg                                         17

<210> SEQ ID NO 1104
<211> LENGTH: 18
<212> TYPE: DNA
<213> ORGANISM: brassica napus

<400> SEQUENCE: 1104
tctgtgtggg cttatga                                        18

<210> SEQ ID NO 1105
<211> LENGTH: 19
<212> TYPE: DNA
<213> ORGANISM: brassica napus

<400> SEQUENCE: 1105
tctgtgtggg cttatgat                                       19

<210> SEQ ID NO 1106
<211> LENGTH: 20
<212> TYPE: DNA
<213> ORGANISM: brassica napus

<400> SEQUENCE: 1106
tctgtgtggg cttatgata                                      20

<210> SEQ ID NO 1107
<211> LENGTH: 21
<212> TYPE: DNA
<213> ORGANISM: brassica napus

<400> SEQUENCE: 1107
tctgtgtggg cttatgata a                                    21

<210> SEQ ID NO 1108
<211> LENGTH: 22
<212> TYPE: DNA
<213> ORGANISM: brassica napus

<400> SEQUENCE: 1108
tctgtgtggg cttatgata aa                                   22

<210> SEQ ID NO 1109
<211> LENGTH: 23
<212> TYPE: DNA
<213> ORGANISM: brassica napus

<400> SEQUENCE: 1109
tctgtgtggg cttatgata aaa                                  23

<210> SEQ ID NO 1110
<211> LENGTH: 15
```

-continued

```
<212> TYPE: DNA
<213> ORGANISM: brassica napus

<400> SEQUENCE: 1110
ctgtgtgggc tttat                                                               15

<210> SEQ ID NO 1111
<211> LENGTH: 16
<212> TYPE: DNA
<213> ORGANISM: brassica napus

<400> SEQUENCE: 1111
ctgtgtgggc tttatg                                                              16

<210> SEQ ID NO 1112
<211> LENGTH: 17
<212> TYPE: DNA
<213> ORGANISM: brassica napus

<400> SEQUENCE: 1112
ctgtgtgggc tttatga                                                             17

<210> SEQ ID NO 1113
<211> LENGTH: 18
<212> TYPE: DNA
<213> ORGANISM: brassica napus

<400> SEQUENCE: 1113
ctgtgtgggc tttatgat                                                            18

<210> SEQ ID NO 1114
<211> LENGTH: 19
<212> TYPE: DNA
<213> ORGANISM: brassica napus

<400> SEQUENCE: 1114
ctgtgtgggc tttatgata                                                           19

<210> SEQ ID NO 1115
<211> LENGTH: 20
<212> TYPE: DNA
<213> ORGANISM: brassica napus

<400> SEQUENCE: 1115
ctgtgtgggc tttatgataa                                                          20
```